US012570673B2

(12) United States Patent
Tong et al.

(10) Patent No.: US 12,570,673 B2
(45) Date of Patent: Mar. 10, 2026

(54) C-MYC PROTEIN INHIBITOR, AND PREPARATION METHOD THEREFOR AND USE THEREOF

(71) Applicant: SUZHOU KINTOR PHARMACEUTICALS, INC., Suzhou (CN)

(72) Inventors: Youzhi Tong, New York, NY (US); Luhua Lai, Beijing (CN)

(73) Assignee: SUZHOU KINTOR PHARMACEUTICALS, INC., Suzhou (CN)

( * ) Notice: Subject to any disclaimer, the term of this patent is extended or adjusted under 35 U.S.C. 154(b) by 1030 days.

(21) Appl. No.: 17/597,311

(22) PCT Filed: Jul. 3, 2020

(86) PCT No.: PCT/CN2020/100103

§ 371 (c)(1),
(2) Date: Jan. 3, 2022

(87) PCT Pub. No.: WO2021/004391

PCT Pub. Date: Jan. 14, 2021

(65) Prior Publication Data

US 2022/0324884 A1 Oct. 13, 2022

(30) Foreign Application Priority Data

Jul. 8, 2019 (CN) ......................... 201910610585.1

(51) Int. Cl.
*C07F 5/02* (2006.01)
*A61P 35/00* (2006.01)

(52) U.S. Cl.
CPC .............. *C07F 5/025* (2013.01); *A61P 35/00* (2018.01)

(58) Field of Classification Search
None
See application file for complete search history.

(56) References Cited

U.S. PATENT DOCUMENTS

2009/0099132 A1* 4/2009 Olhava .................. C07F 5/025 564/8
2014/0296307 A1 10/2014 Fletcher

FOREIGN PATENT DOCUMENTS

CN 107522700 12/2017

OTHER PUBLICATIONS

English translation of International Search Report issued in International Patent Application No. PCT/CN2020/100103, dated Oct. 10, 2020.

Evinger-Hodges et al., "MYC and SIS expression in acute myelogenous leukemia," *Leukeumia*, 2(1):45-49, 1988. (Abstract only.).

Felsher and Bishop, "Reversible tumorigenesis by MYC in hematopoietic lineages," *Molecular Cell*, 4:199-207, 1999.

Herbst et al., "Multiple cell-type-specific elements regulate Myc protein stability," *Oncogene*, 23:3862-3871, 2004.

Kokai et al., "Myc regulate embryonic vascular permeability and remodeling," *Cir. Res.*, 104:1151-1159, 2009.

Korac et al., "Role of MYC in B cell lymphomagenesis," *Genes*, 8(115), 20 pages, 2017.

Lei et al., "3D-QSAR-aided Design, Synthesis, In Vitro and In Vivo Evaluation of Dipeptidyl Boronic Acid Proteasome Inhibitors and Mechanism Studies," *Bioorganic & Medicinal Chemistry*, 24(11):2576-88, 2013. (English abstract only).

Li et al., "Inactiviation of MUC reverses tumorignesis," *Journal of Internal Medicine*, 276:52-60, 2014.

Magid et al., "Expression of matrix metalloproteinase-9 in endothelial cells is differentially regulated by shear stress," *The Journal of Biological Chemistry*, 278(35):32994-32999, 2003.

Pedica et al., "A re-emerging marker for prognosis in hepatocellular carcinoma: The add-value of FISHing c-myc gene for early relapse," *PLoS One*, 8(7):e68203, 11 pages, 2013.

Pertschuk et al., "Steroid hormone receptor immunohistochemistry and amplification of c-myc protooncogene," *Cancer*, 71(1):162-71, 1993.

Prasad et al., "Decreased expressions of c-myc and H-ras oncogenes in vitamin E succinate induced morphologically differentiated murine B-16 melanoma cells in culture," *Biochem. Cell. Biol.*, 68(11):1250-5, 1990. (Abstract only).

Salvi et al., "Copy Number Analysis of 24 Oncogenes: MDM4 Identified as a Putative Marker for Low Recurrence Risk in Non Muscle Invasive Bladder Cancer," *Int. Jl. Mol. Sci.*, 15:12458-12468, 2014.

Tan et al., "De Novo Design of Boron-Based Peptidomimetics as Potent Inhibitors of Human ClpP in the Presence of Human ClpX," *Journal of Medicinal Chemistry*, 62(13): 6377-6390, 2019.

Wang et al., "Prognostic significane of c-myc and AIB1 amplification in hepatocellular carcinoma. A broad survey using high-throughput tissue microarray," *Cancer*, 95:2346-52, 2002.

Xie et al., "Target Validation and Identification of Novel Boronate Inhibitors of the Plasmodium falciparum Proteasome," *Journal of Medicinal Chemisry*, 61(22):10053-10066, 2018.

(Continued)

*Primary Examiner* — Craig D Ricci
(74) *Attorney, Agent, or Firm* — pH IP Law

(57) ABSTRACT

Provided are a c-Myc protein inhibitor, and a preparation method therefor and use thereof. The c-Myc protein inhibitor selectively inhibits c-Myc protein. Therefore, the inhibitor can be used for prevention and treatment of diseases related to c-Myc protein disorders, such as cancers, cardiovascular and cerebrovascular diseases, diseases related to virus infection.

3 Claims, 3 Drawing Sheets

(56) References Cited

OTHER PUBLICATIONS

Zheng et al., "c-MYC-making liver sick: Role of c-MYC in hepatic cell function, homeostasis and disease," *Genes*, 8(123), 20 pages, 2017.
Zhu et al., "Design, Synthesis, Biological Evaluation, and Structure-Activity Relationship (SAR) Discussion of Dipeptidy1 Boronate Proteasome Inhibitors, Part I: Comprehensive Understanding of the SAR of r-Amino Acid Boronates," *Journal of Medicinal Chemistry*, 52(14):4192-9, 2009.

* cited by examiner

C-MYC PROTEIN INHIBITOR, AND PREPARATION METHOD THEREFOR AND USE THEREOF

This application is a national phase application under 35 U.S.C. § 371 of International Application No. PCT/CN2020/100103, titled "C-MYC PROTEIN INHIBITOR, AND PREPARATION METHOD THEREFOR AND USE THEREOF", filed on Jul. 3, 2020, which claims the benefit of priority to Chinese Patent Application No. 201910610585.1, titled "C-MYC PROTEIN INHIBITOR, AND PREPARATION METHOD THEREFOR AND USE THEREOF", filed on Jul. 8, 2019 with the China National Intellectual Property Administration, which is incorporated herein by reference in entirety.

FIELD

The present disclosure belongs to the field of medicine, and specifically relates to a c-Myc protein inhibitor and a preparation method and application thereof.

BACKGROUND

Oncogenes are genes that exist in the genome of cells or viruses and the encoded products thereof can transform normal cells to form tumors. When such genes are in a normal state, they are called proto-oncogenes. Studies have found that proto-oncogenes are widely present in the biological world and have many important functions such as maintaining normal physiological functions, regulating cell growth and differentiation, including ras family, myc family, myb family, src family, sis family and so on. When affected by physical, chemical, microbial and other factors, proto-oncogenes can be mutated, amplified, and activated, thereby being transformed into oncogenes, and the encoded products of oncogenes can induce tumors in animals.

The human c-Myc proto-oncogene is located on human chromosome 8q24 and contains 3 exons and 2 introns, wherein exon 1 plays a regulatory role and does not participate in protein coding; exon 2 and exon 3 code together C-Myc protein. The c-Myc protein consists of the following structural groups, including: N-terminal transcriptional activation domain (TAD), which is necessary for activating target gene expression and includes two conserved domains, MBI and MBII; MBIII domain, which will affect the transcription and stability of c-Myc; the PEST region, which is involved in regulating the hydrolysis of c-Myc; CAPN, which is the site where calpain cleaves c-Myc, in which the truncated Myc-Nick will promote tumor survival and metastasis; MBIV region, which participates in the process of cell apoptosis; NLS, which is a nuclear localization area and regulates the Myc protein to enter into the nucleus and exert its transcriptional function; the C-terminal helix-turn-helix leucine zipper domain (bHLH-LZ), which can form heterodimers with the ligand protein Max, which bind to specific DNA sequences and activate the transcription of related genes (Herbst A et al. Oncogene 2004; 23(21): 3863-71). As a very unstable protein, c-Myc has a very short half-life in the cell. It is mainly degraded by ubiquitin-proteasome or kept stable by deubiquitination. C-Myc can regulate a variety of intracellular biology functions, such as cell proliferation, apoptosis, cell cycle progression, cell metabolism and embryonic development, play a very important role in the occurrence, development and evolution of diseases, especially in the occurrence and progression of tumors.

In normal cells, the expression of c-Myc is strictly regulated. In quiescent cells, the expression of c-Myc is very small. When stimulated by growth factors, c-Myc accumulates rapidly as the initial response gene and maintains a high level throughout the cell cycle, affecting the expression of downstream target genes until the cells returned to the original level after the cells entered the quiescent phase (Magid R et al. J Biol Chem 2003; 278(35): 32994-9).

A large number of studies have shown that c-Myc is closely related to 70% of tumor diseases, including lymphoma, breast cancer, prostate cancer, colon cancer, cervical cancer, multiple myeloma, myelogenous leukemia, melanoma, osteosarcoma, malignant glia tumor, small cell lung cancer, and medulloblastoma. C-Myc can promote tumor occurrence and growth in many aspects. After c-Myc is activated, the protein encoded by c-Myc is overexpressed, causing cell transformation and tumor formation. Felsher et al. found that during the construction of a c-Myc transgene model in mouse hematopoietic cells, the expression of the transgene can lead to occurrence of malignant lymphoma and myeloid tumor. The role of c-Myc in regulating the cell cycle is more effective in tumor cells, accelerating cell proliferation, and knocking out c-Myc in tumor cells in vitro can hinder cell proliferation and arrest the cell cycle. In the tumorigenesis process, new blood vessels are the guarantee for its survival. In the low oxygen environment inside the tumor, hypoxia inducible factor-la (HIF-la) can promote tumor angiogenesis, and c-Myc can induce the expression of HIF-la and promote angiogenesis. When c-Myc and HIF-la are down-regulated, it will eventually inhibit vascular endothelial growth factor VEGF and angiogenesis. In addition, the poor prognosis of many tumors is related to the expansion of c-Myc. Among uterine carcinosarcomas with elevated c-Myc expression, the recurrence rate of even early patients reaches 30% to 50% (Salvi S et al. Int J Mol Sci, 2014, 15(7): 12458-12468).

C-Myc dysregulation is a characteristic of many types of B-cell lymphomas. In these lymphomas, c-Myc overexpression inhibits the development of normal B cells, leading to cell recoding. Nearly 70% of B-cell lymphomas also carry mutations in upstream regulatory factors involved in the TCF3-ID3 pathway, leading to increased cell survival. Among them, c-Myc can affect the regulation of TCF3-ID3, thereby affecting the expression of cyclin 3 and promoting proliferation and growth of tumor cells (Petra Korac et al. Genes 2017, 8, 115).

C-Myc is expressed in almost all types of leukemia. In 1988, Wickstrom and Holt respectively synthesized the antisense oligodeoxynucleotide ASODN of c-Myc mRNA and co-cultured it with HL60 cells in vitro, which effectively inhibited the expression of c-Myc, inhibited cell growth and inhibited the formation of leukemia cell colonies, indicating that c-Myc gene plays an important role in the occurrence of leukemia. In subsequent studies, it was found that c-Myc expression is the strongest in acute lymphocytic leukemia and acute non-lymphocytic leukemia, and the c-Myc expression in chronic myelogenous leukemia (CML), myelodysplastic syndrome (MDS) and multiple myeloma (MM) is much lower than in acute leukemia, but significantly higher than in control cells. Studies have found that patients with high expression of c-Myc mRNA are difficult to relieve under the induction of chemotherapy drugs. The lower the expression of c-Myc, the higher the complete remission rate and the longer disease-free survival (Evingerhodges M J et al. Leukemia, 1988), 2(1):45.).

In breast cancer, about 30% of patients have high expression of c-Myc. In a set of clinical data, it was found that compared with the normal expression group, the postoperative disease-free survival of the c-Myc high expression group was declined to 1.4 years from greater than 6.4 years. And in extreme cases, the postoperative recurrence rate of lymph node negative, estrogen and progesterone receptor positive, and low c-Myc expression is 0%, while the recurrence rate of lymph node metastasis, estrogen and progesterone receptor negative and high c-Myc expression is 93% (Pertschuk et al. Cancer, 1993, 71(1): 162).

Recent studies have found that c-Myc is one of the most highly expressed oncogenes in liver cancer, and it has been found that c-Myc overexpression is often detected in patients and models of advanced liver fibrosis. After chronic injury in the mouse model, the regulation of c-Myc leads to hepatocyte apoptosis, increased proliferation, and abnormal expression of platelet-derived growth factor subunits (PDGF-B). Liver cirrhosis and chronic liver disease often lead to liver cancer. At present, it has been found that the hypomethylation of c-Myc gene is related to the occurrence and development of liver cancer. Through the study of mouse experimental models, it has been found that it can be used as new markers and new targets for treatment in liver cirrhosis and chronic liver disease (Kang Zheng et al. Genes 2017, 8, 123; doi:10.3390). At the same time, c-Myc is an indicator of poor prognosis of liver cancer, and the survival time of patients with c-Myc overexpression is significantly shortened. Compared with primary liver cancer, higher c-Myc expression is detected in metastatic and recurrent liver cancer (Wang, Y. et al. Cancer 2002, 95, 2346-2352). In addition, the metastasis of liver cancer cells is mediated through multiple signaling pathways of c-Myc (Pedica F et al. PLoS One, 2013, 8(7)).

C-Myc is also an important mediator of tumor occurrence and maintenance. C-Myc initiates and maintains the occurrence of tumors by regulating multiple programs, including DNA replication, survival, death, self-renewal and energy metabolism of cells, in the tumor microenvironment (such as the regulation of secreted factors and angiogenesis) and the immune response impact (Yulin Li J Intern Med. 2014 July; 276(1):52-60.). The inhibition of c-Myc can reverse tumorigenesis and lead to proliferation arrest. In addition, it was found that c-Myc inactivation can reconstruct the microenvironment, restore normal tissue structure and block angiogenesis. Similar results have been observed in a variety of tumors, including hematopoietic (T-cell and B-cell lymphoma, leukemia), epithelial (hepatocellular, breast and squamous cell carcinoma) and mesenchymal tumors (osteosarcoma) (Felsher D W, Bishop J M Mol Cell. 1999 August; 4(2):199-207.) Therefore, c-Myc as an anti-tumor target will have broad application prospects.

In addition to cancer, c-Myc is also associated with some other diseases. Diabetes is caused by the complete or relative absence of β-islet cells. In diabetes, with the increase of c-Myc expression, the β-islet cells that produce insulin dedifferentiate or apoptotic, and their insulin secretion decreases. This is because c-Myc lacks the function of activating insulin gene expression, and inhibits gene transcription and expression through the E-box structure of the integrated insulin gene promoter that competes with the transcription factor NeuroD (Magid R et al. J Biol Chem, 2003, 278: 32994).

Atherosclerosis and vascular proliferative diseases have some similar pathological mechanisms with tumors. In the monoclonal hypothesis of atherosclerosis, the increased expression of c-Myc in vivo is related to the production of aortic and carotid plaques. In fact, the activation of c-Myc-dependent signaling pathway was found in the early-onset coronary artery disease in the Watanabe hyperlipidemia rabbit model and the early coronary artery wall lipid accumulation in hypercholesterolemia pigs. More importantly, antioxidants down-regulated c-Myc overexpression with a similar pattern observed in tumor cells (Prasad K N et al. Biochem Cell Biol 68, 1250-55.). Restenosis after arterial injury is mainly caused by the proliferation of vascular cells and eventually leads to arterial occlusion. In addition, cell migration, matrix deposition and vascular remodeling are also involved in the occurrence of restenosis after arterial injury. C-Myc has been found to be critical to the proliferation of vascular smooth muscle cells. After the saccule is damaged, the mRNA level of c-Myc reaches a peak in 2 hours. The c-Myc protein binds to DNA, promotes the opening of genes related to cell proliferation, stimulates smooth muscle cells in the resting phase to produce proliferative effects, and c-Myc can also regulate the expression level of vascular endothelial growth factor VEGFA, which has an important impact on the regeneration and maturation of blood vessels (Kokai et al. Circulation Reserach, 2009, 1151).

At present, many studies have confirmed the clinical development prospects of c-Myc as an anti-tumor target, but there are no reports of highly active c-Myc inhibitors. The problem of drug resistance of antitumor drugs is becoming more and more serious, and drugs with new mechanisms of action are urgently needed to meet the huge clinical demand. The disclosure of the present invention provides compounds with strong inhibitory activity targeting c-Myc.

SUMMARY

The present disclosure aims to provide a c-Myc protein inhibitor and preparation method and application thereof.

In one aspect, the present disclosure provides compounds represented by formula (I) or a pharmaceutically acceptable salt, a solvate, a stereoisomer or a prodrug thereof:

(I)

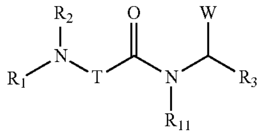

wherein, T is selected from $CHR_4$, $CR_4R5$;

W is $BZ_1Z_2$;

$R_1$ is selected from: RAC(═O)—, RANHC(═O)—, RAOC(═O)—, $RACH_2C$(═O)—; $RAS(═O)_2$— or RA;

RA is selected from: $C_1$-$C_4$ alkyl, $C_3$-$C_8$ cycloalkyl, any $C_3$-$C_8$ heterocyclyl optionally containing O, S, $SO_2$, N or NHC(═O)$R_8$, aryl, heteroaryl, aryl-cycloalkyl, aryl-heterocyclyl, cycloalkyl-heterocyclyl, heterocyclyl-heterocyclyl, RA may be optionally substituted by one or more $R_6$;

$R_2$ is selected from hydrogen, $C_1$-$C_3$ alkyl, $C_3$-$C_6$ cycloalkyl;

$R_3$ is selected from hydrogen, $C_1$-$C_6$ alkyl, $C_3$-$C_6$ cycloalkyl, phenyl or benzyl, the alkyl, cycloalkyl, phenyl or benzyl is optionally substituted by 1-3 substituents independently selected from halogen, cyano, $C_1$-$C_3$ alkyl or $C_1$-$C_3$ alkoxy, $R_3$ and $R_{11}$ can form $C_4$-$C_6$ cycloalkyl;

$R_4$ and $R_5$ are independently selected from hydroxyl, amino, $R_7NHC(=O)R_8$, $R_7C(=O)OR_8$, $C_1$-$C_6$ alkyl, $C_1$-$C_6$ alkoxy, $C_1$-$C_6$ alkylthio, $C_1$-$C_6$ alkylamine, $C_3$-$C_8$ cycloalkyl, aryl, 5-6 membered heteroaryl containing 1-3 heteroatoms or 3-10 membered heterocyclyl containing 1-3 heteroatoms, the alkyl, alkoxy, alkylamine, alkylthio, cycloalkyl, aryl, heteroaryl, heterocyclyl are optionally substituted by 1-3 substituents independently selected from halogen, cyano, $C_1$-$C_3$ alkyl or $C_1$-$C_3$ alkoxy, wherein $R_4$ and $R_5$ can form a saturated $C_3$-$C_6$ ring or a saturated heterocyclic ring optionally containing O, S, $SO_2$, N or $NHC(=O)R_8$;

$R_6$ is selected from hydrogen, halogen, hydroxyl, cyano, amino, $R_7NHC(=O)R_8$, $R_7C(=O)OR_8$, $C_1$-$C_6$ alkyl, $C_1$-$C_6$ alkoxy, $C_1$-$C_6$ alkylthio, $C_1$-$C_6$ alkylamino, $C_3$-$C_8$ cycloalkyl, $C_2$-$C_8$ alkenyl, $C_2$-$C_8$ alkynyl, aryl, 5-6 membered heteroaryl containing 1-3 heteroatoms or 3-10 membered heterocyclyl containing 1-3 heteroatoms, the alkyl, alkoxy, alkylamino, alkylthio, cycloalkyl, aryl, heteroaryl, heterocyclyl are optionally substituted with 1-3 groups selected from halogen, cyano, $C_1$-$C_3$ alkyl or $C_1$-$C_3$ alkoxy;

$R_7$ is selected from $C_1$-$C_4$ alkyl;

$R_8$ is selected from hydrogen, $C_1$-$C_4$ alkyl, allyl or benzyl;

$R_{11}$ is hydrogen, $C_1$-$C_3$ alkyl, $C_3$ cycloalkyl;

$Z_1$ and $Z_2$ are independently selected from hydroxyl, $C_1$-$C_{10}$ alkyl, $C_1$-$C_{10}$ alkoxy or aryloxy. B, $Z_1$ and $Z_2$ can together form heterocyclyl containing N, S or O.

In some embodiments, the compound is a compound represented by formula (II) or a pharmaceutically acceptable salt, solvate, stereoisomer, or prodrug thereof:

(II)

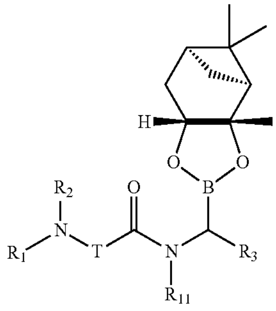

wherein, T, $R_1$, $R_2$, $R_3$, and $R_{11}$ are as defined above.

Specifically, the disclosure provides the following compounds:

| Compound No. | Compound Structure |
|---|---|
| A1 | 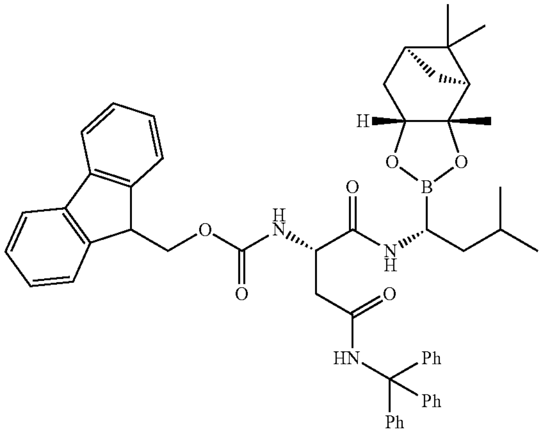 [SMILES: CC(C)C[C@H](NC(=O)[C@H](CC(=O)NC(c1ccccc1)(c1ccccc1)c1ccccc1)NC(=O)OCC1c2ccccc2-c2ccccc21)B1O[C@@H]2C[C@@H]3C[C@@H](C3(C)C)[C@]2(C)O1] |
| A2 | 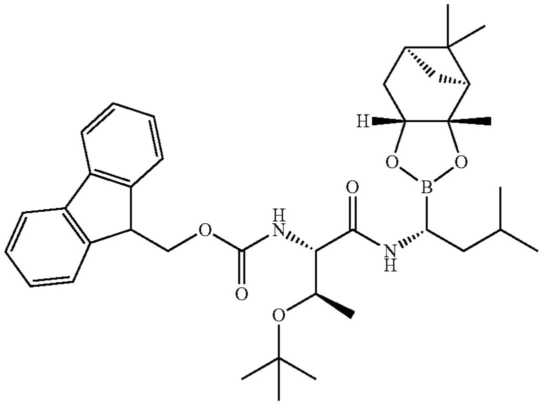 [SMILES: CC(C)C[C@H](NC(=O)[C@@H](NC(=O)OCC1c2ccccc2-c2ccccc21)[C@@H](C)OC(C)(C)C)B1O[C@@H]2C[C@@H]3C[C@@H](C3(C)C)[C@]2(C)O1] |

-continued
| Compound No. | Compound Structure |
|---|---|
| A3 | 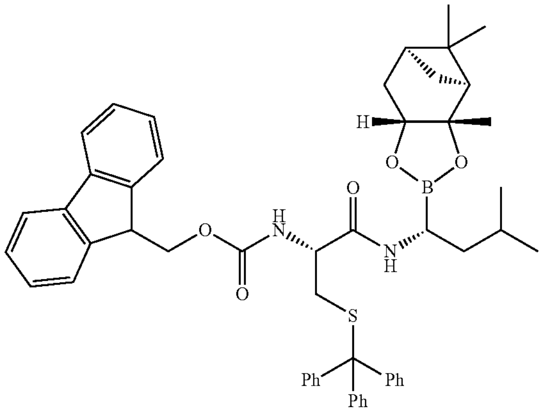 [SMILES: CC(C)C[C@H](NC(=O)[C@H](CSC(c1ccccc1)(c1ccccc1)c1ccccc1)NC(=O)OCC1c2ccccc2-c2ccccc21)B1O[C@@H]2C[C@@H]3C[C@@H](C3(C)C)[C@]2(C)O1] |
| A4 | 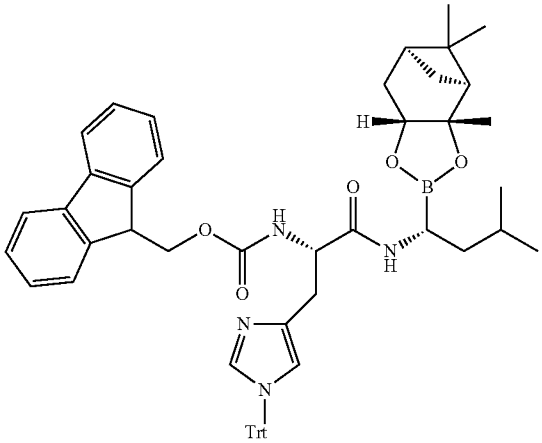 |
| A5 | 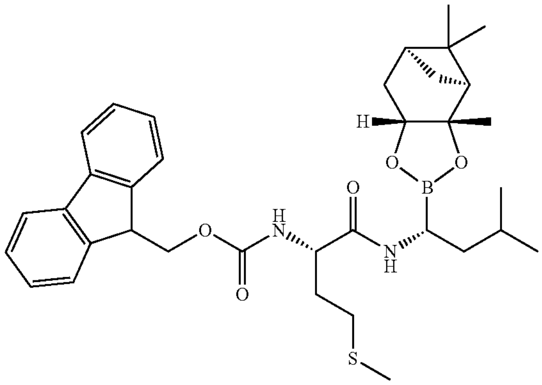 [SMILES: CSCC[C@H](NC(=O)OCC1c2ccccc2-c2ccccc21)C(=O)N[C@@H](CC(C)C)B1O[C@@H]2C[C@@H]3C[C@@H](C3(C)C)[C@]2(C)O1] |

-continued
| Compound No. | Compound Structure |
| --- | --- |
| A6 | 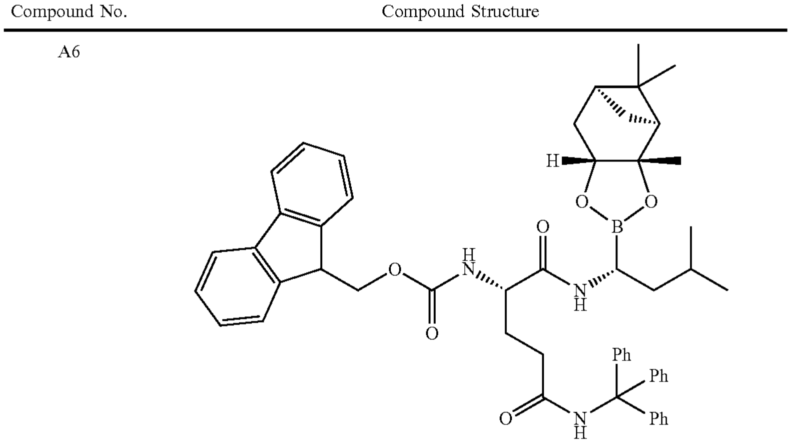 |
| A7 | 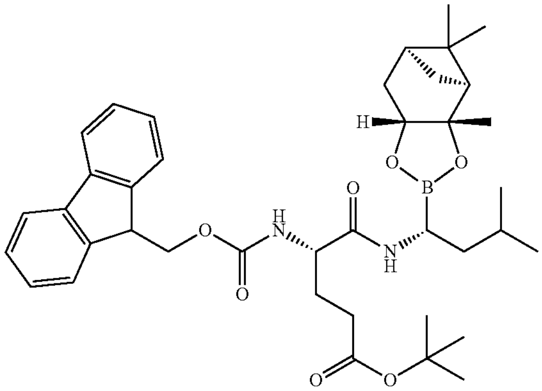 [SMILES: CC(C)C[C@H](NC(=O)[C@H](CCC(=O)OC(C)(C)C)NC(=O)OCC1c2ccccc2-c2ccccc21)B1O[C@@H]2C[C@@H]3C[C@@H](C3(C)C)[C@]2(C)O1] |
| A8 | 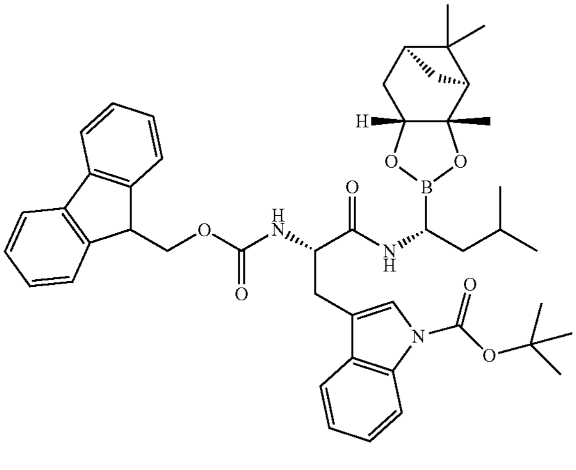 [SMILES: CC(C)C[C@H](NC(=O)[C@H](Cc1cn(C(=O)OC(C)(C)C)c2ccccc12)NC(=O)OCC1c2ccccc2-c2ccccc21)B1O[C@@H]2C[C@@H]3C[C@@H](C3(C)C)[C@]2(C)O1] |

-continued
| Compound No. | Compound Structure |
|---|---|
| A9 | 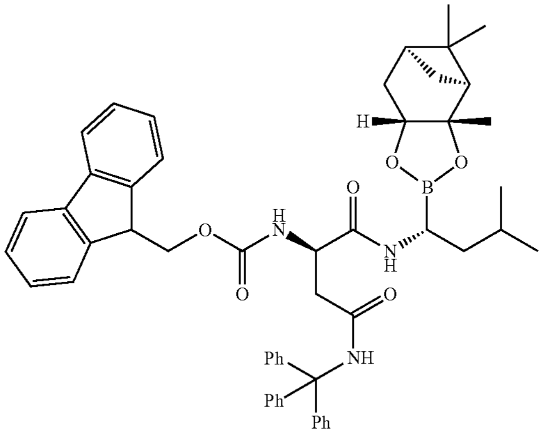 [SMILES: CC(C)C[C@H](NC(=O)[C@@H](CC(=O)NC(c1ccccc1)(c1ccccc1)c1ccccc1)NC(=O)OCC1c2ccccc2-c2ccccc21)B1O[C@@H]2C[C@@H]3C[C@@H](C3(C)C)[C@]2(C)O1] |
| A10 | 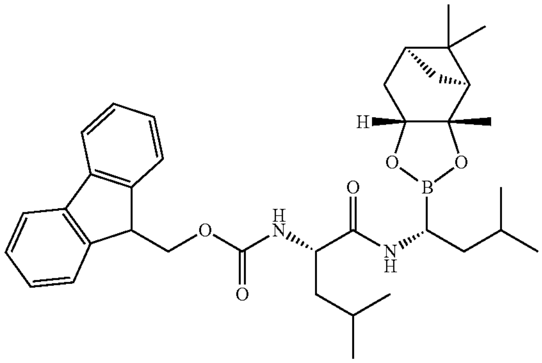 [SMILES: CC(C)C[C@H](NC(=O)[C@H](CC(C)C)NC(=O)OCC1c2ccccc2-c2ccccc21)B1O[C@@H]2C[C@@H]3C[C@@H](C3(C)C)[C@]2(C)O1] |
| A11 | 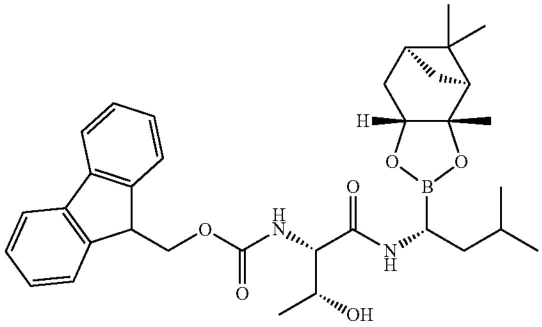 [SMILES: CC(C)C[C@H](NC(=O)[C@@H](NC(=O)OCC1c2ccccc2-c2ccccc21)[C@@H](C)O)B1O[C@@H]2C[C@@H]3C[C@@H](C3(C)C)[C@]2(C)O1] |
| A12 | 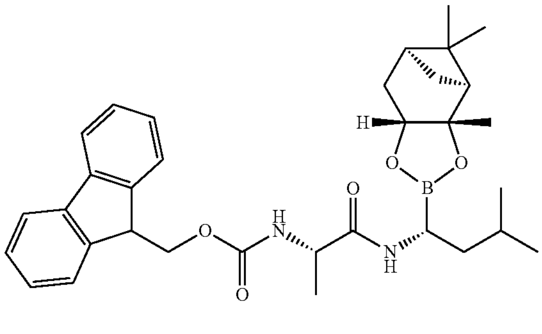 [SMILES: CC(C)C[C@H](NC(=O)[C@H](C)NC(=O)OCC1c2ccccc2-c2ccccc21)B1O[C@@H]2C[C@@H]3C[C@@H](C3(C)C)[C@]2(C)O1] |

-continued
| Compound No. | Compound Structure |
|---|---|
| A13 | 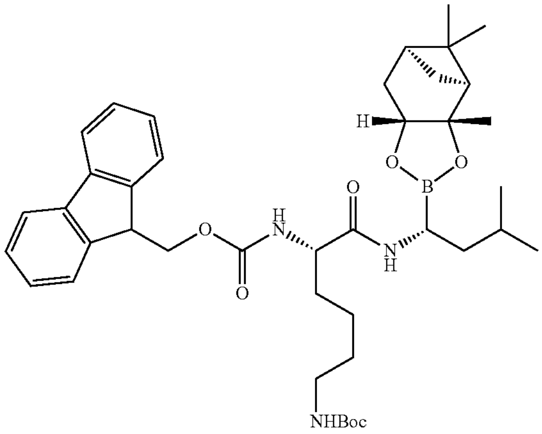 [SMILES: CC(C)C[C@H](NC(=O)[C@H](CCCCNC(=O)OC(C)(C)C)NC(=O)OCC1c2ccccc2-c2ccccc21)B1O[C@@H]2C[C@@H]3C[C@@H](C3(C)C)[C@]2(C)O1] |
| A14 | 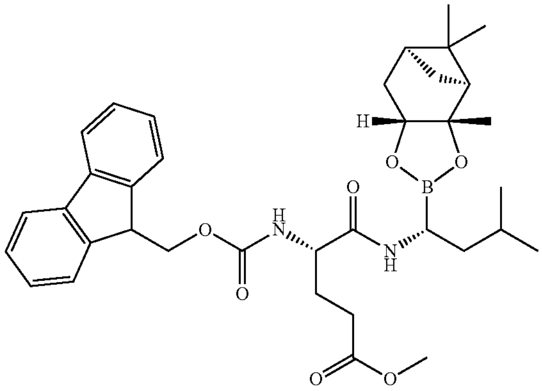 [SMILES: COC(=O)CC[C@H](NC(=O)OCC1c2ccccc2-c2ccccc21)C(=O)N[C@@H](CC(C)C)B1O[C@@H]2C[C@@H]3C[C@@H](C3(C)C)[C@]2(C)O1] |
| A15 | 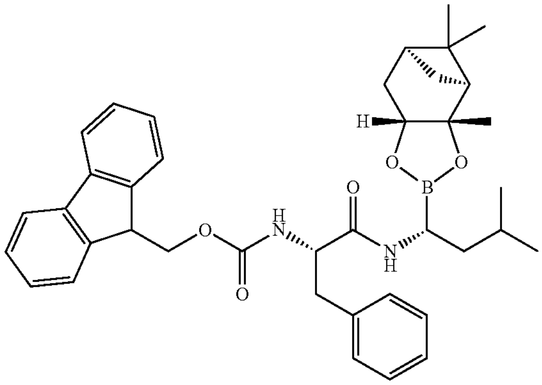 [SMILES: CC(C)C[C@H](NC(=O)[C@H](Cc1ccccc1)NC(=O)OCC1c2ccccc2-c2ccccc21)B1O[C@@H]2C[C@@H]3C[C@@H](C3(C)C)[C@]2(C)O1] |
| A16 | 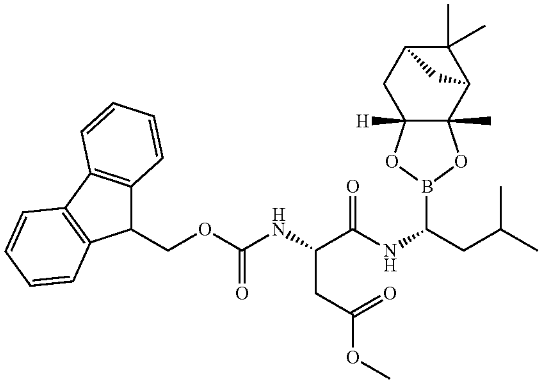 [SMILES: COC(=O)C[C@H](NC(=O)OCC1c2ccccc2-c2ccccc21)C(=O)N[C@@H](CC(C)C)B1O[C@@H]2C[C@@H]3C[C@@H](C3(C)C)[C@]2(C)O1] |

-continued
| Compound No. | Compound Structure |
|---|---|
| A17 | 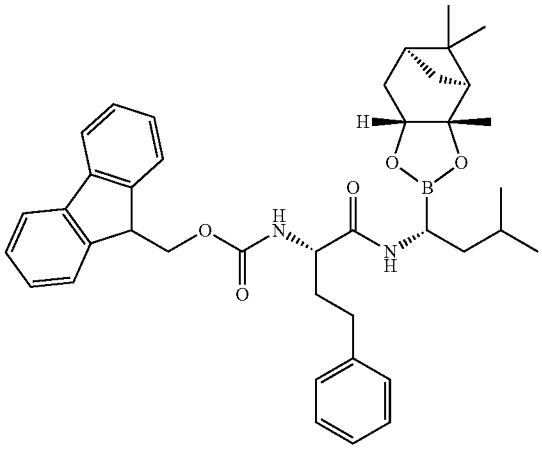 [SMILES: CC(C)C[C@H](NC(=O)[C@H](CCc1ccccc1)NC(=O)OCC1c2ccccc2-c2ccccc21)B1O[C@@H]2C[C@@H]3C[C@@H](C3(C)C)[C@]2(C)O1] |
| A18 | 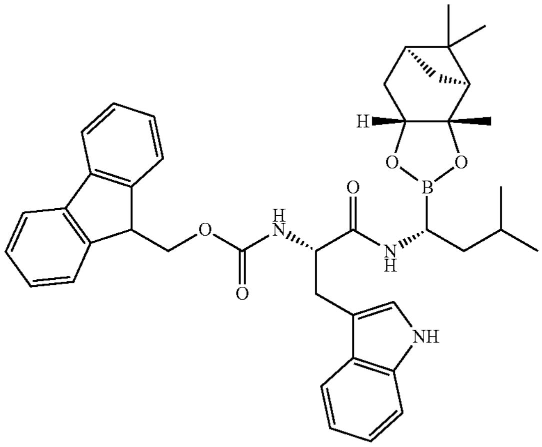 [SMILES: CC(C)C[C@H](NC(=O)[C@H](Cc1c[nH]c2ccccc12)NC(=O)OCC1c2ccccc2-c2ccccc21)B1O[C@@H]2C[C@@H]3C[C@@H](C3(C)C)[C@]2(C)O1] |
| A19 | 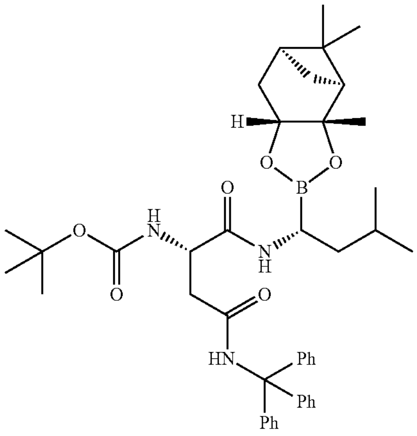 [SMILES: CC(C)C[C@H](NC(=O)[C@H](CC(=O)NC(c1ccccc1)(c1ccccc1)c1ccccc1)NC(=O)OC(C)(C)C)B1O[C@@H]2C[C@@H]3C[C@@H](C3(C)C)[C@]2(C)O1] |

-continued
| Compound No. | Compound Structure |
|---|---|
| A20 | 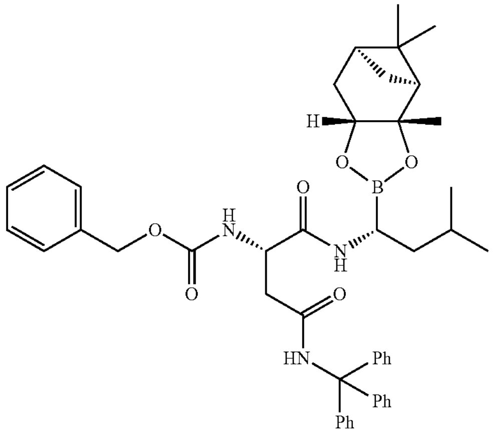 [SMILES: CC(C)C[C@H](NC(=O)[C@H](CC(=O)NC(c1ccccc1)(c1ccccc1)c1ccccc1)NC(=O)OCc1ccccc1)B1O[C@@H]2C[C@@H]3C[C@@H](C3(C)C)[C@]2(C)O1] |
| A21 | 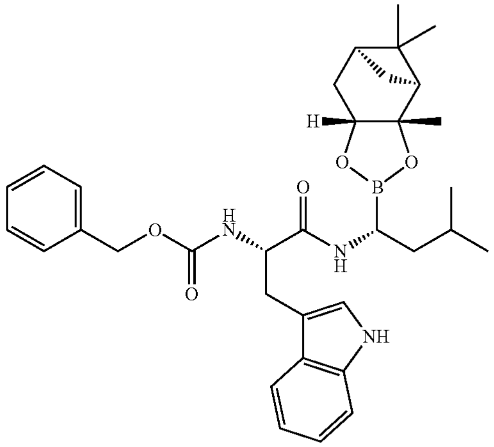 [SMILES: CC(C)C[C@H](NC(=O)[C@H](Cc1c[nH]c2ccccc12)NC(=O)OCc1ccccc1)B1O[C@@H]2C[C@@H]3C[C@@H](C3(C)C)[C@]2(C)O1] |
| A22 | 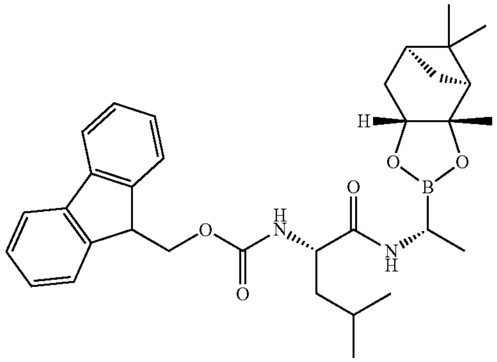 [SMILES: CC(C)C[C@H](NC(=O)OCC1c2ccccc2-c2ccccc21)C(=O)N[C@@H](C)B1O[C@@H]2C[C@@H]3C[C@@H](C3(C)C)[C@]2(C)O1] |

-continued
| Compound No. | Compound Structure |
| --- | --- |
| A23 | 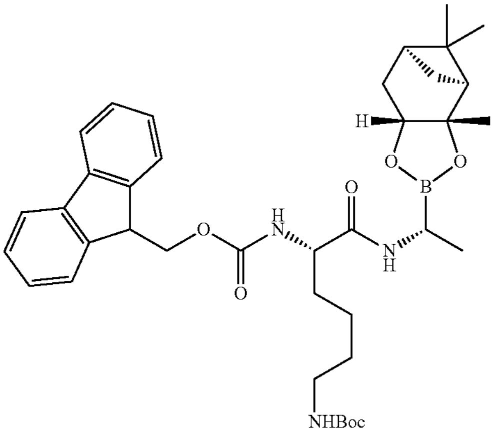 [SMILES: C[C@H](NC(=O)[C@H](CCCCNC(=O)OC(C)(C)C)NC(=O)OCC1c2ccccc2-c2ccccc21)B1O[C@@H]2C[C@@H]3C[C@@H](C3(C)C)[C@]2(C)O1] |
| A24 | 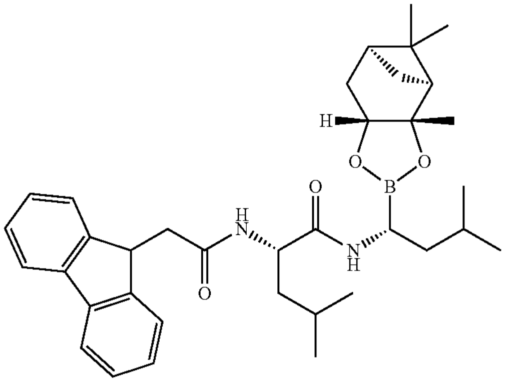 [SMILES: CC(C)C[C@H](NC(=O)[C@H](CC(C)C)NC(=O)CC1c2ccccc2-c2ccccc21)B1O[C@@H]2C[C@@H]3C[C@@H](C3(C)C)[C@]2(C)O1] |
| A25 | 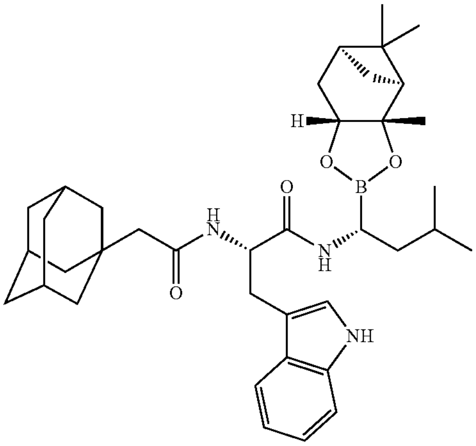 [SMILES: CC(C)C[C@H](NC(=O)[C@H](Cc1c[nH]c2ccccc12)NC(=O)CC12CC3CC(CC(C3)C1)C2)B1O[C@@H]2C[C@@H]3C[C@@H](C3(C)C)[C@]2(C)O1] |

-continued
| Compound No. | Compound Structure |
| --- | --- |
| A26 | 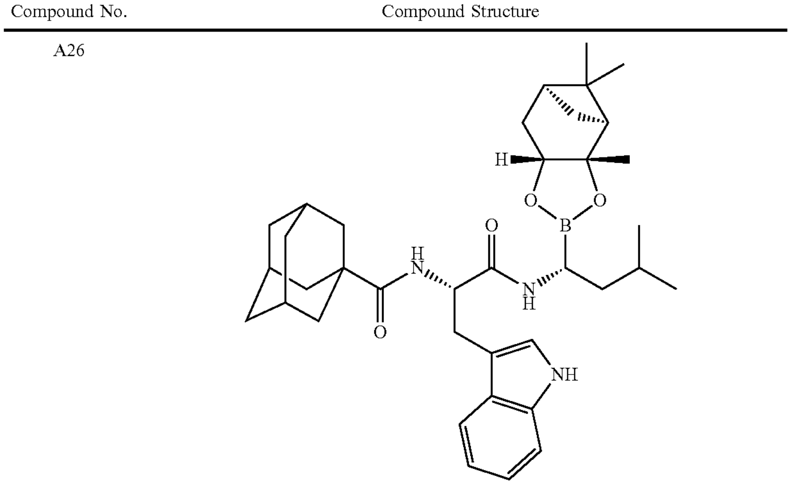 |
| A27 | 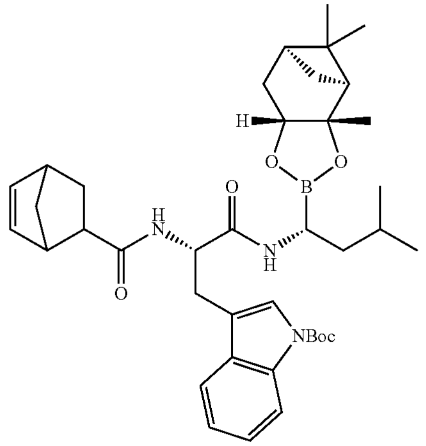 [SMILES: CC(C)C[C@H](NC(=O)[C@H](Cc1cn(C(=O)OC(C)(C)C)c2ccccc12)NC(=O)C1CC2C=CC1C2)B1O[C@@H]2C[C@@H]3C[C@@H](C3(C)C)[C@]2(C)O1] |
| A28 | 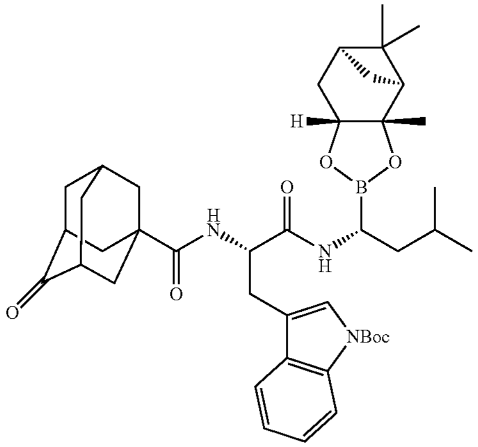 [SMILES: CC(C)C[C@H](NC(=O)[C@H](Cc1cn(C(=O)OC(C)(C)C)c2ccccc12)NC(=O)C12CC3CC(C1)C(=O)C(C3)C2)B1O[C@@H]2C[C@@H]3C[C@@H](C3(C)C)[C@]2(C)O1] |

-continued
| Compound No. | Compound Structure |
|---|---|
| A29 | 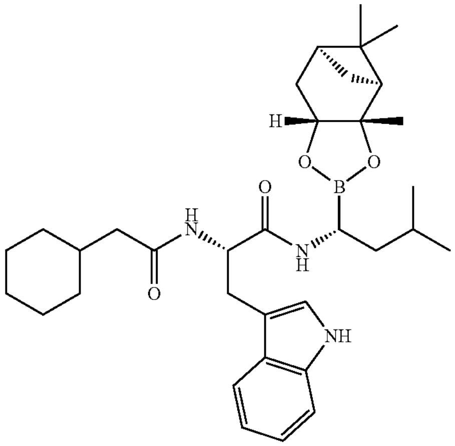 [SMILES: CC(C)C[C@H](NC(=O)[C@H](Cc1c[nH]c2ccccc12)NC(=O)CC1CCCCC1)B1O[C@@H]2C[C@@H]3C[C@@H](C3(C)C)[C@]2(C)O1] |
| A30 | 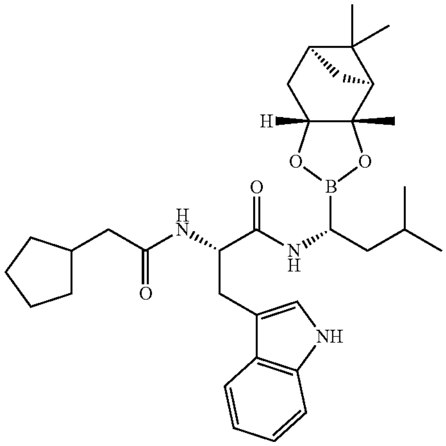 [SMILES: CC(C)C[C@H](NC(=O)[C@H](Cc1c[nH]c2ccccc12)NC(=O)CC1CCCC1)B1O[C@@H]2C[C@@H]3C[C@@H](C3(C)C)[C@]2(C)O1] |
| A31 | 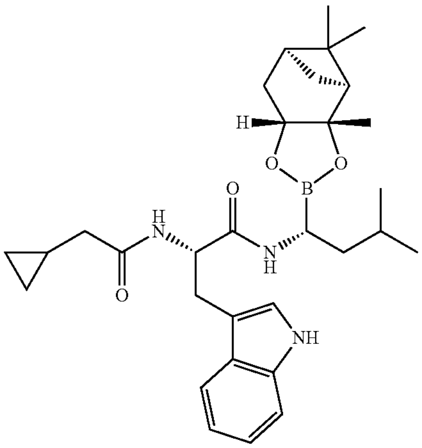 [SMILES: CC(C)C[C@H](NC(=O)[C@H](Cc1c[nH]c2ccccc12)NC(=O)CC1CC1)B1O[C@@H]2C[C@@H]3C[C@@H](C3(C)C)[C@]2(C)O1] |

-continued
| Compound No. | Compound Structure |
|---|---|
| A32 | 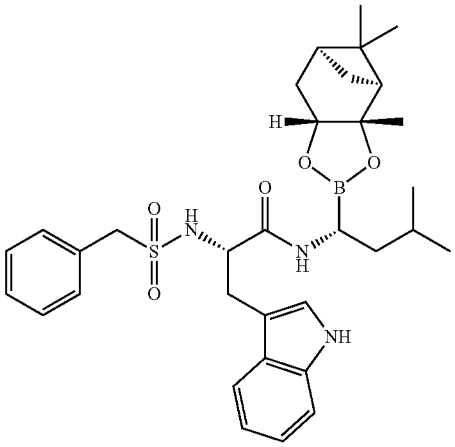 [SMILES: CC(C)C[C@H](NC(=O)[C@H](Cc1c[nH]c2ccccc12)NS(=O)(=O)Cc1ccccc1)B1O[C@@H]2C[C@@H]3C[C@@H](C3(C)C)[C@]2(C)O1] |
| A33 | 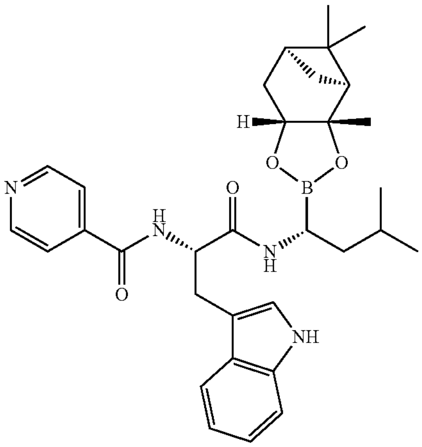 [SMILES: CC(C)C[C@H](NC(=O)[C@H](Cc1c[nH]c2ccccc12)NC(=O)c1ccncc1)B1O[C@@H]2C[C@@H]3C[C@@H](C3(C)C)[C@]2(C)O1] |
| A34 | 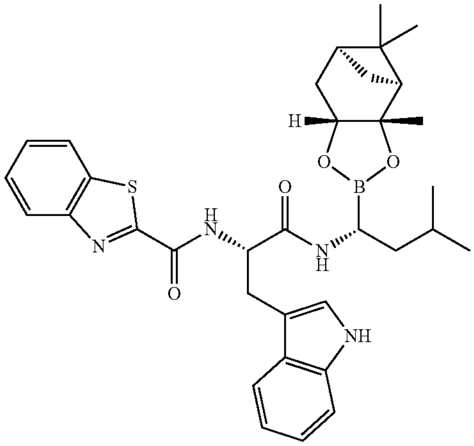 [SMILES: CC(C)C[C@H](NC(=O)[C@H](Cc1c[nH]c2ccccc12)NC(=O)c1nc2ccccc2s1)B1O[C@@H]2C[C@@H]3C[C@@H](C3(C)C)[C@]2(C)O1] |

-continued
| Compound No. | Compound Structure |
| --- | --- |
| A35 | 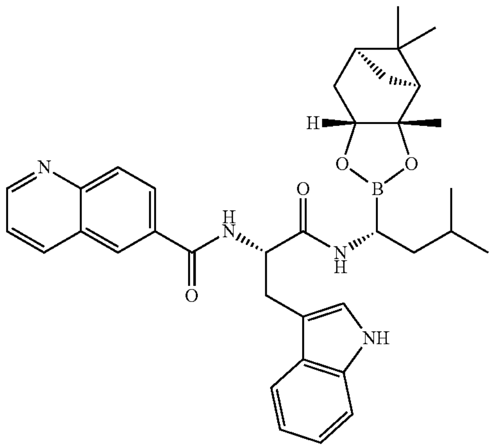 [SMILES: CC(C)C[C@H](NC(=O)[C@H](Cc1c[nH]c2ccccc12)NC(=O)c1ccc2ccccc2c1)B1O[C@@H]2C[C@@H]3C[C@@H](C3(C)C)[C@]2(C)O1] |
| A36 | 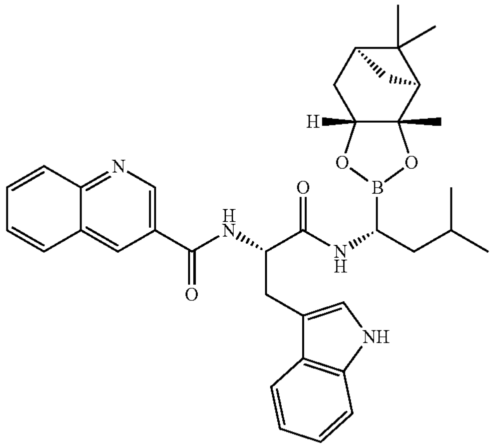 |
| A37 | 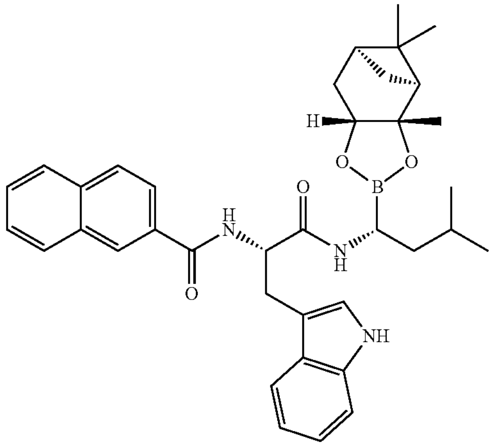 |

-continued
| Compound No. | Compound Structure |
| --- | --- |
| A38 | 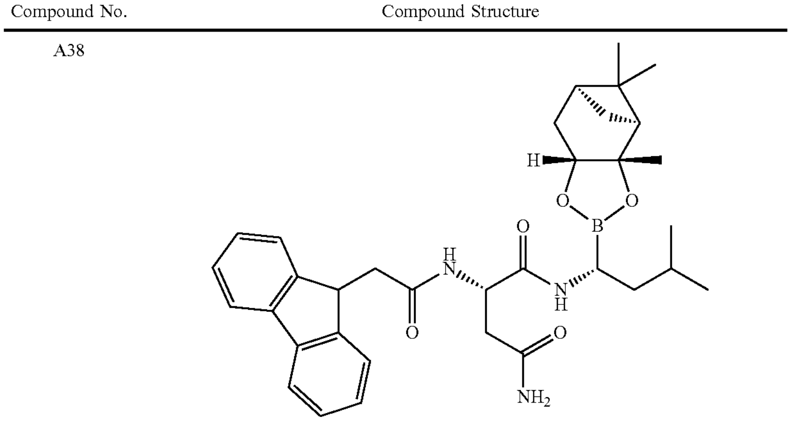 |
| A39 | 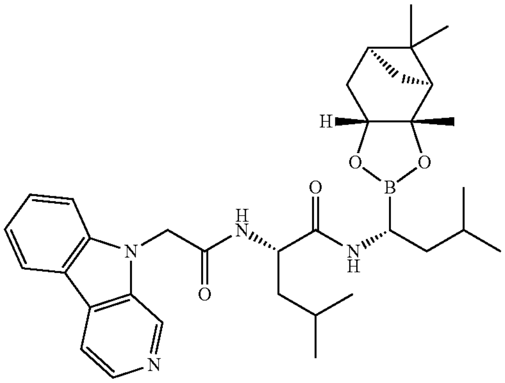 [SMILES: CC(C)C[C@H](NC(=O)[C@H](CC(C)C)NC(=O)Cn1c2ccccc2c2ccncc21)B1O[C@@H]2C[C@@H]3C[C@@H](C3(C)C)[C@]2(C)O1] |
| A40 | 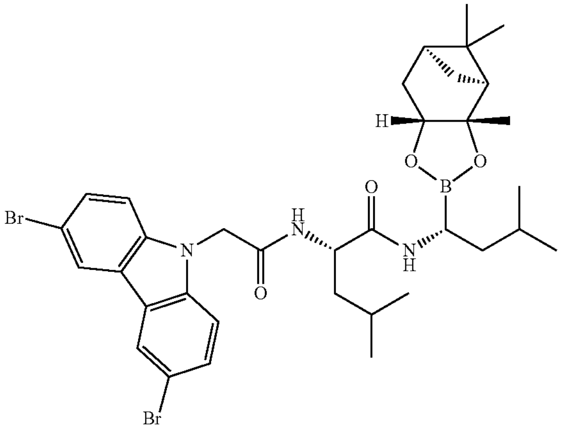 |
| A41 | 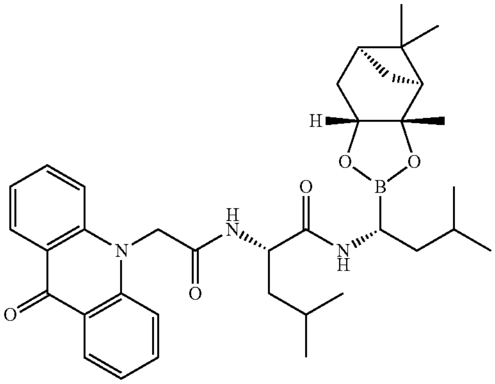 [SMILES: CC(C)C[C@H](NC(=O)[C@H](CC(C)C)NC(=O)Cn1c2ccccc2c(=O)c2ccccc21)B1O[C@@H]2C[C@@H]3C[C@@H](C3(C)C)[C@]2(C)O1] |

-continued
| Compound No. | Compound Structure |
|---|---|
| A42 | 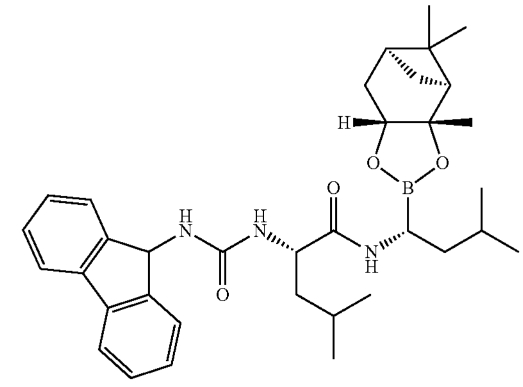 [SMILES: CC(C)C[C@H](NC(=O)[C@H](CC(C)C)NC(=O)NC1c2ccccc2-c2ccccc21)B1O[C@@H]2C[C@@H]3C[C@@H](C3(C)C)[C@]2(C)O1] |
| A43 | 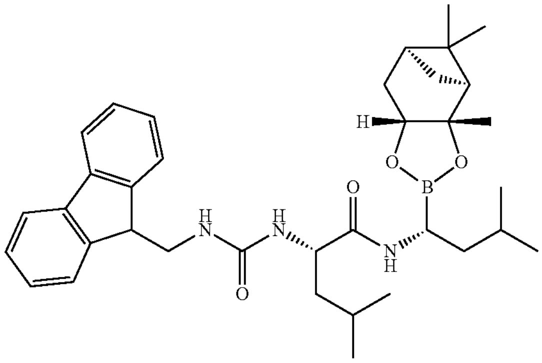 [SMILES: CC(C)C[C@H](NC(=O)[C@H](CC(C)C)NC(=O)NCC1c2ccccc2-c2ccccc21)B1O[C@@H]2C[C@@H]3C[C@@H](C3(C)C)[C@]2(C)O1] |
| A44 | 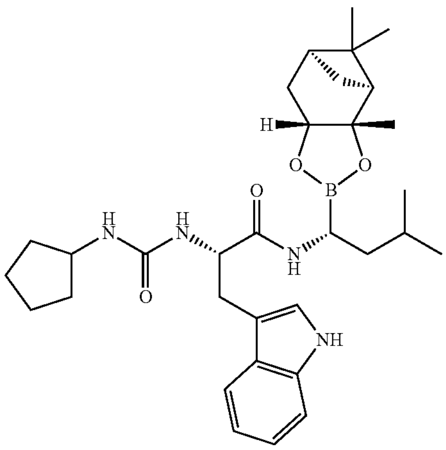 [SMILES: CC(C)C[C@H](NC(=O)[C@H](Cc1c[nH]c2ccccc12)NC(=O)NC1CCCC1)B1O[C@@H]2C[C@@H]3C[C@@H](C3(C)C)[C@]2(C)O1] |

-continued
| Compound No. | Compound Structure |
| --- | --- |
| A45 | 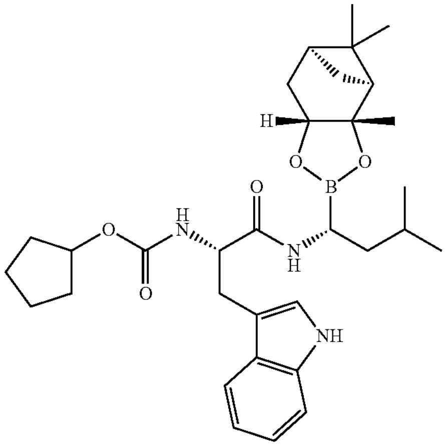 [SMILES: CC(C)C[C@H](NC(=O)[C@H](Cc1c[nH]c2ccccc12)NC(=O)OC1CCCC1)B1O[C@@H]2C[C@@H]3C[C@@H](C3(C)C)[C@]2(C)O1] |
| A46 | 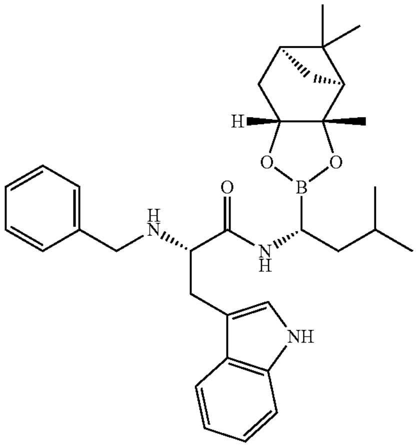 [SMILES: CC(C)C[C@H](NC(=O)[C@H](Cc1c[nH]c2ccccc12)NCc1ccccc1)B1O[C@@H]2C[C@@H]3C[C@@H](C3(C)C)[C@]2(C)O1] |
| A47 | 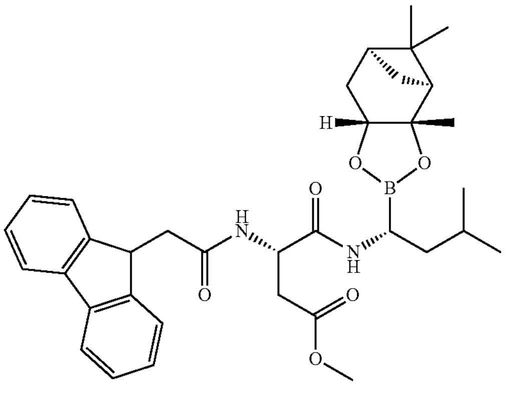 [SMILES: COC(=O)C[C@H](NC(=O)CC1c2ccccc2-c2ccccc21)C(=O)N[C@@H](CC(C)C)B1O[C@@H]2C[C@@H]3C[C@@H](C3(C)C)[C@]2(C)O1] |

-continued
| Compound No. | Compound Structure |
|---|---|
| A48 | 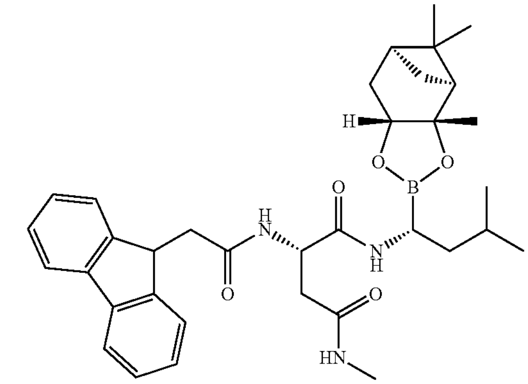 [SMILES: CNC(=O)C[C@H](NC(=O)CC1c2ccccc2-c2ccccc21)C(=O)N[C@@H](CC(C)C)B1O[C@@H]2C[C@@H]3C[C@@H](C3(C)C)[C@]2(C)O1] |
| A49 | 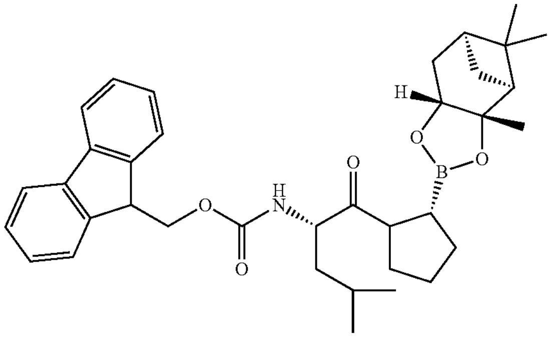 [SMILES: CC(C)C[C@H](NC(=O)OCC1c2ccccc2-c2ccccc21)C(=O)C1CCC[C@H]1B1O[C@@H]2C[C@@H]3C[C@@H](C3(C)C)[C@]2(C)O1] |
| A50 | 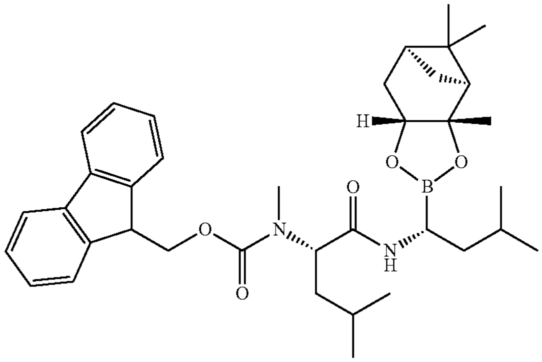 [SMILES: CC(C)C[C@H](NC(=O)[C@H](CC(C)C)N(C)C(=O)OCC1c2ccccc2-c2ccccc21)B1O[C@@H]2C[C@@H]3C[C@@H](C3(C)C)[C@]2(C)O1] |
| A51 | 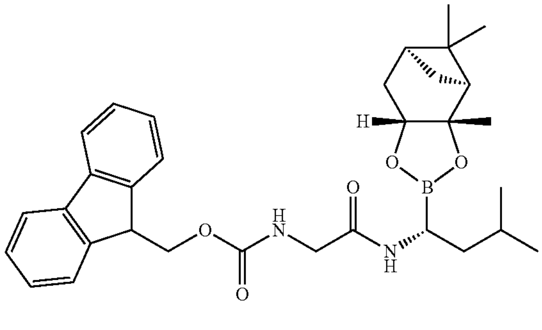 [SMILES: CC(C)C[C@H](NC(=O)CNC(=O)OCC1c2ccccc2-c2ccccc21)B1O[C@@H]2C[C@@H]3C[C@@H](C3(C)C)[C@]2(C)O1] |

-continued
| Compound No. | Compound Structure |
|---|---|
| A52 | 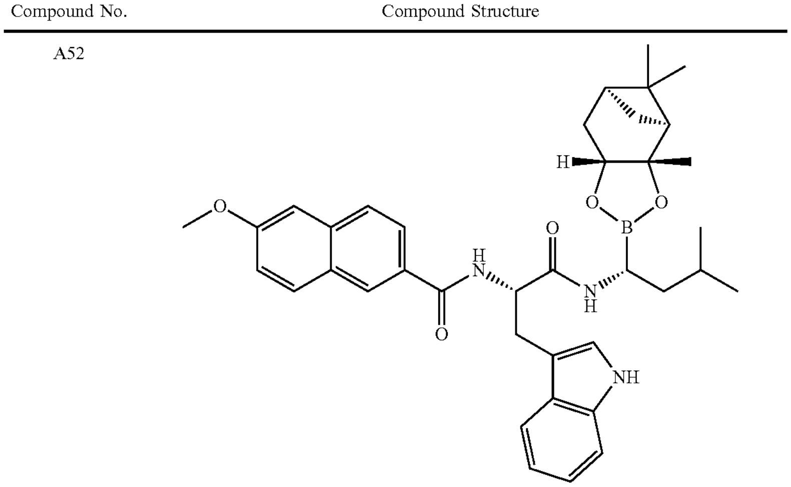 |
| A53 | 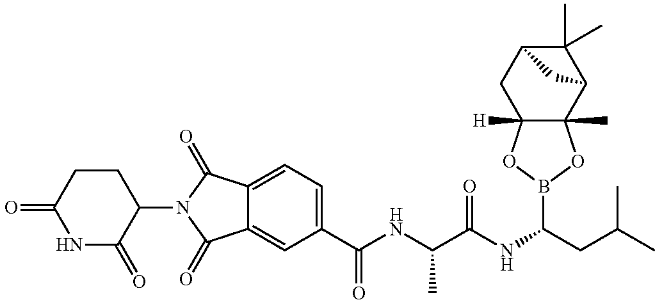 [SMILES: CC(C)C[C@H](NC(=O)[C@H](C)NC(=O)c1ccc2c(c1)C(=O)N(C1CCC(=O)NC1=O)C2=O)B1O[C@@H]2C[C@@H]3C[C@@H](C3(C)C)[C@]2(C)O1] |
| A54 | 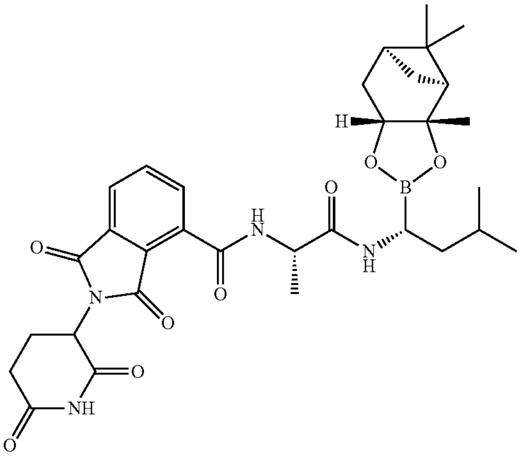 [SMILES: CC(C)C[C@H](NC(=O)[C@H](C)NC(=O)c1cccc2c1C(=O)N(C1CCC(=O)NC1=O)C2=O)B1O[C@@H]2C[C@@H]3C[C@@H](C3(C)C)[C@]2(C)O1] |
| A55 | 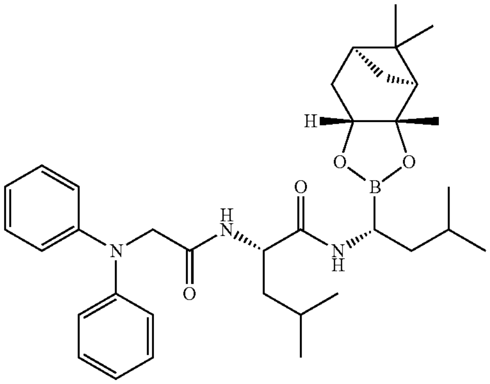 [SMILES: CC(C)C[C@H](NC(=O)[C@H](CC(C)C)NC(=O)CN(c1ccccc1)c1ccccc1)B1O[C@@H]2C[C@@H]3C[C@@H](C3(C)C)[C@]2(C)O1] |

-continued
| Compound No. | Compound Structure |
|---|---|
| A56 | 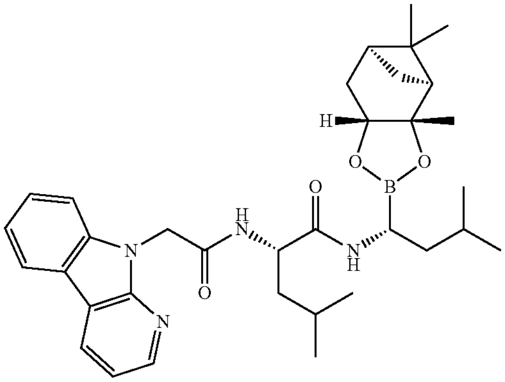 |
| A57 | 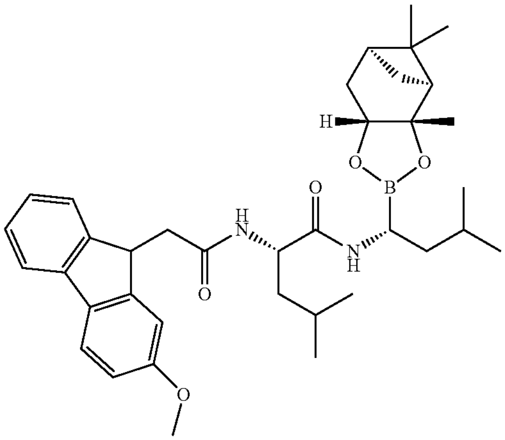 [SMILES: COc1ccc2c(c1)C(CC(=O)N[C@@H](CC(C)C)C(=O)N[C@@H](CC(C)C)B1O[C@@H]3C[C@@H]4C[C@@H](C4(C)C)[C@]3(C)O1)c1ccccc1-2] |
| A58 | 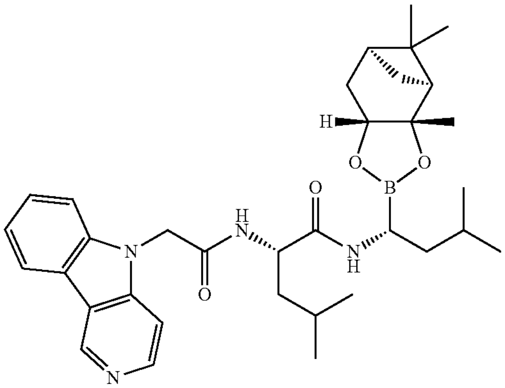 [SMILES: CC(C)C[C@H](NC(=O)[C@H](CC(C)C)NC(=O)Cn1c2ccccc2c2cnccc21)B1O[C@@H]2C[C@@H]3C[C@@H](C3(C)C)[C@]2(C)O1] |

-continued
| Compound No. | Compound Structure |
|---|---|
| A59 | 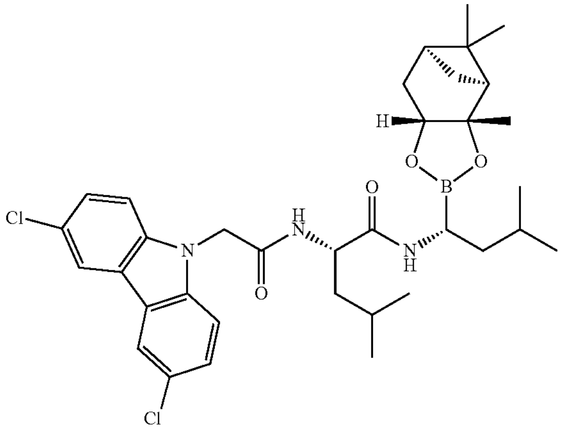 [SMILES: CC(C)C[C@H](NC(=O)[C@H](CC(C)C)NC(=O)Cn1c2ccc(Cl)cc2c2cc(Cl)ccc21)B1O[C@@H]2C[C@@H]3C[C@@H](C3(C)C)[C@]2(C)O1] |
| A60 | 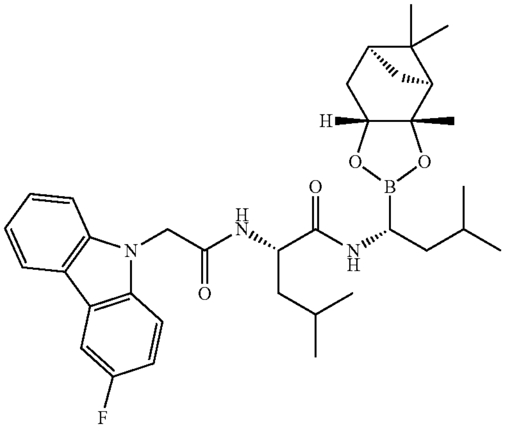 [SMILES: CC(C)C[C@H](NC(=O)[C@H](CC(C)C)NC(=O)Cn1c2ccccc2c2cc(F)ccc21)B1O[C@@H]2C[C@@H]3C[C@@H](C3(C)C)[C@]2(C)O1] |
| A61 | 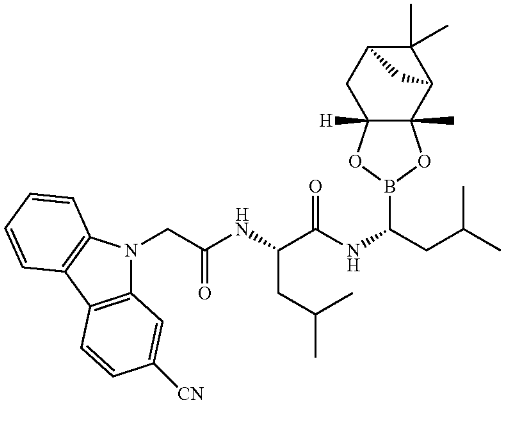 [SMILES: CC(C)C[C@H](NC(=O)[C@H](CC(C)C)NC(=O)Cn1c2ccccc2c2ccc(C#N)cc21)B1O[C@@H]2C[C@@H]3C[C@@H](C3(C)C)[C@]2(C)O1] |

-continued
| Compound No. | Compound Structure |
|---|---|
| A62 | 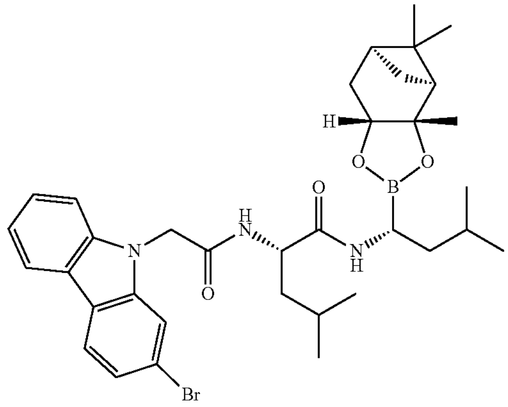 [SMILES: CC(C)C[C@H](NC(=O)[C@H](CC(C)C)NC(=O)Cn1c2ccccc2c2ccc(Br)cc21)B1O[C@@H]2C[C@@H]3C[C@@H](C3(C)C)[C@]2(C)O1] |
| A63 | 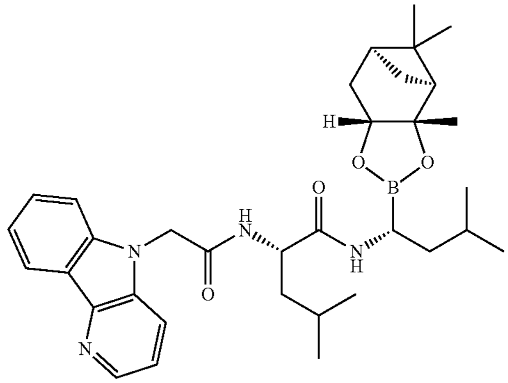 |
| A64 | 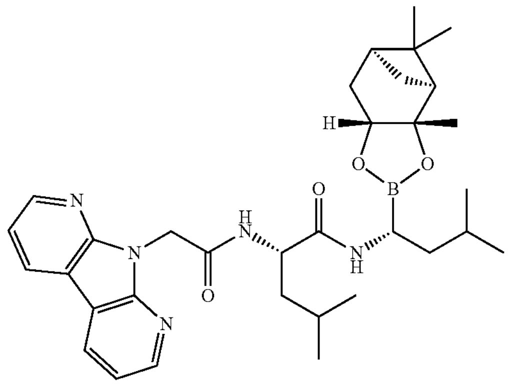 [SMILES: CC(C)C[C@H](NC(=O)[C@H](CC(C)C)NC(=O)Cn1c2ncccc2c2cccnc21)B1O[C@@H]2C[C@@H]3C[C@@H](C3(C)C)[C@]2(C)O1] |

In some embodiments, the compound is a compound represented by formula (III) or a pharmaceutically acceptable salt, solvate, stereoisomer, or prodrug thereof:
(III)
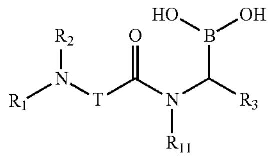
The substituents T, $R_1$, $R_2$, $R_3$ and $R_{11}$ are as defined above.
Specifically, the present disclosure provides the following specific compounds:
| Compound No. | Compound Structure |
|---|---|
| A65 | 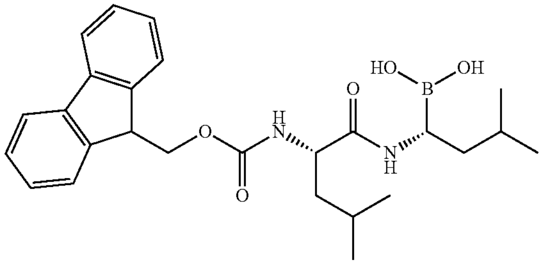 [SMILES: CC(C)C[C@H](NC(=O)[C@H](CC(C)C)NC(=O)OCC1c2ccccc2-c2ccccc21)B(O)O] |
| A66 | 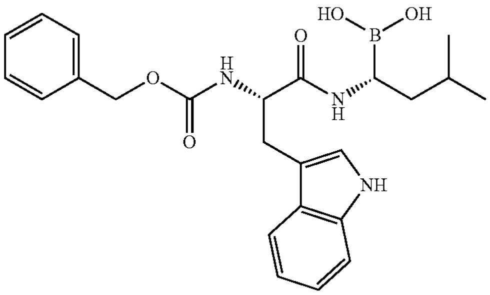 [SMILES: CC(C)C[C@H](NC(=O)[C@H](Cc1c[nH]c2ccccc12)NC(=O)OCc1ccccc1)B(O)O] |
| A67 | 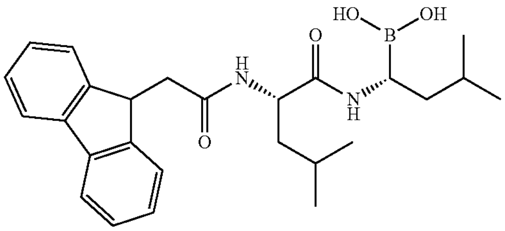 [SMILES: CC(C)C[C@H](NC(=O)[C@H](CC(C)C)NC(=O)CC1c2ccccc2-c2ccccc21)B(O)O] |
| A68 | 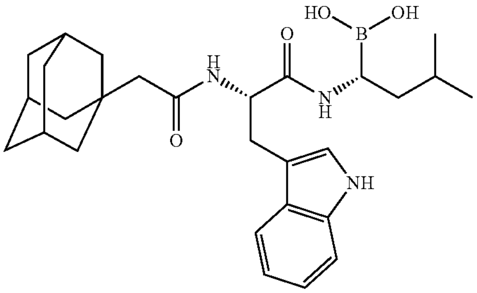 [SMILES: CC(C)C[C@H](NC(=O)[C@H](Cc1c[nH]c2ccccc12)NC(=O)CC12CC3CC(CC(C3)C1)C2)B(O)O] |

-continued
| Compound No. | Compound Structure |
|---|---|
| A69 | 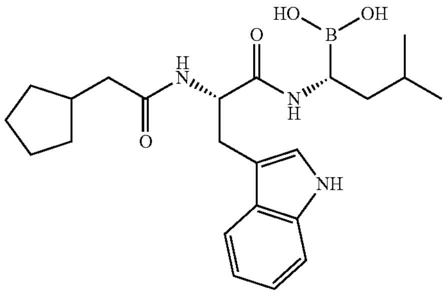 [SMILES: CC(C)C[C@H](NC(=O)[C@H](Cc1c[nH]c2ccccc12)NC(=O)CC1CCCC1)B(O)O] |
| A70 | 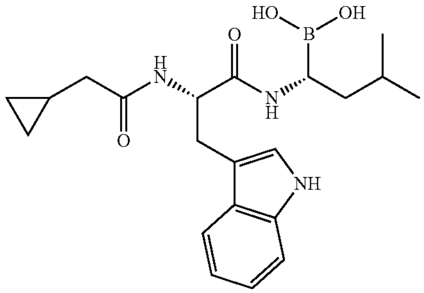 [SMILES: CC(C)C[C@H](NC(=O)[C@H](Cc1c[nH]c2ccccc12)NC(=O)CC1CC1)B(O)O] |
| A71 | 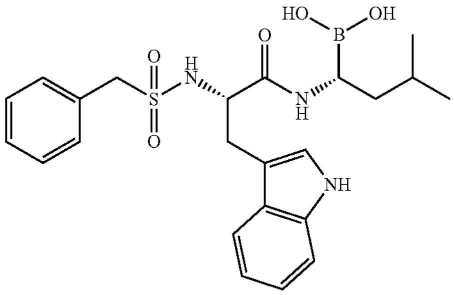 [SMILES: CC(C)C[C@H](NC(=O)[C@H](Cc1c[nH]c2ccccc12)NS(=O)(=O)Cc1ccccc1)B(O)O] |
| A72 | 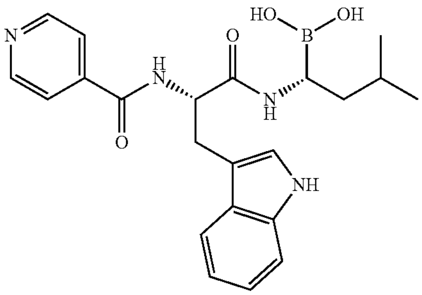 [SMILES: CC(C)C[C@H](NC(=O)[C@H](Cc1c[nH]c2ccccc12)NC(=O)c1ccncc1)B(O)O] |
| A73 | 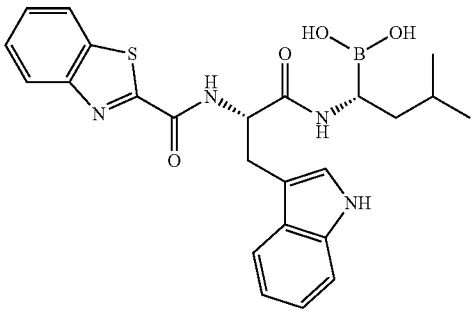 [SMILES: CC(C)C[C@H](NC(=O)[C@H](Cc1c[nH]c2ccccc12)NC(=O)c1nc2ccccc2s1)B(O)O] |

-continued
| Compound No. | Compound Structure |
|---|---|
| A74 | 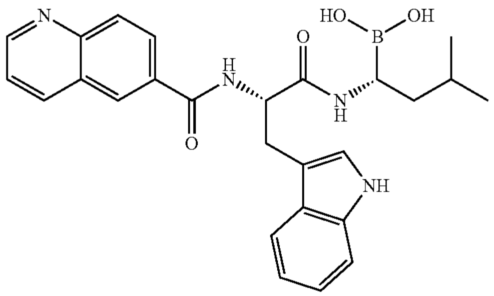 |
| A75 | 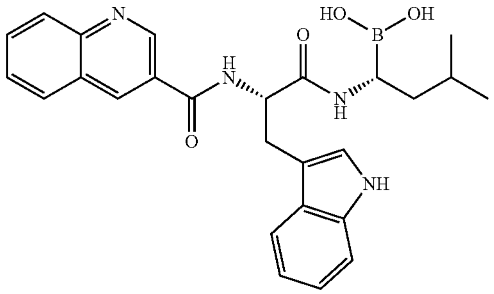 [SMILES: CC(C)C[C@H](NC(=O)[C@H](Cc1c[nH]c2ccccc12)NC(=O)c1cnc2ccccc2c1)B(O)O] |
| A76 | 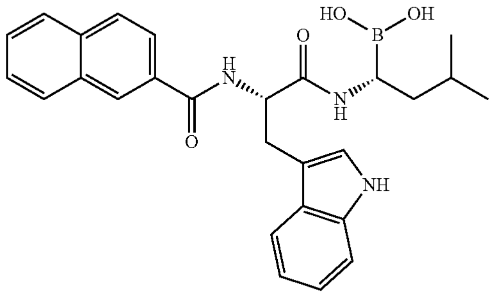 [SMILES: CC(C)C[C@H](NC(=O)[C@H](Cc1c[nH]c2ccccc12)NC(=O)c1ccc2ccccc2c1)B(O)O] |
| A77 | 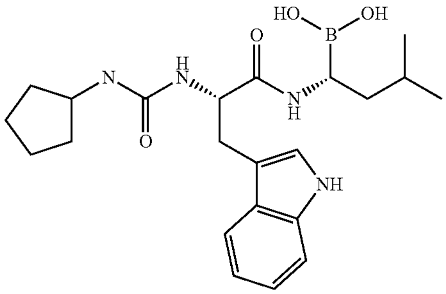 [SMILES: CC(C)C[C@H](NC(=O)[C@H](Cc1c[nH]c2ccccc12)NC(=O)NC1CCCC1)B(O)O] |
| A78 | 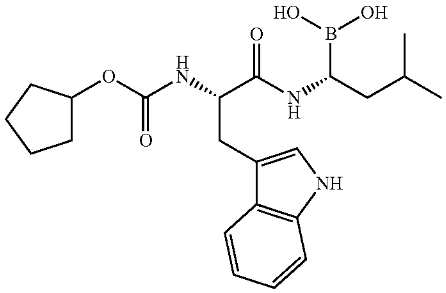 [SMILES: CC(C)C[C@H](NC(=O)[C@H](Cc1c[nH]c2ccccc12)NC(=O)OC1CCCC1)B(O)O] |

-continued
| Compound No. | Compound Structure |
|---|---|
| A79 | 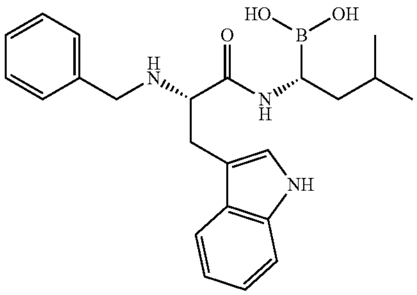 [SMILES: CC(C)C[C@H](NC(=O)[C@H](Cc1c[nH]c2ccccc12)NCc1ccccc1)B(O)O] |
| A80 | 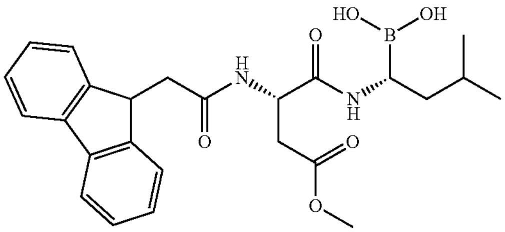 [SMILES: COC(=O)C[C@H](NC(=O)CC1c2ccccc2-c2ccccc21)C(=O)N[C@@H](CC(C)C)B(O)O] |
| A81 | 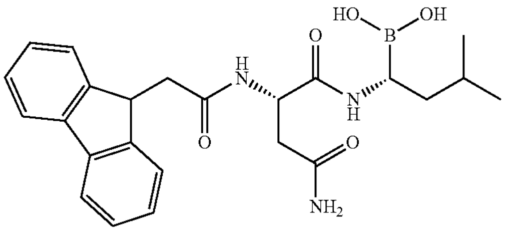 [SMILES: CC(C)C[C@H](NC(=O)[C@H](CC(N)=O)NC(=O)CC1c2ccccc2-c2ccccc21)B(O)O] |
| A82 | 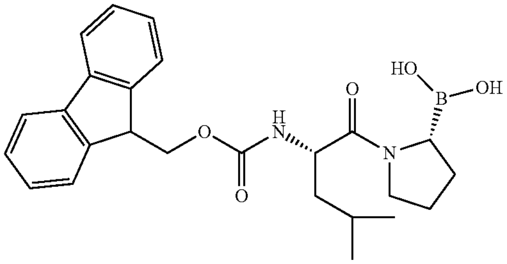 [SMILES: CC(C)C[C@H](NC(=O)OCC1c2ccccc2-c2ccccc21)C(=O)N1CCC[C@H]1B(O)O] |
| A83 | 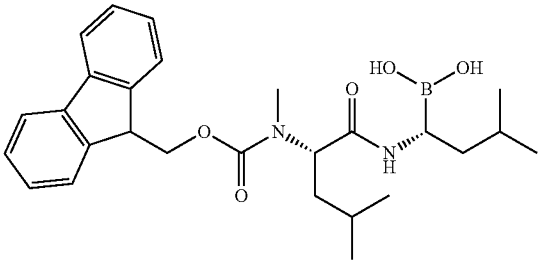 [SMILES: CC(C)C[C@H](NC(=O)[C@H](CC(C)C)N(C)C(=O)OCC1c2ccccc2-c2ccccc21)B(O)O] |
| A84 | 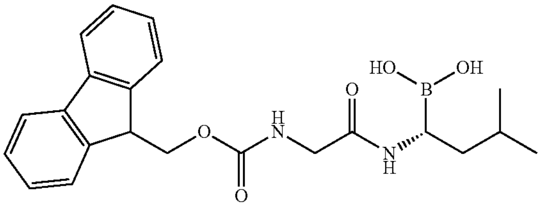 [SMILES: CC(C)C[C@H](NC(=O)CNC(=O)OCC1c2ccccc2-c2ccccc21)B(O)O] |

-continued
| Compound No. | Compound Structure |
| --- | --- |
| A85 | 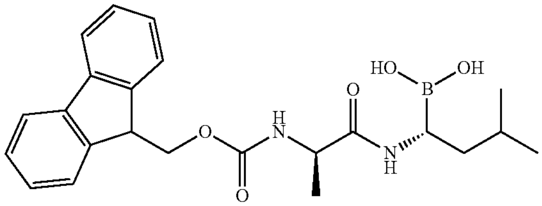 [SMILES: CC(C)C[C@H](NC(=O)[C@@H](C)NC(=O)OCC1c2ccccc2-c2ccccc21)B(O)O] |
| A86 | 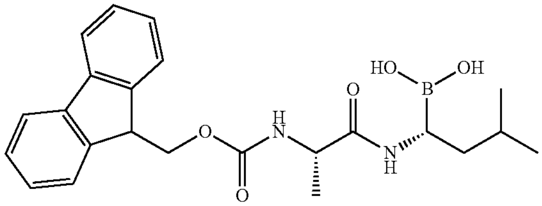 [SMILES: CC(C)C[C@H](NC(=O)[C@H](C)NC(=O)OCC1c2ccccc2-c2ccccc21)B(O)O] |
| A87 | 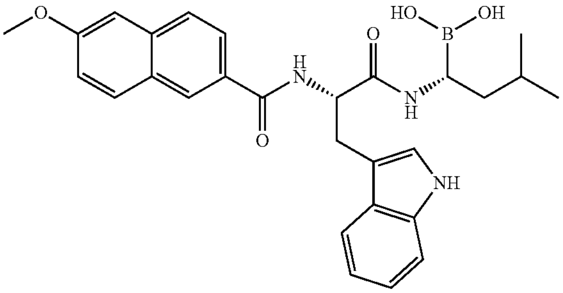 [SMILES: COc1ccc2cc(C(=O)N[C@@H](Cc3c[nH]c4ccccc34)C(=O)N[C@@H](CC(C)C)B(O)O)ccc2c1] |
| A88 | 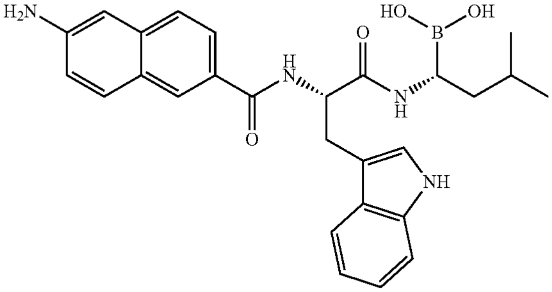 [SMILES: CC(C)C[C@H](NC(=O)[C@H](Cc1c[nH]c2ccccc12)NC(=O)c1ccc2cc(N)ccc2c1)B(O)O] |
| A89 | 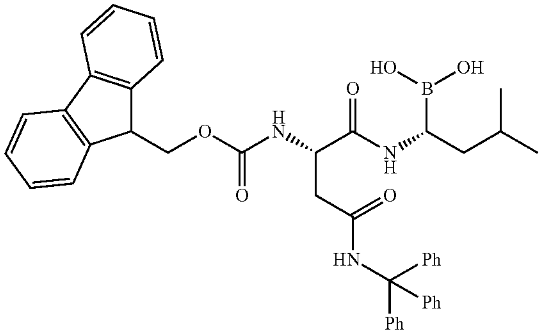 [SMILES: CC(C)C[C@H](NC(=O)[C@H](CC(=O)NC(c1ccccc1)(c1ccccc1)c1ccccc1)NC(=O)OCC1c2ccccc2-c2ccccc21)B(O)O] |
| A90 | 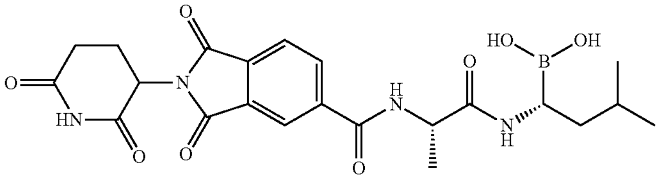 [SMILES: CC(C)C[C@H](NC(=O)[C@H](C)NC(=O)c1ccc2c(c1)C(=O)N(C1CCC(=O)NC1=O)C2=O)B(O)O] |

-continued
| Compound No. | Compound Structure |
|---|---|
| A91 | 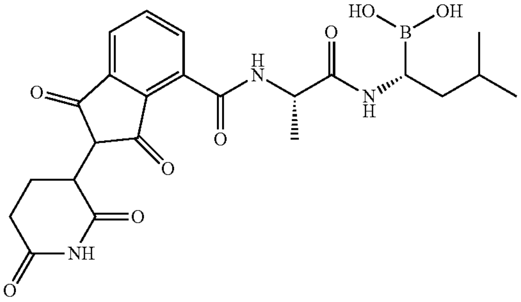 [SMILES: CC(C)C[C@H](NC(=O)[C@H](C)NC(=O)c1cccc2c1C(=O)C(C1CCC(=O)NC1=O)C2=O)B(O)O] |
| A92 | 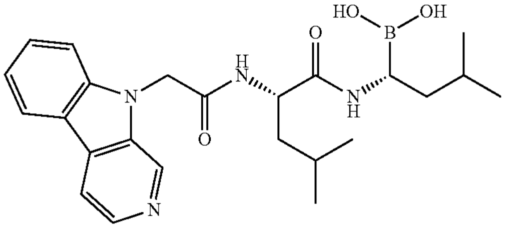 [SMILES: CC(C)C[C@H](NC(=O)[C@H](CC(C)C)NC(=O)Cn1c2ccccc2c2ccncc21)B(O)O] |
| A93 | 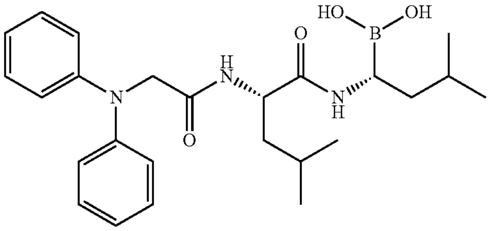 [SMILES: CC(C)C[C@H](NC(=O)[C@H](CC(C)C)NC(=O)CN(c1ccccc1)c1ccccc1)B(O)O] |
| A94 | 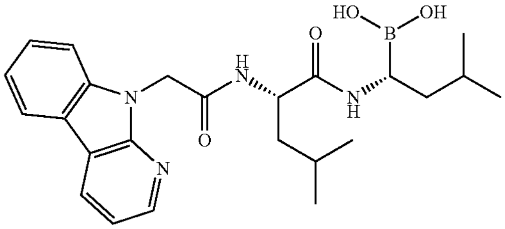 |
| A95 | 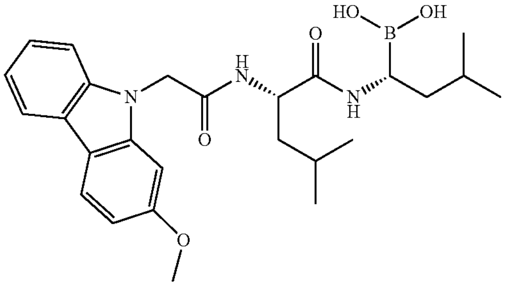 [SMILES: COc1ccc2c3ccccc3n(CC(=O)N[C@@H](CC(C)C)C(=O)N[C@@H](CC(C)C)B(O)O)c2c1] |
| A96 | 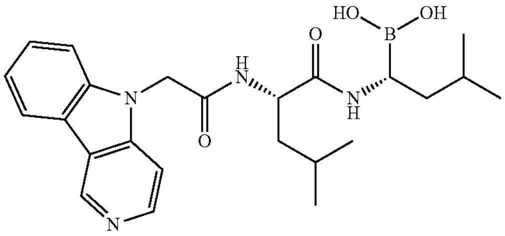 [SMILES: CC(C)C[C@H](NC(=O)[C@H](CC(C)C)NC(=O)Cn1c2ccccc2c2cnccc21)B(O)O] |

-continued
| Compound No. | Compound Structure |
|---|---|
| A97 | 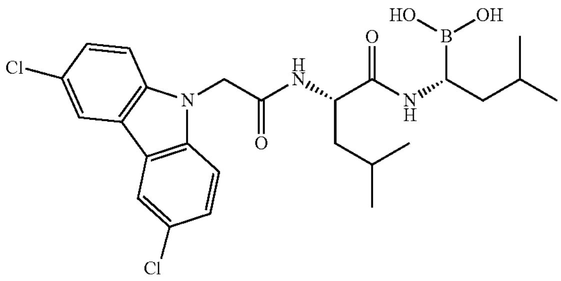 [SMILES: CC(C)C[C@H](NC(=O)[C@H](CC(C)C)NC(=O)Cn1c2ccc(Cl)cc2c2cc(Cl)ccc21)B(O)O] |
| A98 | 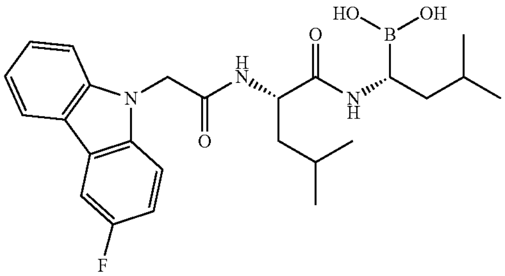 [SMILES: CC(C)C[C@H](NC(=O)[C@H](CC(C)C)NC(=O)Cn1c2ccccc2c2cc(F)ccc21)B(O)O] |
| A99 | 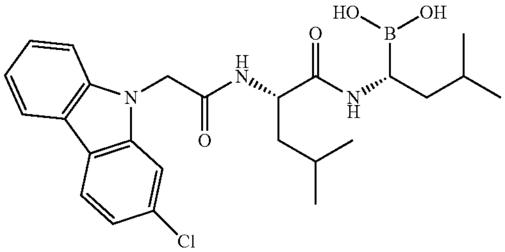 [SMILES: CC(C)C[C@H](NC(=O)[C@H](CC(C)C)NC(=O)Cn1c2ccccc2c2ccc(Cl)cc21)B(O)O] |
| A100 | 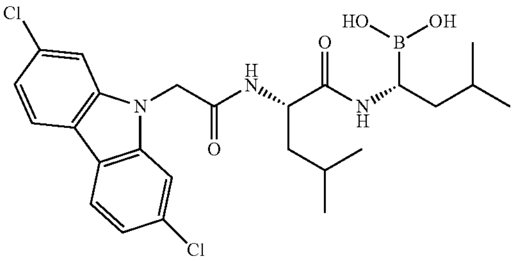 [SMILES: CC(C)C[C@H](NC(=O)[C@H](CC(C)C)NC(=O)Cn1c2cc(Cl)ccc2c2ccc(Cl)cc21)B(O)O] |
| A101 | 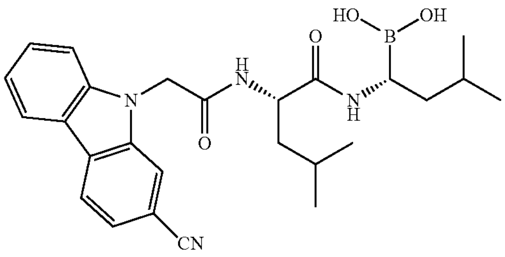 [SMILES: CC(C)C[C@H](NC(=O)[C@H](CC(C)C)NC(=O)Cn1c2ccccc2c2ccc(C#N)cc21)B(O)O] |

-continued
| Compound No. | Compound Structure |
| --- | --- |
| A102 | 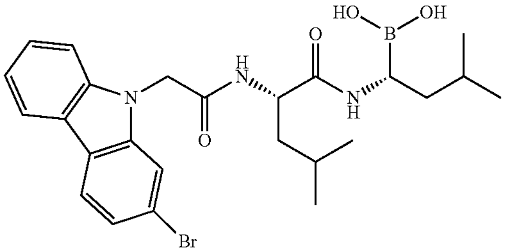 |
| A103 | 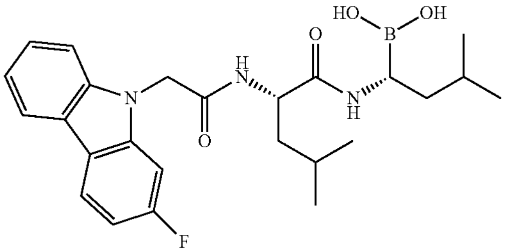 [SMILES: CC(C)C[C@H](NC(=O)[C@H](CC(C)C)NC(=O)Cn1c2ccccc2c2ccc(F)cc21)B(O)O] |
| A104 | 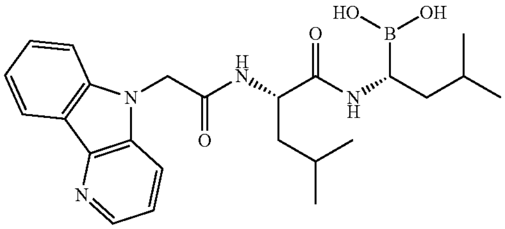 [SMILES: CC(C)C[C@H](NC(=O)[C@H](CC(C)C)NC(=O)Cn1c2ccccc2c2ncccc21)B(O)O] |
| A105 | 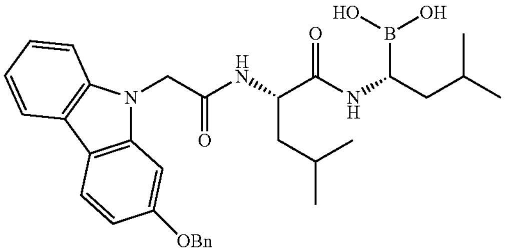 [SMILES: CC(C)C[C@H](NC(=O)[C@H](CC(C)C)NC(=O)Cn1c2ccccc2c2ccc(OCc3ccccc3)cc21)B(O)O] |
| A106 | 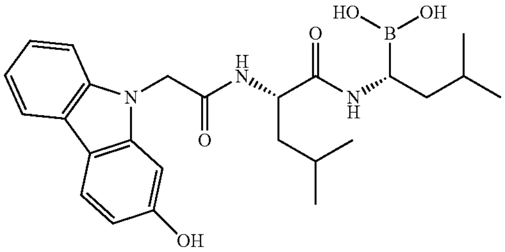 [SMILES: CC(C)C[C@H](NC(=O)[C@H](CC(C)C)NC(=O)Cn1c2ccccc2c2ccc(O)cc21)B(O)O] |
| A107 | 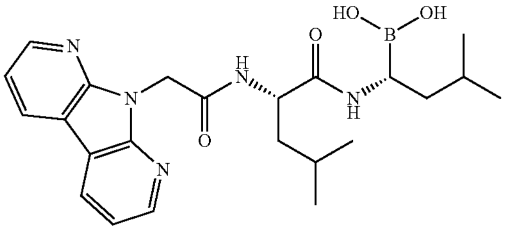 [SMILES: CC(C)C[C@H](NC(=O)[C@H](CC(C)C)NC(=O)Cn1c2ncccc2c2cccnc21)B(O)O] |

The pharmaceutically acceptable salts of the present disclosure include hydrochloride, phosphate, hydrogen phosphate, dihydrogen phosphate, sulfate, nitrate, bicarbonate, carbonate, glutarate, hydrobromide, acetate, citrate, lactate, maleate, benzoate, methanesulfonate, oxalate, benzenesulfonate, p-toluenesulfonate, tartrate, malate, succinate, ascorbate, gluconate, lactate, and the like.

The solvate of the present disclosure is selected from hemihydrate, monohydrate, dihydrate and the like; the stereoisomer is selected from enantiomer, diastereomer, and the like.

Another object of the present disclosure is to provide a pharmaceutical composition comprising a pharmaceutically acceptable carrier and the above-mentioned compound or the pharmaceutically acceptable salt, the solvate, the stereoisomer or the prodrug thereof.

Another object of the present disclosure is to provide the use of the compound of the present disclosure or the pharmaceutically acceptable salt, the solvate, the stereoisomer or the prodrug thereof in the preparation of c-Myc protein inhibitors.

Another object of the present disclosure is to provide the use of the compound of the present disclosure or the pharmaceutically acceptable salt, the solvate, the stereoisomer or the prodrug thereof in the preparation of a medicament for treating diseases related to c-Myc protein disorders.

Preferably, the c-Myc protein disorder is selected from c-Myc protein overexpression or enhanced protein stability.

Preferably, the diseases related to c-Myc protein disorders are selected from cancers, cardiovascular and cerebrovascular diseases, viral infection-related diseases and the like.

Preferably, the cancer is selected from liver cancer, lung cancer, kidney cancer, pancreatic cancer, oral cancer, gastric cancer, esophageal cancer, laryngeal cancer, nasopharyngeal cancer, skin cancer, breast cancer, colon cancer, rectal cancer, cervical cancer, ovarian cancer, prostate cancer, brain cancer, nerve cancer, granulocytic leukemia, rhabdomyosarcoma, osteosarcoma, chondrosarcoma, leukemia, lymphoma and so on; the viral infection-related diseases are selected from HIV, hepatitis B, hepatitis C, hepatitis A, influenza, Japanese encephalitis, herpes and so on.

The beneficial effects of the present disclosure

The compound provided by the present disclosure has excellent c-Myc protein inhibitory effect, therefore it can be used for the prevention and treatment of c-Myc related diseases, such as cancers, cardiovascular and cerebrovascular diseases, viral infections and other diseases. The synthesis method of the compound is simple, and the inhibitory effect of c-Myc protein is effective.

DETAILED DESCRIPTION

Figure 1:
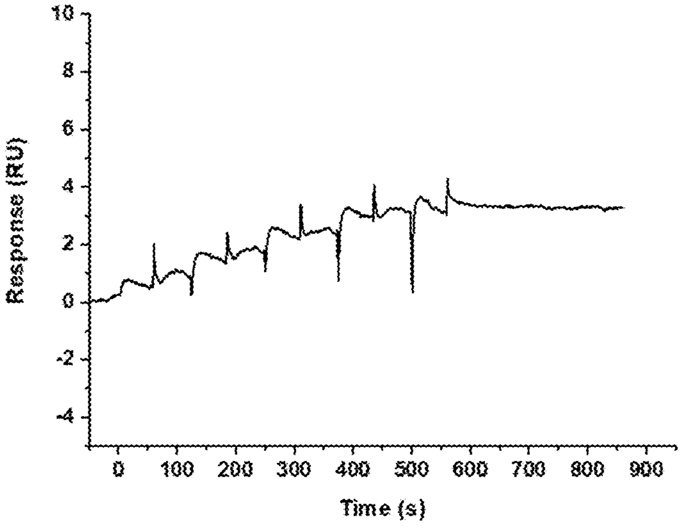
FIG. 1: Single-cycle binding kinetics curve of A5 and c-Myc peptide LE40.
Figure 2:
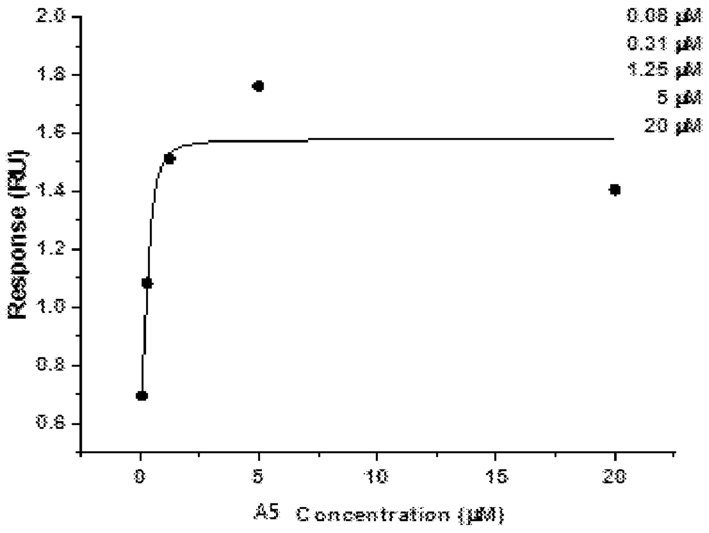
FIG. 2: The binding $K_D$ of A5 and c-Myc peptide LE40 is 0.16 μM.
Figure 3:
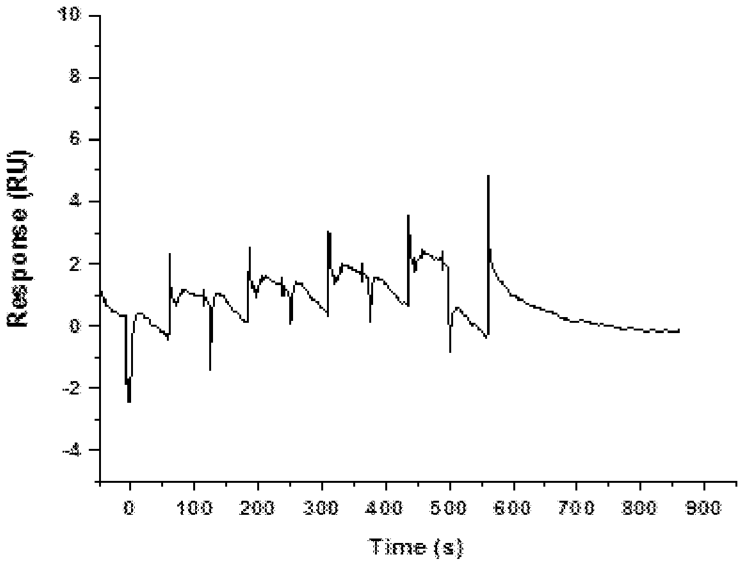
FIG. 3: Single-cycle binding kinetic curve of A5 and c-Myc peptide LE40 (S373A), no obvious binding.
Figure 4:
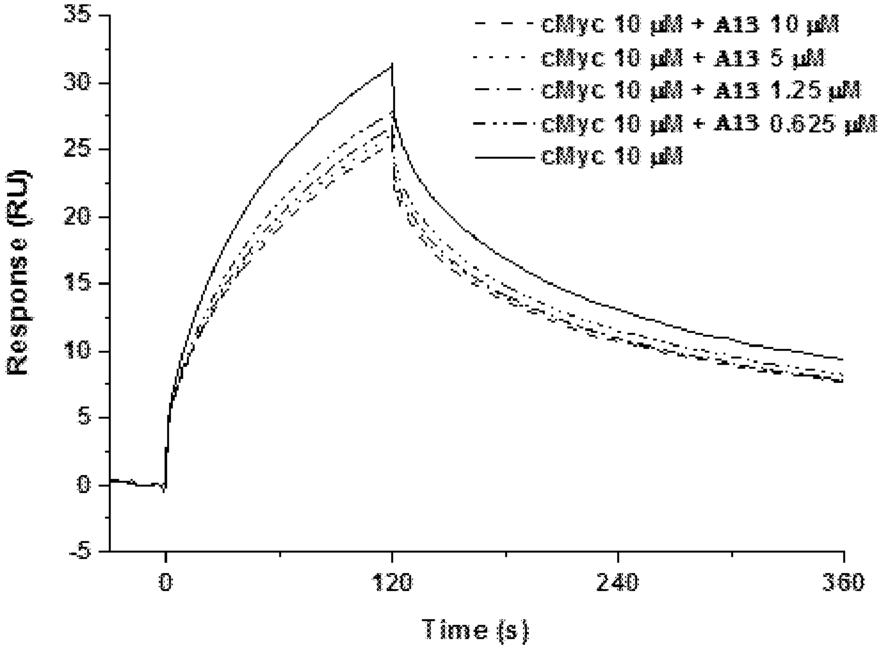
FIG. 4: Compound A13 can compete for the binding of c-Myc and Max.
Figure 5:
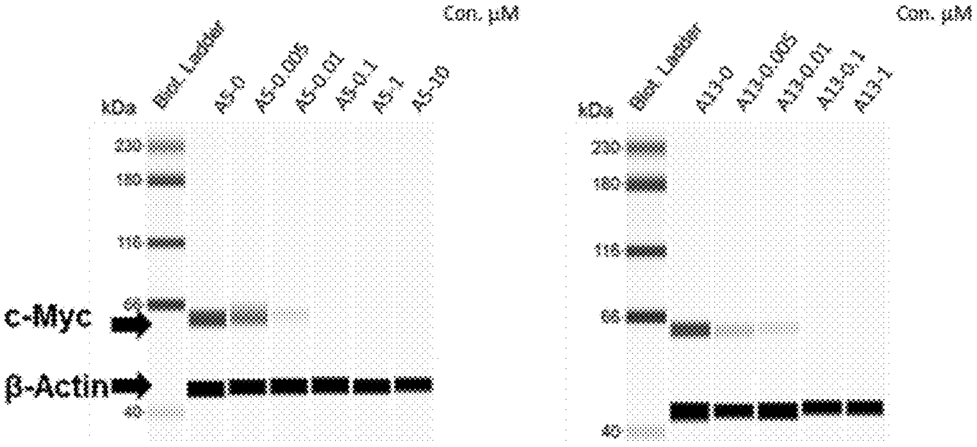
FIG. 5: A5 and A13 promote the degradation of c-Myc protein.
Figure 6:
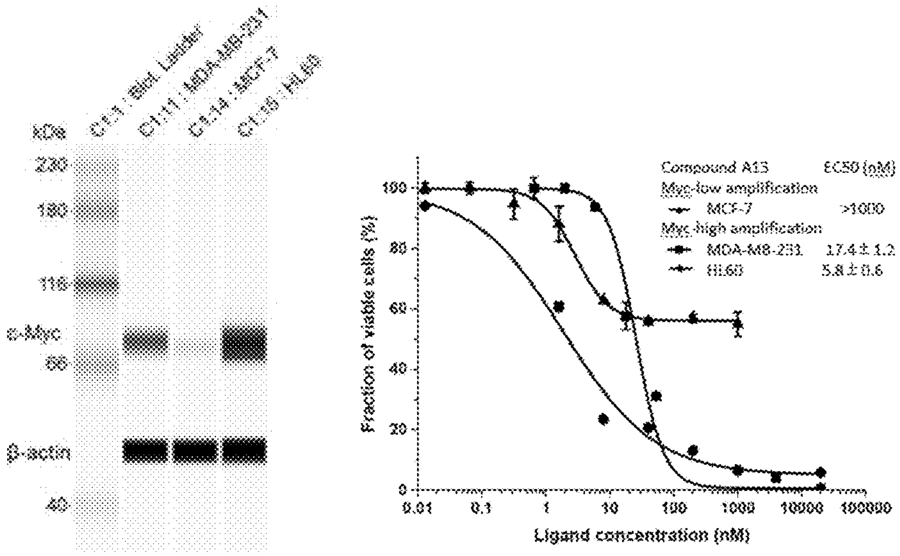
FIG. 6: A13 selectively inhibits tumor cells with high expression of c-Myc.

The present disclosure will be exemplified below in combination with the accompanying drawings and further detailed description. It should be pointed out that the following description is only examples of the technical solutions claimed by the present disclosure, and does not limit these technical solutions in any way. The protection scope of the present disclosure is subject to the content recorded in the appended claims.

Example 1

Compound A1

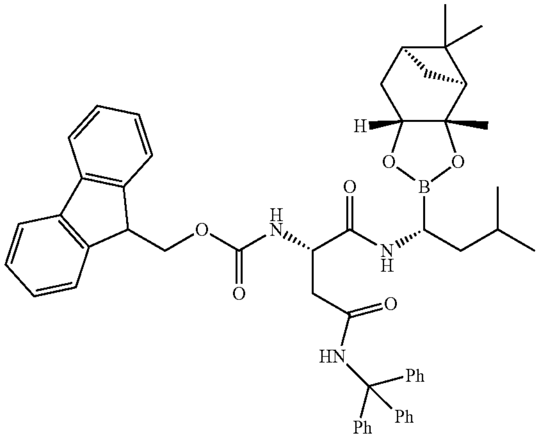

Compound A1 was synthesized as follows:

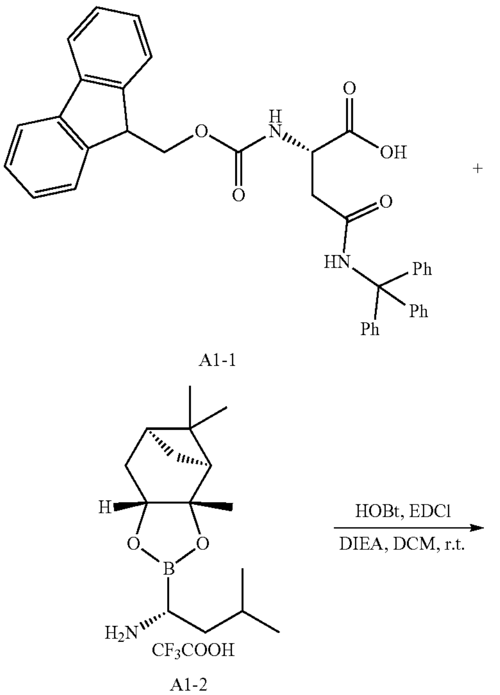

A1-1

A1-2

-continued

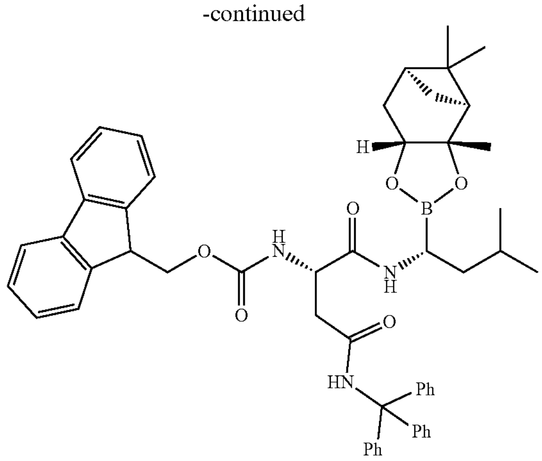

A1

Compound A1-1 (2.98 g, 5 mmol) was dissolved in dichloromethane (DCM) (150 mL), and 1-hydroxybenzotriazole (HOBt) (810 mg, 6 mmol) and 1-(3-dimethylamino-propyl)-3-ethylcarbodiimide hydrochloride (EDCI) (1.15 g, 6 mmol) were added under ice bath. After reacting for 30 min, A1-2 (1.90 g, 5 mmol) and N,N-diisopropylethylamine (DIEA) (1.3 mL, 7.4 mmol) were added and reacted at room temperature for 2 hours. Water was added, and the mixture was extracted with DCM (100 mL*3). The organic phases were combined. After the solvent was spin-dried, the crude product was purified by medium pressure preparative liquid chromatography to obtain a white solid compound A1 (280 mg, yield 6.8%).

$^1$H NMR (400 MHz, DMSO) δ 8.87 (s, 1H), 8.60 (s, 1H), 7.90 (d, J=7.6 Hz, 2H), 7.78-7.66 (m, 3H), 7.47-7.37 (m, 2H), 7.33 (t, J=7.4 Hz, 1H), 7.20 (dt, J=13.0, 6.7 Hz, 15H), 4.44 (d, J=22.6 Hz, 1H), 4.34 (d, J=16.0 Hz, 1H), 4.29-4.15 (m, 2H), 4.08 (d, J=8.4 Hz, 1H), 2.72 (t, J=14.8 Hz, 1H), 2.58 (d, J=6.8 Hz, 1H), 2.46 (s, 1H), 2.24-2.14 (m, 1H), 2.05-1.96 (m, 1H), 1.86-1.79 (m, 1H), 1.80-1.75 (m, 1H), 1.70-1.61 (m, 2H), 1.36-1.20 (m, 9H), 0.84-0.74 (m, 9H).

ESI-MS $(M+H)^+$: 844.

The synthesis method of compound A2-A10 is the same as that of A1, except that the Fmoc protected L-asparagine (NH-Trt) was replaced with the corresponding Fmoc protected amino acid.

Example 2

Compound A2

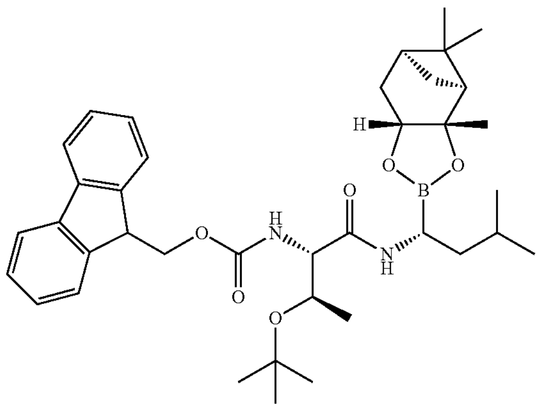

$^1$H NMR (400 MHz, DMSO) δ 8.67 (s, 1H), 7.88 (d, J=7.3 Hz, 2H), 7.73 (t, J=6.4 Hz, 2H), 7.41 (t, J=7.1 Hz, 2H), 7.31 (t, J=7.2 Hz, 2H), 7.06 (d, J=9.3 Hz, 1H), 4.48-4.28 (m, 2H), 4.24 (d, J=6.2 Hz, 1H), 4.12 (dd, J=18.6, 8.5 Hz, 2H), 3.85 (t, J=13.9 Hz, 1H), 2.57 (d, J=21.7 Hz, 1H), 2.18 (dd, J=24.5, 14.7 Hz, 1H), 2.01 (s, 1H), 1.81 (d, J=24.2 Hz, 2H), 1.73-1.57 (m, 2H), 1.34 (d, J=9.4 Hz, 2H), 1.26 (s, 3H), 1.21 (s, 3H), 1.10 (s, 9H), 1.03 (d, J=5.7 Hz, 3H), 0.90-0.75 (m, 9H).

ESI-MS $(M+Na)^+$: 667.

Example 3

Compound A3

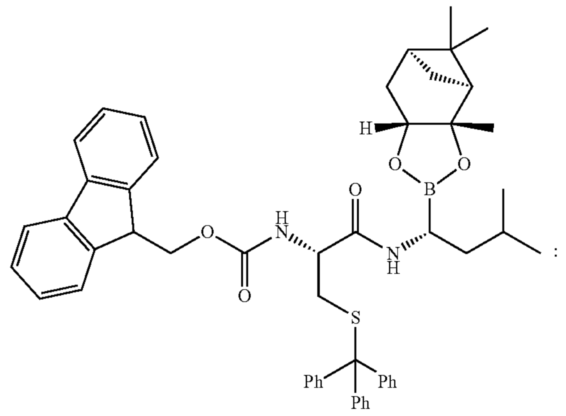

$^1$H NMR (400 MHz, DMSO) δ 8.53 (s, 1H), 7.89 (d, J=7.6 Hz, 2H), 7.72 (d, J=7.7 Hz, 3H), 7.40 (t, J=7.4 Hz, 2H), 7.35-7.29 (m, 12H), 7.25 (dt, J=12.0, 4.6 Hz, 5H), 4.33-4.16 (m, 3H), 4.16-4.00 (m, 2H), 2.61 (t, J=9.3 Hz, 1H), 2.39 (t, J=12.8 Hz, 1H), 2.30 (dd, J=11.8, 5.5 Hz, 1H), 2.17 (dd, J=17.7, 13.3 Hz, 1H), 1.98 (dd, J=13.2, 8.4 Hz, 1H), 1.83-1.71 (m, 2H), 1.66-1.53 (m, 2H), 1.33 (dd, J=29.0, 15.1 Hz, 3H), 1.17 (t, J=13.8 Hz, 6H), 0.86-0.70 (m, 9H).

ESI-MS (M+Na)+: 855.

Example 4

Compound A4

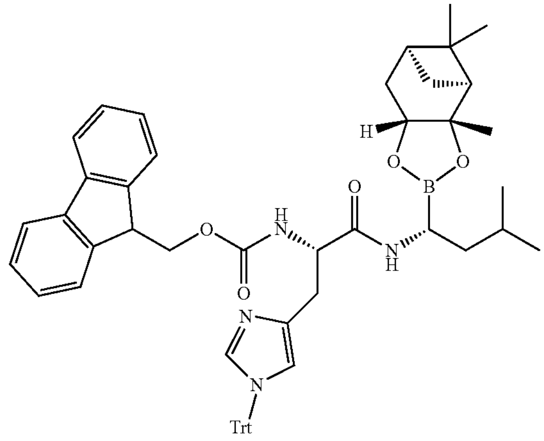

$^1$H NMR (400 MHz, DMSO) δ 8.94 (s, 1H), 7.88 (d, J=7.3 Hz, 2H), 7.66 (d, J=6.0 Hz, 2H), 7.57 (d, J=8.3 Hz, 1H), 7.40-7.38 (m, 2H), 7.36-7.22 (m, 12H), 7.05 (d, J=6.6 Hz,

6H), 6.77 (s, 1H), 4.43 (t, J=10.3 Hz, 1H), 4.29-4.09 (m, 3H), 4.01 (d, J=7.8 Hz, 1H), 2.99-2.74 (m, 2H), 2.66-2.53 (m, 1H), 2.17-2.12 (m, 1H), 1.96 (s, 1H), 1.82-1.51 (m, 4H), 1.41-1.04 (m, 9H), 0.85-0.76 (m, 9H).

ESI-MS $(M+H)^+$: 867.

Example 5

Compound A5

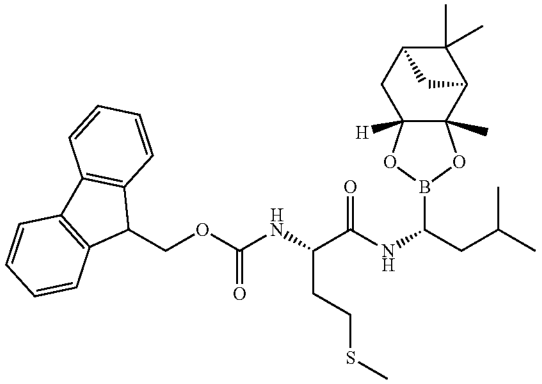

$^1$H NMR (400 MHz, DMSO) δ 8.79 (s, 1H), 7.89 (d, J=7.5 Hz, 2H), 7.71 (t, J=7.8 Hz, 2H), 7.64 (d, J=8.1 Hz, 1H), 7.42 (t, J=7.4 Hz, 2H), 7.32 (dd, J=11.7, 7.2 Hz, 2H), 4.32-4.14 (m, 4H), 4.10 (t, J=8.3 Hz, 1H), 2.67-2.53 (m, 1H), 2.48-2.40 (m, 2H), 2.22-2.18 (m, 1H), 2.08-2.00 (m, 4H), 1.90-1.74 (m, 4H), 1.70-1.60 (m, 2H), 1.35-1.12 (m, 9H), 0.90-0.72 (m, 9H).

ESI-MS $(M+H)^+$: 619.

Example 6

Compound A6

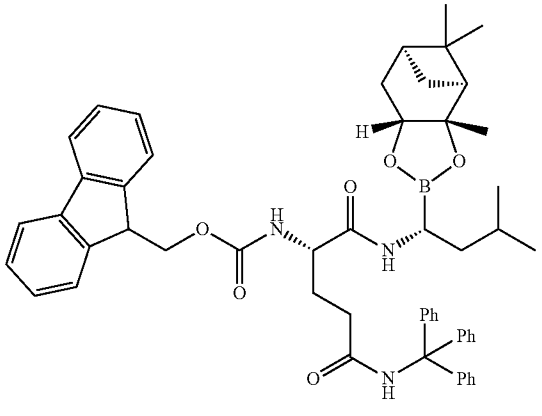

$^1$H NMR (400 MHz, DMSO) δ 8.78 (s, 1H), 8.57 (s, 1H), 7.89 (d, J=7.2 Hz, 2H), 7.71 (d, J=7.1 Hz, 2H), 7.53 (d, J=12.7 Hz, 1H), 7.42 (t, J=7.2 Hz, 2H), 7.37-7.30 (m, 2H), 7.25-7.24 (m, 6H), 7.21-7.15 (m, 9H), 4.30-4.27 (m, 2H), 4.22 (d, J=12.7 Hz, 1H), 4.11-4.04 (m, 2H), 2.20-2.14 (m, 1H), 2.01-1.97 (m, 1H), 1.83-1.76 (m, 2H), 1.77-1.73 (m, 1H), 1.69-1.58 (m, 2H), 1.36-1.16 (m, 10H), 0.85-0.77 (m, 9H).

ESI-MS $(M+H)^+$: 858.

Example 7

Compound A7

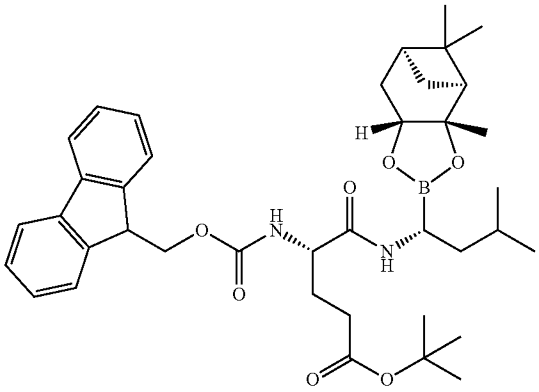

$^1$H NMR (400 MHz, DMSO) δ 8.72 (s, 1H), 7.89 (d, J=7.5 Hz, 2H), 7.72 (t, J=8.1 Hz, 2H), 7.58 (d, J=8.0 Hz, 1H), 7.42 (t, J=7.4 Hz, 2H), 7.32 (t, J=9.1 Hz, 2H), 4.28-4.20 (m, 3H), 4.17-4.04 (m, 2H), 2.66-2.59 (m, 1H), 2.30-2.14 (m, 3H), 2.04-1.98 (m, 1H), 1.87-1.73 (m, 4H), 1.68-1.61 (m, 2H), 1.39 (s, 9H), 1.34-1.29 (m, 2H), 1.22 (d, J=9.1 Hz, 6H), 0.87-0.74 (m, 9H).

ESI-MS (M+Na)+: 695.

Example 8

Compound A8

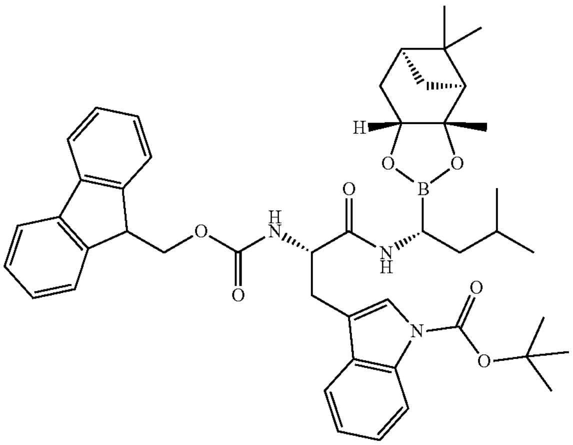

$^1$H NMR (400 MHz, DMSO) δ 8.95 (s, 1H), 8.03 (d, J=7.6 Hz, 1H), 7.90-7.80 (m, 3H), 7.73 (d, J=7.3 Hz, 1H), 7.67-7.53 (m, 3H), 7.46-7.15 (m, 6H), 4.62-4.39 (m, 1H), 4.20-4.10 (m, 4H), 3.13-2.87 (m, 2H), 2.67-2.50 (m, 1H), 2.30-2.11 (m, 1H), 2.06-1.95 (m, 1H), 1.85-1.72 (m, 2H), 1.70-1.47 (m, 11H), 1.37-1.12 (m, 9H), 0.90-0.68 (m, 9H).

ESI-MS (M+Na)+: 796.

Example 9

Compound A9

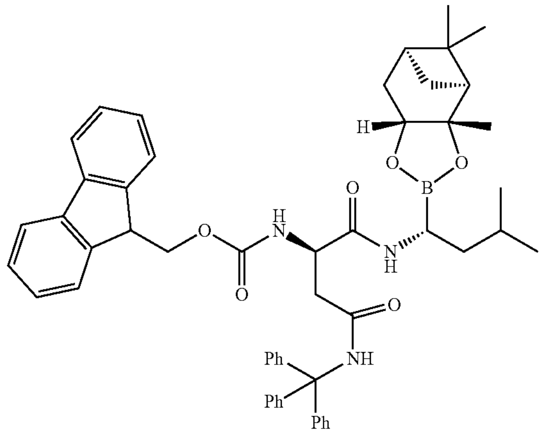

$^1$H NMR (400 MHz, DMSO) δ 8.81 (s, 1H), 8.60 (s, 1H), 7.90 (d, J=7.6 Hz, 2H), 7.82-7.70 (m, 2H), 7.42 (dd, J=15.8, 7.9 Hz, 2H), 7.34 (d, J=7.3 Hz, 1H), 7.28-7.06 (m, 17H), 4.47-4.30 (m, 2H), 4.25-4.18 (m, 2H), 4.12-4.08 (m, 1H), 2.80-2.64 (m, 1H), 2.62-2.52 (m, 1H), 2.25-2.16 (m, 1H), 2.03-2.00 (m, 1H), 1.86-1.73 (m, 2H), 1.67-1.60 (m, 2H), 1.45-1.18 (m, 9H), 0.84-0.72 (m, 9H).

ESI-MS $(M+H)^+$: 844.

Example 10

Compound A10

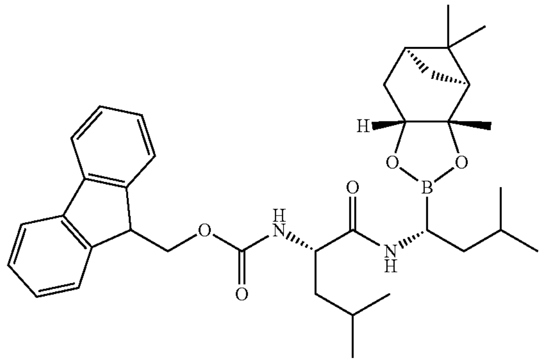

$^1$H NMR (400 MHz, DMSO) δ 8.98 (s, 1H), 7.90 (d, J=7.5 Hz, 2H), 7.71 (t, J=7.6 Hz, 2H), 7.61 (d, J=8.4 Hz, 1H), 7.42 (t, J=7.4 Hz, 2H), 7.33 (q, J=7.0 Hz, 2H), 4.29 (d, J=7.1 Hz, 2H), 4.24-4.12 (m, 2H), 4.06 (d, J=7.0 Hz, 1H), 2.31-2.10 (m, 1H), 2.10-1.88 (m, 1H), 1.88-1.63 (m, 4H), 1.63-1.33 (m, 4H), 1.33-1.17 (m, 9H), 0.94-0.75 (m, 13H).

ESI-MS (M+Na)+: 623.

Example 11

Compound A11

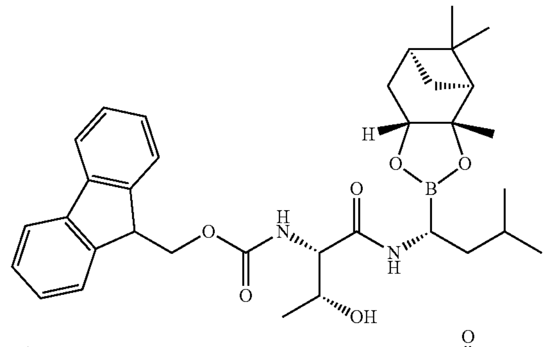

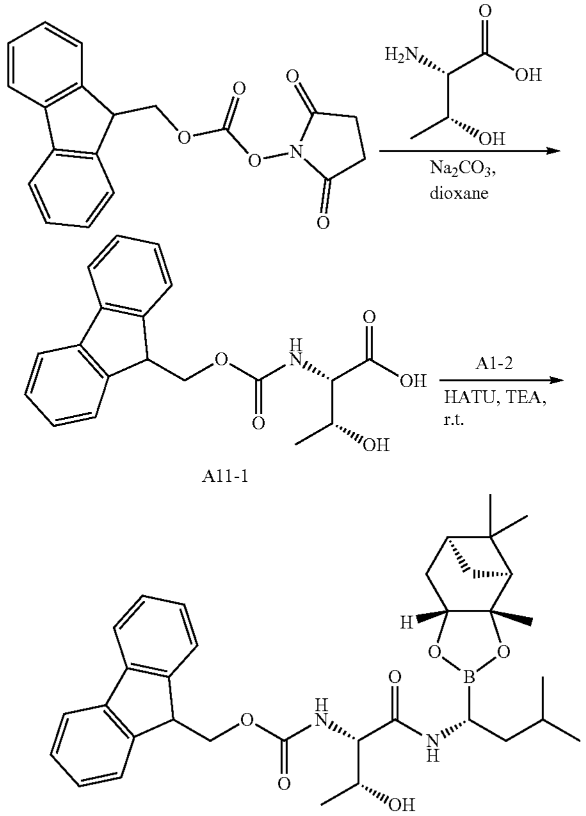

A11

It is synthesized as follows:

1. Synthesis of Intermediate A11-1

L-threonine (119 mg, 1 mmol) and sodium carbonate (159 mg, 1.5 mmol) were dissolved in 1,4-dioxane (3 mL) and water (2 mL), and 9-fluorenylmethyl-N-succinimidyl carbonate (337 mg, 1 mmol) in 1,4-dioxane (3 mL) solution was added slowly. The reaction was carried out at room temperature for 6 h. Thin layer chromatography (TLC) showed that the raw materials were completely reacted. The solvent was spin-dried, diluted hydrochloric acid was added to adjust the pH to 3-4, a solid precipitated. The mixture was filtered. The filter cake was washed with ethyl acetate, dried with anhydrous sodium sulfate, filtered, and spin-dried to obtain a white solid compound A11-1 (280 mg, yield 82%).

2. Synthesis of Compound A11

Compound A11-1 (170 mg, 0.5 mmol) and A1-2 (227 mg, 0.6 mmol) were dissolved in DCM (3 mL), and 2-(7- azobenzotriazole)-N,N,N',N'-tetramethylurea hexafluorophosphate (HATU) (285 mg, 0.75 mmol) and triethylamine (TEA) (151 mg, 1.5 mmol) were added. The mixture was reacted at room temperature for 2 hours. After that, water was added, and the mixture was extracted with DCM (15 mL*3). The organic phases were combined, and after the solvent was spin-dried, the crude product was purified by medium pressure preparative liquid chromatography to obtain a white solid compound A11 (20 mg, yield 6.8%).

$^1$H NMR (400 MHz, DMSO) δ 8.88 (s, 1H), 7.90 (d, J=7.5 Hz, 2H), 7.75 (t, J=8.2 Hz, 2H), 7.53 (d, J=9.1 Hz, 1H), 7.43 (t, J=7.4 Hz, 2H), 7.34 (dd, J=12.8, 6.6 Hz, 2H), 4.94 (d, J=5.2 Hz, 1H), 4.29 (d, J=7.1 Hz, 2H), 4.24 (d, J=5.9 Hz, 1H), 4.09 (t, J=8.3 Hz, 2H), 3.88 (dd, J=11.6, 6.2 Hz, 1H), 3.61 (t, J=6.6 Hz, 2H), 2.18 (d, J=8.9 Hz, 1H), 2.00 (d, J=7.3 Hz, 2H), 1.84 (t, J=5.5 Hz, 1H), 1.80-1.75 (m, 2H), 1.36 (s, 2H), 1.34-1.29 (m, 2H), 1.25 (d, J=9.3 Hz, 7H), 1.22 (s, 4H), 1.07 (d, J=6.2 Hz, 3H), 0.85 (d, J=6.4 Hz, 6H), 0.81 (s, 3H).

ESI-MS (M+H)$^+$: 589.

The synthetic method of compound A12-A18 is the same as that of A11, except that the L-threonine was replaced with the corresponding amino acid.

Example 12

Compound A12

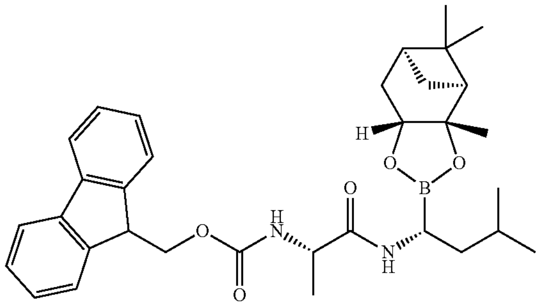

$^1$H NMR (400 MHz, DMSO) δ 8.83 (s, 1H), 7.90 (d, J=7.5 Hz, 2H), 7.72 (t, J=8.1 Hz, 2H), 7.64 (d, J=7.7 Hz, 1H), 7.43 (t, J=7.4 Hz, 2H), 7.33 (td, J=7.3, 3.6 Hz, 2H), 4.39-4.11 (m, 4H), 4.07 (d, J=6.6 Hz, 1H), 2.57 (s, 1H), 2.26-2.14 (m, 1H), 2.01 (dd, J=14.9, 7.1 Hz, 2H), 1.82 (t, J=5.6 Hz, 1H), 1.76 (s, 1H), 1.71-1.53 (m, 2H), 1.40-1.15 (m, 14H), 0.84 (d, J=6.5 Hz, 6H), 0.80 (s, 3H).

ESI-MS (M+H)$^+$: 573.

Example 13

Compound A13

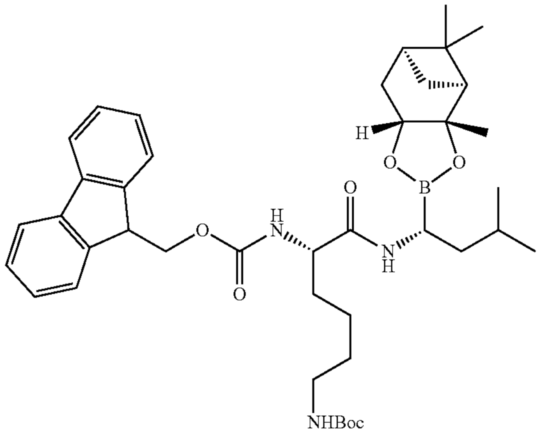

$^1$H NMR (400 MHz, DMSO) δ 8.90 (s, 1H), 7.90 (d, J=7.5 Hz, 2H), 7.71 (t, J=7.5 Hz, 2H), 7.58 (d, J=8.1 Hz, 1H), 7.42 (t, J=7.4 Hz, 2H), 7.33 (dd, J=12.4, 7.1 Hz, 2H), 6.76 (s, 1H), 4.34-4.16 (m, 3H), 4.07 (d, J=8.1 Hz, 2H), 2.89 (d, J=5.8 Hz, 2H), 2.56 (s, 1H), 2.25-2.13 (m, 1H), 2.04 (d, J=32.9 Hz, 2H), 1.81 (dd, J=16.8, 11.2 Hz, 2H), 1.72-1.52 (m, 5H), 1.36 (d, J=11.2 Hz, 13H), 1.22 (d, J=6.1 Hz, 11H), 0.84 (d, J=6.4 Hz, 7H), 0.80 (s, 3H).

ESI-MS (M+H)$^+$: 716.

Example 14

Compound A14

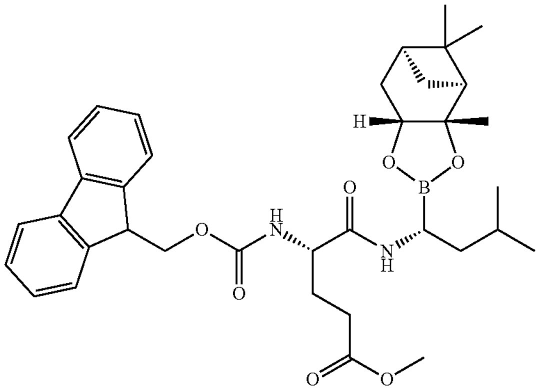

$^1$H NMR (400 MHz, DMSO) δ 8.73 (s, 1H), 7.90 (d, J=7.5 Hz, 2H), 7.72 (t, J=7.8 Hz, 2H), 7.61 (d, J=8.2 Hz, 1H), 7.43 (t, J=7.4 Hz, 2H), 7.33 (td, J=7.3, 3.4 Hz, 2H), 4.28 (d, J=6.8 Hz, 2H), 4.25-4.17 (m, 1H), 4.13 (t, J=8.5 Hz, 2H), 3.60 (s, 3H), 2.66 (d, J=17.5 Hz, 2H), 2.34 (t, J=14.6 Hz, 2H), 2.29-2.15 (m, 1H), 2.10-1.97 (m, 2H), 1.94-1.74 (m, 4H), 1.73-1.58 (m, 2H), 1.37-1.17 (m, 11H), 0.93-0.72 (m, 9H).

ESI-MS (M+H)$^+$: 645.

Example 15

Compound A15

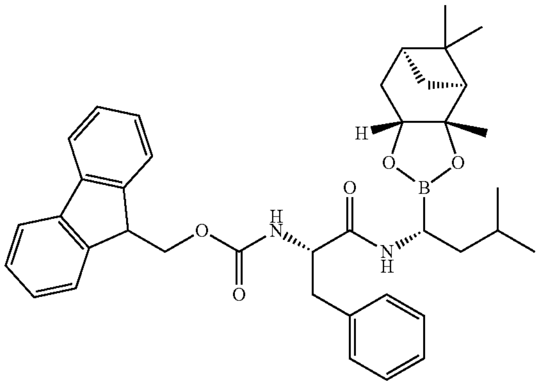

$^1$H NMR (400 MHz, DMSO) δ 8.89 (d, J=2.8 Hz, 1H), 7.89 (d, J=7.5 Hz, 2H), 7.75 (d, J=8.6 Hz, 2H), 7.64 (d, J=7.5 Hz, 2H), 7.41 (t, J=7.5 Hz, 2H), 7.29 (td, J=14.9, 7.6 Hz, 5H), 4.36 (dd, J=14.1, 9.1 Hz, 1H), 4.28-4.14 (m, 4H), 3.05-2.98 (m, 2H), 2.01 (d, J=15.3 Hz, 2H), 1.83 (dd, J=18.6, 13.1 Hz, 2H), 1.39-1.23 (m, 9H), 0.83 (dd, J=12.8, 6.1 Hz, 8H).

ESI-MS $(M+H)^+$: 635.

Example 16

Compound A16

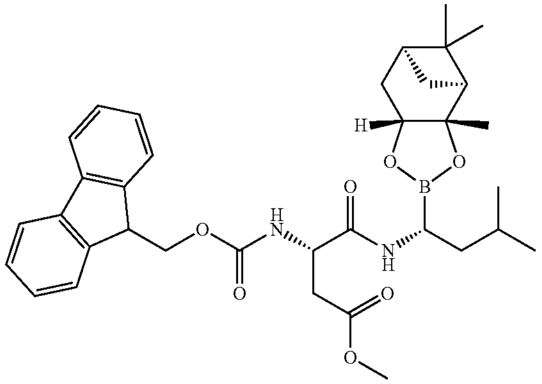

$^1$H NMR (400 MHz, DMSO) δ 8.64 (s, 1H), 7.89 (d, J=7.5 Hz, 2H), 7.70 (d, J=8.0 Hz, 3H), 7.42 (t, J=7.4 Hz, 2H), 7.33 (t, J=7.5 Hz, 2H), 4.48 (dd, J=13.9, 8.4 Hz, 1H), 4.34-4.19 (m, 3H), 4.14-4.09 (m, 1H), 3.59 (s, 3H), 2.66 (dd, J=11.0, 6.2 Hz, 2H), 2.25-2.15 (m, 1H), 2.00 (dd, J=14.1, 6.6 Hz, 2H), 1.84 (t, J=5.6 Hz, 1H), 1.77 (s, 1H), 1.64 (t, J=12.7 Hz, 2H), 1.30-1.22 (m, 9H), 0.85-0.76 (m, 9H).

ESI-MS $(M+Na)^+$: 639.

Example 17

Compound A17

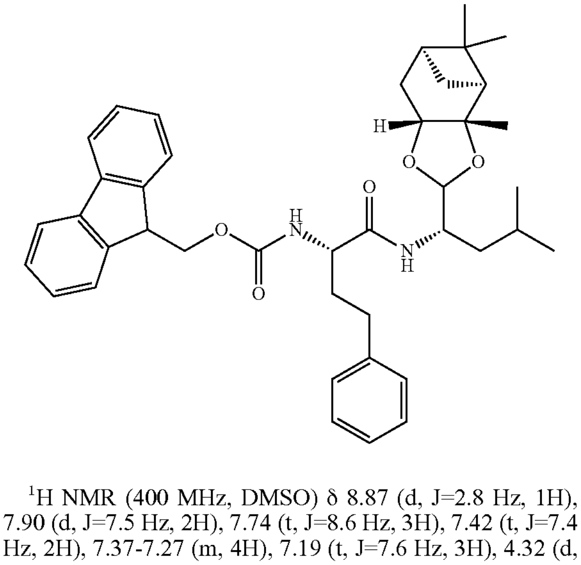

$^1$H NMR (400 MHz, DMSO) δ 8.87 (d, J=2.8 Hz, 1H), 7.90 (d, J=7.5 Hz, 2H), 7.74 (t, J=8.6 Hz, 3H), 7.42 (t, J=7.4 Hz, 2H), 7.37-7.27 (m, 4H), 7.19 (t, J=7.6 Hz, 3H), 4.32 (d, J=7.0 Hz, 2H), 4.24 (t, J=7.0 Hz, 1H), 4.10 (dd, J=12.9, 7.1 Hz, 2H), 2.68-2.54 (m, 3H), 2.19 (d, J=2.3 Hz, 1H), 2.08 (s, 1H), 2.05-1.96 (m, 1H), 1.88 (dd, J=15.4, 7.9 Hz, 2H), 1.82 (t, J=5.6 Hz, 1H), 1.76 (s, 1H), 1.71-1.59 (m, 2H), 1.32 (dd, J=15.2, 6.2 Hz, 2H), 1.23 (s, 3H), 1.20 (s, 3H), 0.84 (d, J=6.5 Hz, 6H), 0.79 (s, 3H).

ESI-MS $(M+H)^+$: 649.

Example 18

Compound A18

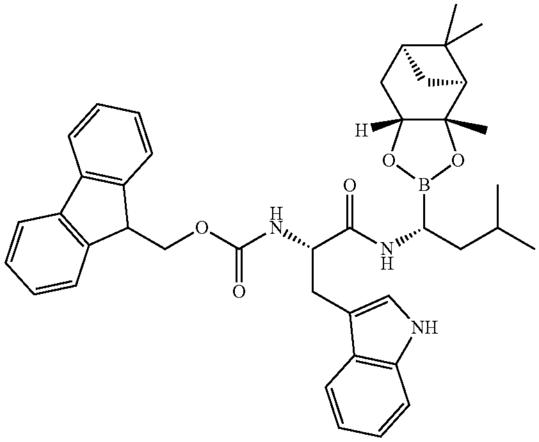

$^1$H NMR (400 MHz, DMSO) δ 10.87 (s, 1H), 9.05 (s, 1H), 7.86 (d, J=7.6 Hz, 2H), 7.63 (dd, J=15.2, 7.7 Hz, 4H), 7.38 (dd, J=13.1, 6.9 Hz, 2H), 7.31 (d, J=8.8 Hz, 2H), 7.25 (dd, J=14.5, 6.7 Hz, 1H), 7.17 (s, 1H), 7.05 (t, J=7.2 Hz, 1H), 6.97 (t, J=7.3 Hz, 1H), 4.39 (d, J=5.8 Hz, 1H), 4.19-4.05 (m, 4H), 3.08-2.93 (m, 2H), 2.52 (s, 1H), 2.16 (s, 2H), 2.06-1.90 (m, 2H), 1.81 (dd, J=18.0, 12.2 Hz, 2H), 1.64 (d, J=14.8 Hz, 2H), 1.30-1.20 (m, 7H), 0.88-0.73 (m, 9H).

ESI-MS $(M+H)^+$: 674.

Example 19

Compound A19

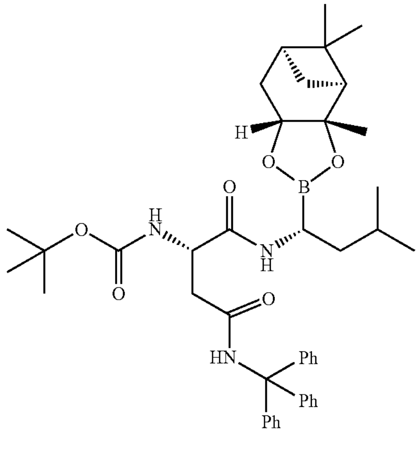

Compound A19 was synthesized as follows:

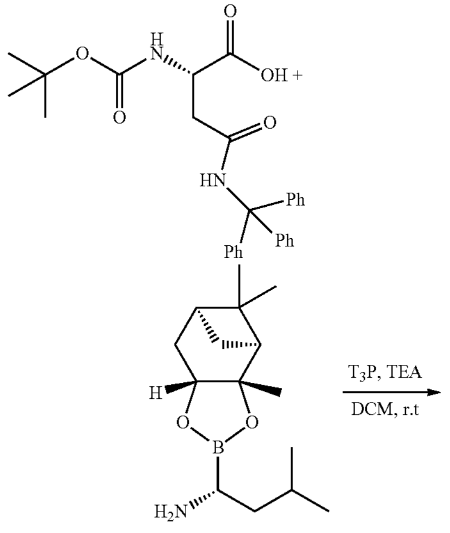

$CF_3COOH$
A1-2

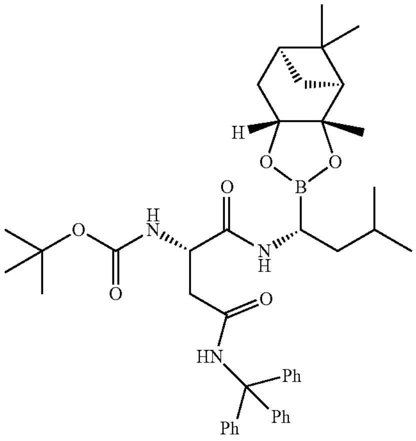

A19

$N^2$-boc-$N^4$-Trt-L-asparagine (200 mg, 0.42 mmol) was dissolved in dichloromethane (10 mL), and 1-propyl phosphoric anhydride (T3P) (50% wt, ethyl acetate (EtOAc, 1.2 mL)), A1-2 (135 mg, 0.51 mmol) and TEA (1.2 mL) were added. After reacting at room temperature for 3 hours, it was diluted with water (30 mL). The mixture was extracted with dichloromethane (20 mL*3) and then combined, dried and spin-dried. The solute was purified by medium pressure preparative liquid chromatography to obtain a white solid (100 mg, 33% yield).

$^1$H NMR (400 MHz, DMSO) δ 8.85 (s, 1H), 8.60 (s, 1H), 7.23 (dt, J=13.5, 7.8 Hz, 15H), 7.13 (d, J=8.4 Hz, 1H), 4.39-4.27 (m, 1H), 4.07 (d, J=7.2 Hz, 1H), 2.67 (dd, J=14.2, 10.4 Hz, 1H), 2.53 (d, J=9.5 Hz, 1H), 2.43 (dd, J=14.6, 4.0 Hz, 1H), 2.20 (dd, J=21.4, 10.0 Hz, 1H), 2.09-1.95 (m, 3H), 1.83 (t, J=5.5 Hz, 1H), 1.79 (d, J=5.4 Hz, 1H), 1.66 (dd, J=18.1, 10.3 Hz, 2H), 1.34 (dd, J=12.2, 7.8 Hz, 6H), 1.31-1.16 (m, 10H), 0.89-0.75 (m, 9H).

ESI-MS (M−H)−: 720.

The synthesis method of compound A20-A21 is the same as that of A19, except that the raw material $N^2$-boc-$N^4$-Trt-L-asparagine was replaced with $N^2$-Cbz-$N^4$-Trt-L-asparagine and Cbz-L-tryptophan.

Example 20

Compound A20

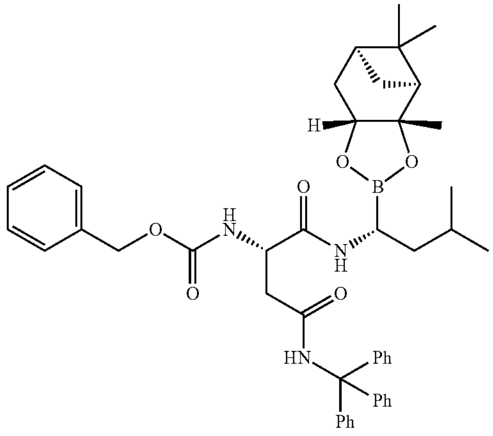

$^1$H NMR (400 MHz, DMSO) δ 8.91 (s, 1H), 8.76 (d, J=12.1 Hz, 2H), 7.64 (d, J=8.3 Hz, 1H), 7.49-7.34 (m, 5H), 7.30 (s, 2H), 7.25-7.01 (m, 14H), 5.12-5.01 (m, 2H), 4.11 (dd, J=12.5, 7.2 Hz, 3H), 2.70 (dd, J=14.6, 10.4 Hz, 1H), 2.51 (dt, J=3.6, 1.8 Hz, 5H), 2.25-2.16 (m, 1H), 1.98 (m, 1H), 1.74 (m, 2H), 1.16 (m, 9H), 0.85 (dd, J=20.2, 13.6 Hz, 9H).

ESI-MS $(M+H)^+$: 844.

Example 21

Compound A21

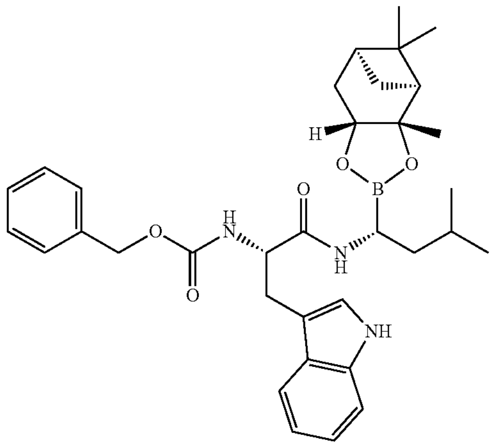

$^1$H NMR (400 MHz, DMSO) δ 10.89 (s, 1H), 9.09 (s, 1H), 7.59 (dd, J=23.8, 8.1 Hz, 2H), 7.37-7.29 (m, 3H), 7.28-7.22 (m, 2H), 7.17 (d, J=2.2 Hz, 1H), 7.07 (t, J=7.5 Hz, 1H), 6.99 (t, J=7.2 Hz, 1H), 4.96 (q, J=12.7 Hz, 2H), 4.45-4.34 (m, 1H), 4.11 (d, J=7.0 Hz, 1H), 3.10-3.02 (m, 1H), 2.98 (dd, J=14.4, 9.1 Hz, 1H), 2.55 (d, J=8.5 Hz, 1H), 2.29-2.18 (m, 1H), 2.07-1.97 (m, 1H), 1.85 (dd, J=18.0, 12.3 Hz, 2H), 1.64 (dd, J=19.1, 10.5 Hz, 2H), 1.38 (d, J=10.0 Hz, 1H), 1.29 (s, 3H), 1.22 (d, J=12.5 Hz, 6H), 0.84 (t, J=6.0 Hz, 8H).

ESI-MS $(M+H)^+$: 586.

Example 22

Compound A22

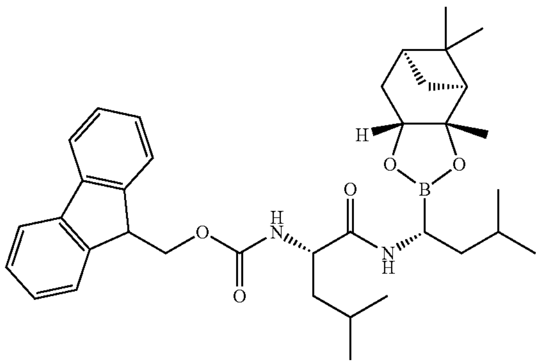

Compound A22 was synthesized as follows:

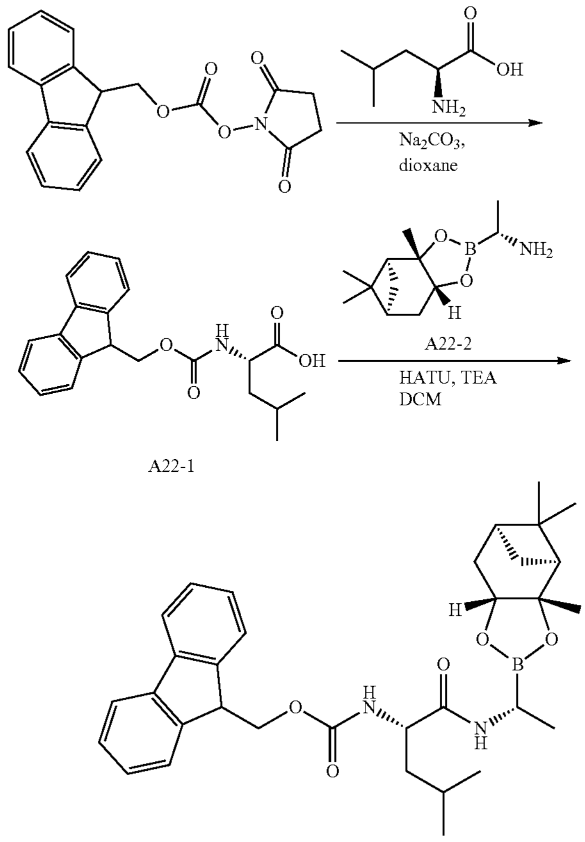

A22-1

A22

1. Synthesis of Intermediate A22-1:

L-leucine (131 mg, 1 mmol) and sodium carbonate (159 mg, 1.5 mmol) were dissolved in 1,4-dioxane (3 mL) and water (2 mL), and 9-fluorenylmethyl-N-succinimidyl carbonate (337 mg, 1 mmol) in 1,4-dioxane (3 mL) solution was added slowly. The reaction was carried out at room temperature for 6 h. TLC showed that the raw materials were completely reacted. The solvent was spin-dried, and diluted hydrochloric acid was added to adjust the pH to 3-4, and a solid precipitated. The mixture was filtered, and the filter cake was washed with ethyl acetate, dried with anhydrous sodium sulfate, filtered, and spin-dried to obtain a white solid compound A22-1 (250 mg, yield 71%).

1. Synthesis of Compound A22

Compound A87-1 (176 mg, 0.5 mmol) and compound A22-2 (227 mg, 0.6 mmol) were dissolved in DCM (3 mL), and HATU (285 mg, 0.75 mmol) and TEA (151 mg, 1.5 mmol) were added. The mixture was reacted at room temperature for 2 hours. Water was added, and the mixture was extracted with DCM (15 mL*3). The organic phases were combined, and after the solvent was spin-dried, the crude product was purified by medium pressure preparative liquid chromatography to obtain white solid compound A22 (18 mg, yield 6.4%).

$^1H$ NMR (400 MHz, DMSO) δ 9.11 (s, 1H), 7.89 (d, J=7.5 Hz, 2H), 7.71 (t, J=7.7 Hz, 2H), 7.64 (d, J=8.3 Hz, 1H), 7.41 (t, J=7.4 Hz, 2H), 7.32 (dt, J=14.2, 7.0 Hz, 2H), 4.36-4.24 (m, 2H), 4.21 (t, J=6.9 Hz, 1H), 4.13 (td, J=9.7, 5.1 Hz, 1H), 4.04 (d, J=6.9 Hz, 1H), 2.57-2.51 (m, 1H), 2.18 (dd, J=12.2, 9.9 Hz, 1H), 2.05-1.92 (m, 1H), 1.81 (t, J=5.6 Hz, 1H), 1.77 (d, J=5.2 Hz, 1H), 1.68-1.56 (m, 2H), 1.56-1.48 (m, 1H), 1.40 (ddd, J=21.4, 10.7, 6.3 Hz, 1H), 1.33 (d, J=10.0 Hz, 1H), 1.23 (t, J=7.2 Hz, 9H), 1.00 (d, J=7.2 Hz, 3H), 0.89 (d, J=6.5 Hz, 3H), 0.84 (d, J=6.4 Hz, 4H), 0.79 (s, 3H).

ESI-MS $(M+H)^+$: 601.

The synthesis method of compound A23 is the same as that of A22, except that L-leucine is replaced with Boc-L-lysine.

Example 23

Compound A23

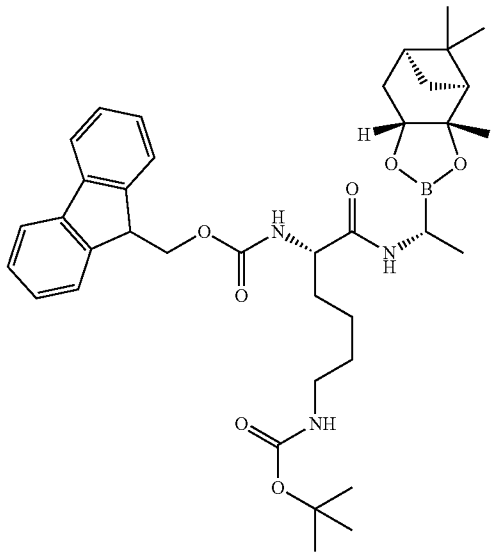

$^1H$ NMR (400 MHz, DMSO) δ 9.04 (s, 1H), 7.90 (d, J=7.5 Hz, 2H), 7.72 (t, J=7.5 Hz, 2H), 7.62 (d, J=8.0 Hz, 1H), 7.42 (t, J=7.4 Hz, 2H), 7.33 (dd, J=12.4, 7.1 Hz, 2H), 6.76 (s, 1H), 4.26 (dd, J=23.9, 6.5 Hz, 3H), 4.05 (d, J=8.4 Hz, 2H), 2.89 (d, J=6.0 Hz, 2H), 2.55 (s, 1H), 2.25-2.14 (m, 1H), 2.06-1.95 (m, 1H), 1.83 (t, J=5.5 Hz, 1H), 1.77 (s, 1H), 1.69-1.48 (m, 3H), 1.37 (s, 13H), 1.23 (d, J=7.6 Hz, 9H), 1.01 (d, J=7.2 Hz, 3H), 0.80 (s, 3H).

ESI-MS$(M+H)^+$:674.

Example 24

Compound A24

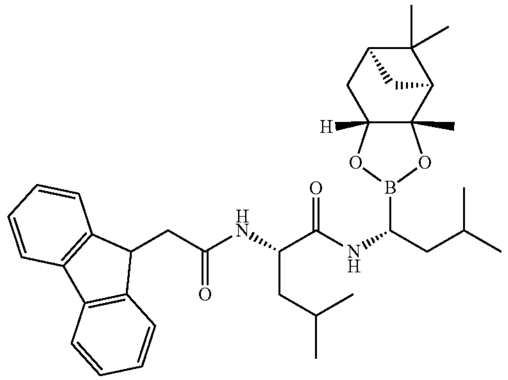

Compound A24 was synthesized as follows:

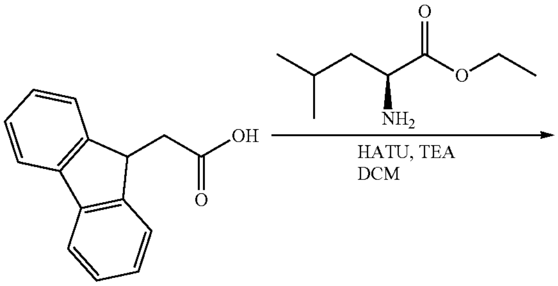

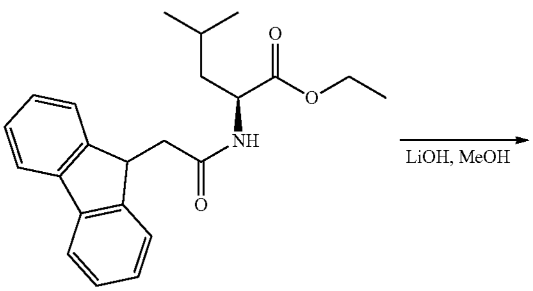

A24-1

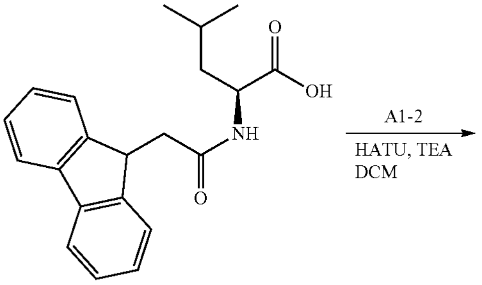

A24-2

-continued

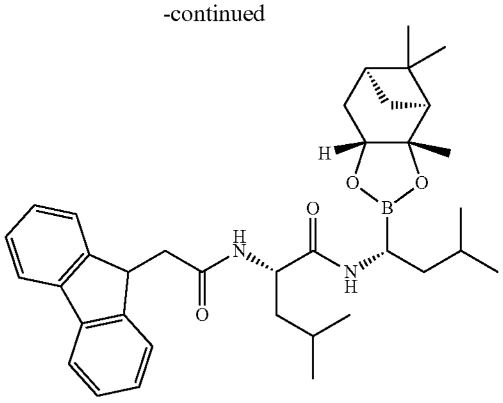

A24

1. Synthesis of Intermediate A24-1

9-Fluoreneacetic acid (224 mg, 1 mmol) and L-leucine ethyl ester (286 mg, 1.8 mmol) were dissolved in DCM (4 mL), and 2-(7-azobenzotriazole)-N,N,N',N'-tetramethylurea hexafluorophosphate (HATU) (760 mg, 2 mmol) and TEA (350 mg, 3.5 mmol) were added. The mixture was reacted at room temperature for 2 hours. Water was added, and the mixture was extracted with DCM (20 mL*3). The organic phases were combined, and after the solvent was spin-dried, the organic phases were purified with a prep-TLC to obtain white solid compound A24-1 (145 mg, yield 40%).

2. Synthesis of Intermediate A24-2

Compound A24-1 (145 mg, 0.4 mmol) was dissolved in methanol (MeOH) (4 mL), lithium hydroxide (LiOH) (1 mL, 1M) aqueous solution was added at low temperature, and the reaction was carried out at room temperature for 2 hours. TLC showed that the raw materials were completely reacted. The solvent was spin-dried. Diluted hydrochloric acid was added to adjust the pH to 3-4. The mixture was extracted with ethyl acetate (10 mL*3). The organic phases were combined, and the solvent was spin-dried to obtain compound A24-2 (102 mg, yield 75.6%).

3. Synthesis of Compound A24

Compound A24-2 (100 mg, 0.3 mmol) and compound A1-2 (170 mg, 0.45 mmol) were dissolved in DCM (3 mL), and HATU (228 mg, 0.6 mmol) and TEA (120 mg, 1.2 mmol) were added. The mixture was reacted at room temperature for 2 hours. Water was added, and the mixture was extracted with DCM (15 mL*3). The organic phases were combined, and after the solvent was spin-dried, the crude product was purified by medium pressure preparative liquid chromatography to obtain a white solid compound A24 (25 mg, yield 14.3%).

$^1$H NMR (400 MHz, DMSO) δ 9.06 (d, J=2.5 Hz, 1H), 8.24 (d, J=8.0 Hz, 1H), 7.86 (d, J=7.5 Hz, 2H), 7.54 (d, J=7.4 Hz, 1H), 7.49 (d, J=7.5 Hz, 1H), 7.38 (t, J=7.4 Hz, 2H), 7.33-7.22 (m, 2H), 4.65-4.55 (m, 1H), 4.36 (t, J=7.5 Hz, 1H), 4.08 (dd, J=8.5, 1.7 Hz, 1H), 2.69 (dd, J=14.8, 6.9 Hz, 1H), 2.59 (dd, J=10.6, 4.6 Hz, 1H), 2.47 (d, J=8.3 Hz, 1H), 2.26-2.14 (m, 1H), 2.07-1.96 (m, 1H), 1.85 (t, J=5.6 Hz, 1H), 1.81-1.69 (m, 2H), 1.68-1.56 (m, 2H), 1.55-1.38 (m, 2H), 1.38-1.26 (m, 3H), 1.24 (d, J=12.3 Hz, 6H), 0.89 (dd, J=15.5, 6.6 Hz, 12H), 0.81 (s, 3H).

ESI-MS $(M+H)^+$: 584.

The synthesis method of compound A25-A38 is the same as that of A24, except that the raw materials in the first step, 9-fluorene acetic acid and L-leucine ethyl ester are replaced with corresponding acids and amino acid esters.

Example 25

Compound A25

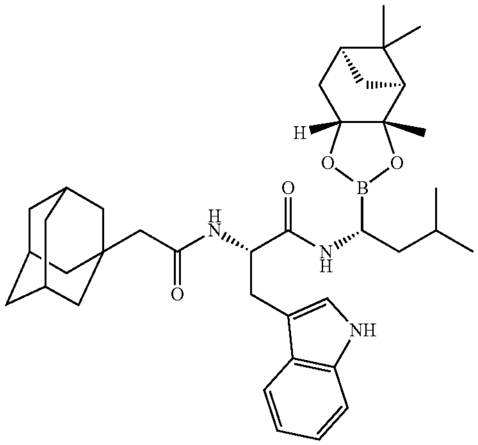

$^1$H NMR (400 MHz, DMSO) δ 10.85 (s, 1H), 9.03 (s, 1H), 7.92 (dd, J=45.2, 8.1 Hz, 1H), 7.60 (d, J=7.7 Hz, 1H), 7.31 (d, J=8.0 Hz, 1H), 7.20-7.12 (m, 1H), 7.05 (t, J=7.5 Hz, 1H), 6.98 (t, J=7.4 Hz, 1H), 4.69 (dt, J=16.4, 8.3 Hz, 1H), 4.18-4.01 (m, 1H), 3.12-3.00 (m, 1H), 2.99-2.88 (m, 1H), 2.28-2.16 (m, 1H), 2.02 (d, J=6.6 Hz, 1H), 1.90-1.84 (m, 1H), 1.80 (s, 6H), 1.71-1.61 (m, 2H), 1.61 (s, 3H), 1.45 (d, J=11.6 Hz, 3H), 1.38 (s, 6H), 1.30 (d, J=13.2 Hz, 4H), 1.23 (s, 6H), 0.83 (d, J=5.2 Hz, 9H).

ESI-MS(M+H)$^+$: 628.

Example 26

Compound A26

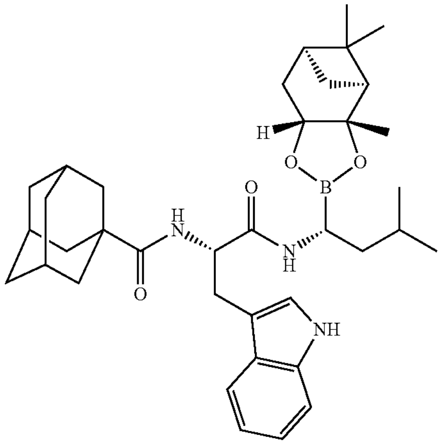

$^1$H NMR (400 MHz, DMSO) δ 10.85 (d, J=5.3 Hz, 1H), 8.78 (d, J=3.0 Hz, 1H), 7.66-7.55 (m, 1H), 7.31 (d, J=7.9 Hz, 2H), 7.16 (d, J=2.2 Hz, 1H), 7.06 (s, 1H), 6.98 (s, 1H), 4.72-4.53 (m, 1H), 4.17-4.03 (m, 1H), 3.19-2.96 (m, 2H), 2.30-2.14 (m, 1H), 2.10-1.98 (m, 1H), 1.91 (s, 5H), 1.62 (dd, J=25.6, 13.3 Hz, 14H), 1.29 (d, J=6.2 Hz, 3H), 1.24 (d, J=2.7 Hz, 4H), 0.90-0.78 (m, 9H).

ESI-MS (M+H)$^+$: 614.

Example 27

Compound A27

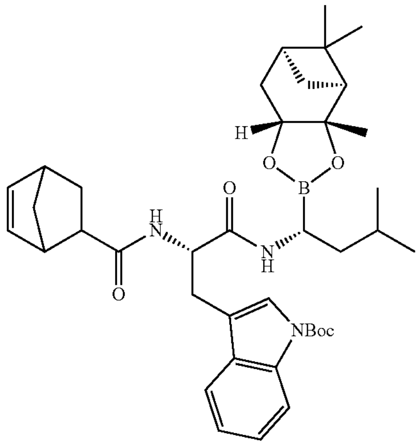

$^1$H NMR (400 MHz, DMSO) δ 8.89 (dd, J=77.4, 3.0 Hz, 1H), 8.03 (d, J=8.1 Hz, 1H), 7.92 (d, J=8.3 Hz, 1H), 7.69 (d, J=7.6 Hz, 1H), 7.51 (s, 1H), 7.29 (dt, J=26.5, 7.3 Hz, 2H), 5.99 (dt, J=5.9, 3.0 Hz, 1H), 5.74 (ddd, J=20.9, 5.5, 2.7 Hz, 1H), 4.64 (d, J=6.5 Hz, 1H), 4.20-4.02 (m, 1H), 3.16 (d, J=14.3 Hz, 1H), 3.08-2.89 (m, 2H), 2.80 (dd, J=11.2, 5.3 Hz, 2H), 2.28-2.14 (m, 1H), 2.02 (dd, J=14.2, 6.7 Hz, 1H), 1.90-1.76 (m, 2H), 1.73-1.54 (m, 11H), 1.39-1.26 (m, 5H), 1.29-1.09 (m, 9H), 0.92-0.72 (m, 9H).

ESI-MS (M+H)$^+$: 672.

Example 28

Compound A28

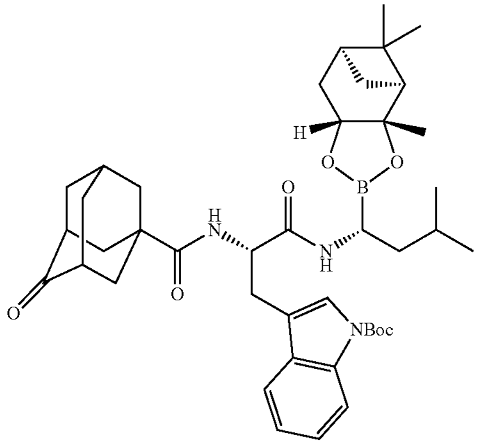

$^1$H NMR (400 MHz, DMSO) δ 8.99 (d, J=2.9 Hz, 1H), 8.04 (d, J=8.1 Hz, 1H), 7.79 (d, J=8.5 Hz, 1H), 7.71 (d, J=7.6 Hz, 1H), 7.53 (s, 1H), 7.29 (dt, J=24.3, 7.0 Hz, 2H), 4.69 (dd, J=14.9, 8.5 Hz, 1H), 4.12 (t, J=12.1 Hz, 1H), 3.04 (s, 2H), 2.59-2.53 (m, 1H), 2.38 (s, 2H), 2.22 (dd, J=12.3, 9.9 Hz, 1H), 2.09-1.76 (m, 16H), 1.61 (s, 9H), 1.25 (d, J=18.9 Hz, 9H), 0.86-0.80 (m, 9H).

ESI-MS (M+H)$^+$: 728.

Example 29

Compound A29

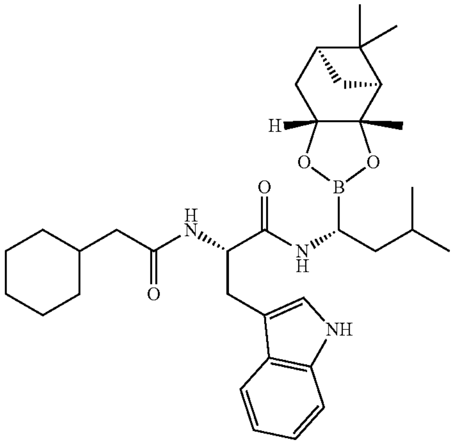

$^1$H NMR (400 MHz, DMSO) δ 10.87 (d, J=1.7 Hz, 1H), 9.09 (s, 1H), 8.02 (d, J=8.2 Hz, 1H), 7.60 (d, J=7.8 Hz, 1H), 7.32 (d, J=8.0 Hz, 1H), 7.16 (d, J=2.2 Hz, 1H), 7.06 (dd, J=11.1, 4.0 Hz, 1H), 6.99 (dd, J=10.9, 3.9 Hz, 1H), 4.66 (td, J=8.6, 5.5 Hz, 1H), 4.08 (dd, J=8.5, 1.8 Hz, 1H), 3.00 (ddd, J=23.6, 14.5, 7.2 Hz, 2H), 2.26-2.19 (m, 1H), 2.08-1.97 (m, 1H), 1.94-1.88 (m, 2H), 1.86 (dd, J=11.4, 6.2 Hz, 1H), 1.83-1.78 (m, 2H), 1.69-1.48 (m, 5H), 1.37 (d, J=7.9 Hz, 4H), 1.29 (d, J=6.2 Hz, 3H), 1.25-1.18 (m, 6H), 1.15-0.99 (m, 4H), 0.82 (dd, J=13.3, 8.8 Hz, 9H).

ESI-MS $(M+H)^+$: 576.

Example 30

Compound A30

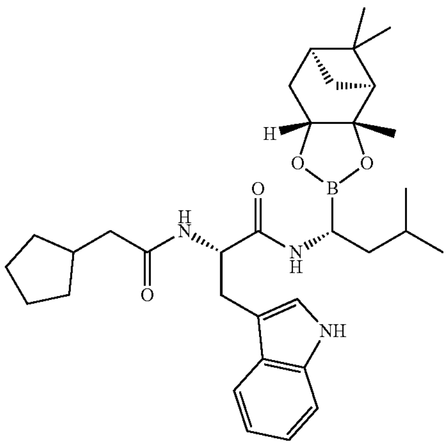

$^1$H NMR (400 MHz, DMSO) δ 10.86 (s, 1H), 9.07 (s, 1H), 8.00 (d, J=8.2 Hz, 1H), 7.59 (d, J=7.8 Hz, 1H), 7.31 (d, J=8.0 Hz, 1H), 7.15 (d, J=2.2 Hz, 1H), 7.05 (t, J=7.1 Hz, 1H), 6.98 (t, J=7.4 Hz, 1H), 4.70-4.59 (m, 1H), 4.13-4.03 (m, 1H), 3.00 (ddd, J=23.5, 14.6, 7.2 Hz, 2H), 2.27-2.14 (m, 1H), 2.00 (dd, J=9.2, 5.0 Hz, 4H), 1.84 (t, J=5.6 Hz, 1H), 1.80 (d, J=5.2 Hz, 1H), 1.70-1.34 (m, 10H), 1.27-1.16 (m, 10H), 1.10-0.92 (m, 2H), 0.82 (dd, J=4.5, 1.7 Hz, 9H).

ESI-MS $(M+Na)^+$: 561.56.

Example 31

Compound A31

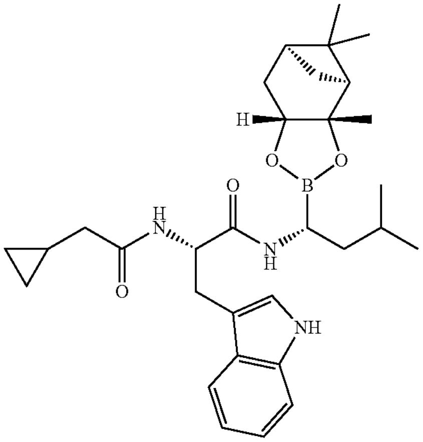

$^1$H NMR (400 MHz, DMSO) δ 10.83 (s, 1H), 9.02-8.90 (m, 1H), 7.98-7.83 (m, 1H), 7.55 (d, J=7.8 Hz, 1H), 7.28 (d, J=8.0 Hz, 1H), 7.11 (d, J=2.4 Hz, 1H), 7.02 (t, J=7.5 Hz, 1H), 6.94 (t, J=7.4 Hz, 1H), 4.60 (dt, J=10.4, 6.7 Hz, 1H), 4.06 (d, J=6.7 Hz, 1H), 3.09-2.97 (m, 1H), 2.97-2.84 (m, 1H), 2.23-2.12 (m, 1H), 1.98 (dd, J=14.5, 6.8 Hz, 2H), 1.86-1.73 (m, 2H), 1.67-1.48 (m, 2H), 1.29-1.10 (m, 9H), 0.83-0.76 (m, 9H).

ESI-MS $(M+H)^+$: 534.

Example 32

Compound A32

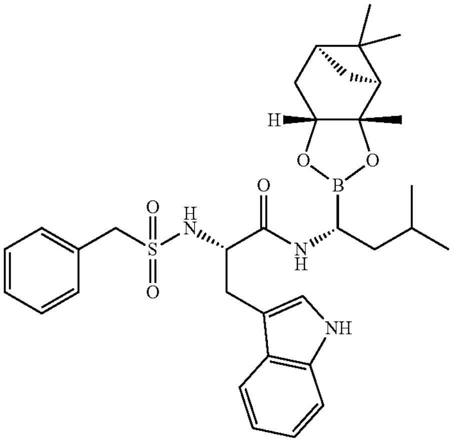

$^1$H NMR (400 MHz, DMSO) δ 10.92 (s, 1H), 8.91 (d, J=3.3 Hz, 1H), 7.70 (d, J=8.6 Hz, 1H), 7.60 (d, J=7.7 Hz, 1H), 7.39-7.26 (m, 4H), 7.19 (dd, J=7.7, 2.2 Hz, 3H), 7.11-6.97 (m, 2H), 4.18 (ddd, J=39.6, 24.2, 10.7 Hz, 3H), 3.91 (d, J=13.7 Hz, 1H), 3.03 (ddd, J=22.1, 14.4, 7.2 Hz, 2H), 2.59 (d, J=9.3 Hz, 1H), 2.26-2.17 (m, 1H), 2.07-1.99 (m, 1H), 1.83 (dd, J=15.4, 9.6 Hz, 2H), 1.67 (d, J=13.9 Hz, 1H), 1.51-1.44 (m, 1H), 1.36 (d, J=10.2 Hz, 1H), 1.28 (s, 3H), 1.26-1.20 (m, 5H), 1.20-1.16 (m, 1H), 0.79 (dd, J=6.7, 3.5 Hz, 9H).

ESI-MS $(M+H)^+$: 606.

Example 33

Compound A33

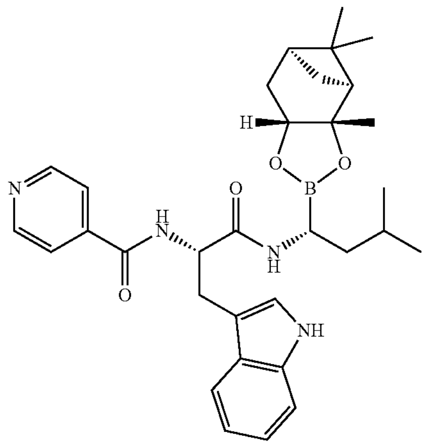

$^1H$ NMR (400 MHz, DMSO) δ 10.83 (s, 1H), 9.11 (d, J=2.9 Hz, 1H), 8.92 (d, J=8.2 Hz, 1H), 8.70 (dd, J=4.5, 1.5 Hz, 2H), 7.75-7.63 (m, 3H), 7.30 (d, J=8.0 Hz, 1H), 7.22 (d, J=2.2 Hz, 1H), 7.05 (t, J=7.0 Hz, 1H), 6.98 (t, J=7.4 Hz, 1H), 4.89-4.78 (m, 1H), 4.12 (d, J=6.7 Hz, 1H), 3.24-3.12 (m, 2H), 2.59 (t, J=7.7 Hz, 1H), 2.27-2.15 (m, 1H), 2.06-1.98 (m, 1H), 1.83 (dd, J=17.2, 11.5 Hz, 2H), 1.63 (dd, J=13.3, 7.7 Hz, 2H), 1.32 (dd, J=18.5, 9.1 Hz, 3H), 1.26 (s, 3H), 1.22 (s, 4H), 0.88-0.75 (m, 9H).

ESI-MS $(M+H)^+$: 557.

Example 34

Compound A34

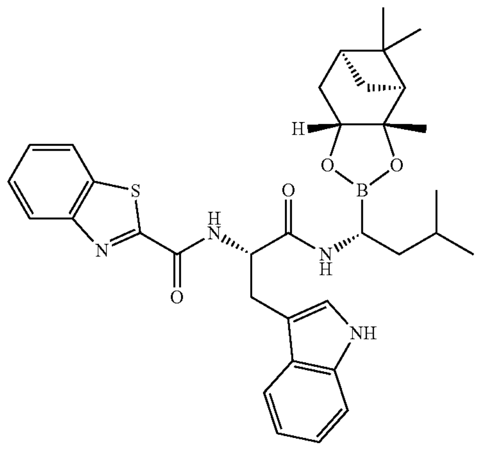

$^1H$ NMR (400 MHz, DMSO) δ 10.86 (s, 1H), 8.94 (dd, J=23.9, 6.0 Hz, 2H), 8.28-8.07 (m, 2H), 7.72-7.52 (m, 3H), 7.31 (d, J=8.1 Hz, 1H), 7.21 (d, J=2.1 Hz, 1H), 7.05 (t, J=7.5 Hz, 1H), 6.96 (t, J=7.4 Hz, 1H), 4.86 (dt, J=13.5, 6.8 Hz, 1H), 4.18 (d, J=8.6 Hz, 1H), 3.32-3.23 (m, 2H), 2.69 (d, J=3.6 Hz, 1H), 2.29-2.19 (m, 1H), 2.03 (dd, J=17.1, 8.9 Hz, 1H), 1.87 (t, J=5.6 Hz, 1H), 1.80 (s, 1H), 1.65 (t, J=12.8 Hz, 2H), 1.37-1.21 (m, 10H), 0.90-0.76 (m, 8H).

ESI-MS $(M+H)^+$: 613.

Example 35

Compound A35

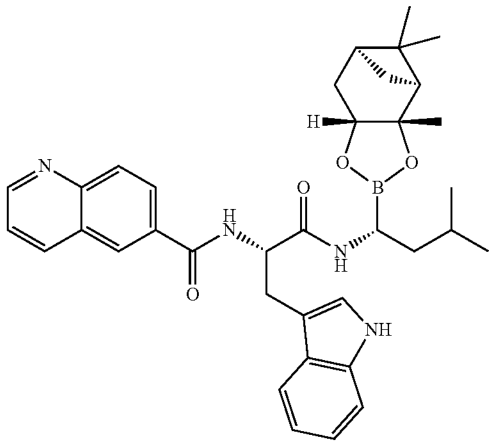

$^1H$ NMR (400 MHz, DMSO) δ 10.85 (s, 1H), 9.20-9.11 (m, 1H), 8.99 (dd, J=4.2, 1.6 Hz, 1H), 8.86 (t, J=9.5 Hz, 1H), 8.50-8.41 (m, 2H), 8.19-8.10 (m, 1H), 8.06 (dd, J=8.8, 3.1 Hz, 1H), 7.71 (d, J=7.7 Hz, 1H), 7.62 (dd, J=8.3, 4.2 Hz, 1H), 7.29 (dd, J=19.5, 5.1 Hz, 2H), 7.10-6.96 (m, 2H), 4.93 (dd, J=14.7, 7.9 Hz, 1H), 4.12 (d, J=6.6 Hz, 1H), 3.27-3.15 (m, 2H), 2.60 (t, J=6.1 Hz, 1H), 2.30-2.17 (m, 1H), 2.05 (t, J=11.3 Hz, 1H), 1.92-1.77 (m, 2H), 1.69-1.57 (m, 2H), 1.34-1.19 (m, 9H), 0.89-0.77 (m, 9H).

ESI-MS $(M+H)^+$: 607.

Example 36

Compound A36

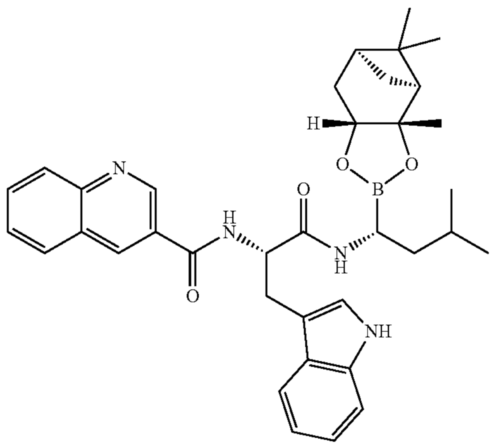

$^1H$ NMR (400 MHz, DMSO) δ 10.86 (s, 1H), 9.30-9.09 (m, 2H), 9.02 (dd, J=20.6, 8.2 Hz, 1H), 8.78 (dd, J=13.2, 2.0 Hz, 1H), 8.07 (t, J=7.9 Hz, 2H), 7.88 (t, J=7.7 Hz, 1H), 7.71

(t, J=7.6 Hz, 2H), 7.37-7.23 (m, 2H), 7.11-6.95 (m, 2H), 4.93 (dd, J=8.6, 5.4 Hz, 1H), 4.14 (t, J=6.4 Hz, 1H), 3.24 (ddd, J=15.1, 9.6, 5.4 Hz, 2H), 2.60 (t, J=6.5 Hz, 1H), 2.23 (s, 1H), 2.02 (d, J=6.1 Hz, 1H), 1.90-1.77 (m, 2H), 1.75-1.60 (m, 2H), 1.39 (t, J=10.2 Hz, 1H), 1.35-1.29 (m, 2H), 1.30-1.17 (m, 7H), 0.84 (ddd, J=10.5, 6.9, 4.5 Hz, 8H).

ESI-MS $(M+H)^+$: 607.

Example 37

Compound A37

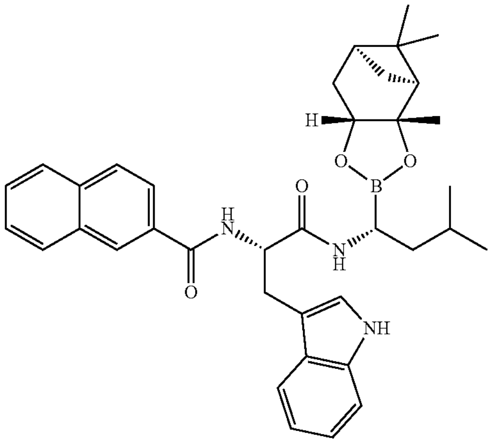

$^1$H NMR (400 MHz, DMSO) δ 10.86 (s, 1H), 9.23-9.12 (m, 1H), 8.77 (dd, J=19.8, 8.2 Hz, 1H), 8.42 (d, J=14.0 Hz, 1H), 8.04-7.94 (m, 3H), 7.89 (ddd, J=12.6, 8.6, 1.6 Hz, 1H), 7.72 (d, J=7.7 Hz, 1H), 7.66-7.56 (m, 2H), 7.36-7.25 (m, 2H), 7.04 (dt, J=14.8, 6.9 Hz, 2H), 4.97-4.82 (m, 1H), 4.18-4.06 (m, 1H), 3.25 (t, J=6.5 Hz, 2H), 2.59 (d, J=7.1 Hz, 1H), 2.29-2.17 (m, 1H), 2.04-1.98 (m, 1H), 1.91-1.76 (m, 2H), 1.73-1.60 (m, 2H), 1.37 (dd, J=22.5, 12.6 Hz, 3H), 1.29-1.21 (m, 7H), 0.84 (ddd, J=11.4, 7.0, 4.0 Hz, 9H).

ESI-MS $(M+H)^+$: 606.

Example 38

Compound A38

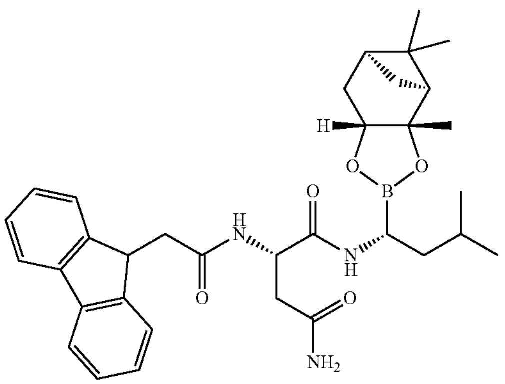

$^1$H NMR (400 MHz, DMSO) δ 8.84 (t, J=19.4 Hz, 1H), 8.30 (dd, J=23.1, 7.9 Hz, 1H), 7.86 (d, J=7.5 Hz, 2H), 7.54 (t, J=8.1 Hz, 2H), 7.33 (dtd, J=25.0, 7.3, 2.7 Hz, 5H), 6.97 (s, 1H), 4.90 (dd, J=13.1, 8.1 Hz, 1H), 4.33 (t, J=7.3 Hz, 1H), 4.10 (d, J=6.7 Hz, 1H), 2.63 (dd, J=14.7, 7.0 Hz, 2H), 2.57-2.51 (m, 1H), 2.49-2.40 (m, 2H), 2.25-2.16 (m, 1H), 2.00 (dd, J=14.8, 6.9 Hz, 1H), 1.86 (t, J=5.6 Hz, 1H), 1.79 (s, 1H), 1.72 (dd, J=13.6, 6.9 Hz, 1H), 1.64 (d, J=13.6 Hz, 1H), 1.38-1.28 (m, 3H), 1.23 (s, 5H), 0.84 (dd, J=17.2, 8.0 Hz, 10H).

ESI-MS $(M+Na)^+$: 608.2.

Example 39

Compound A39

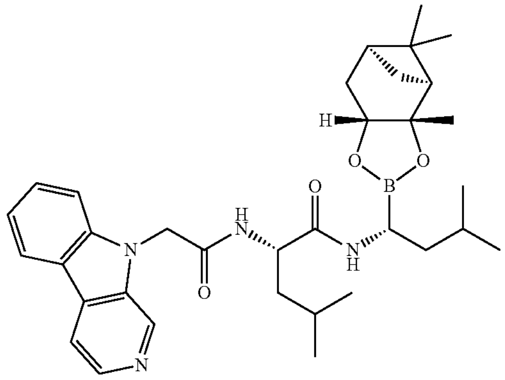

Compound A39 was synthesized as follows:

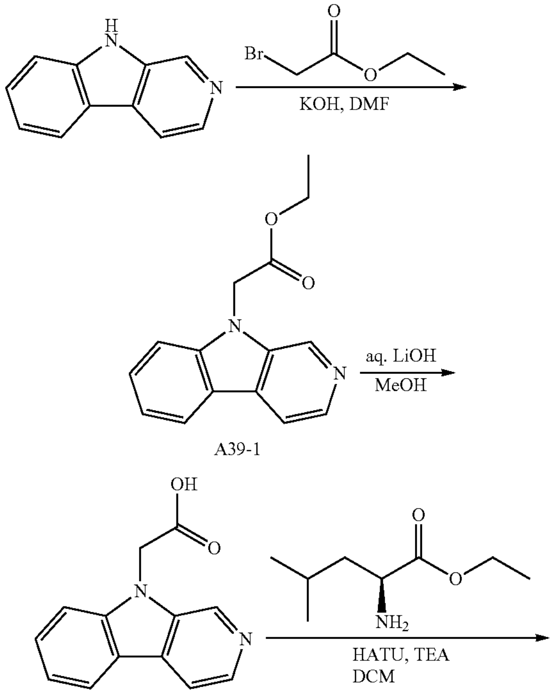

A39-2

-continued

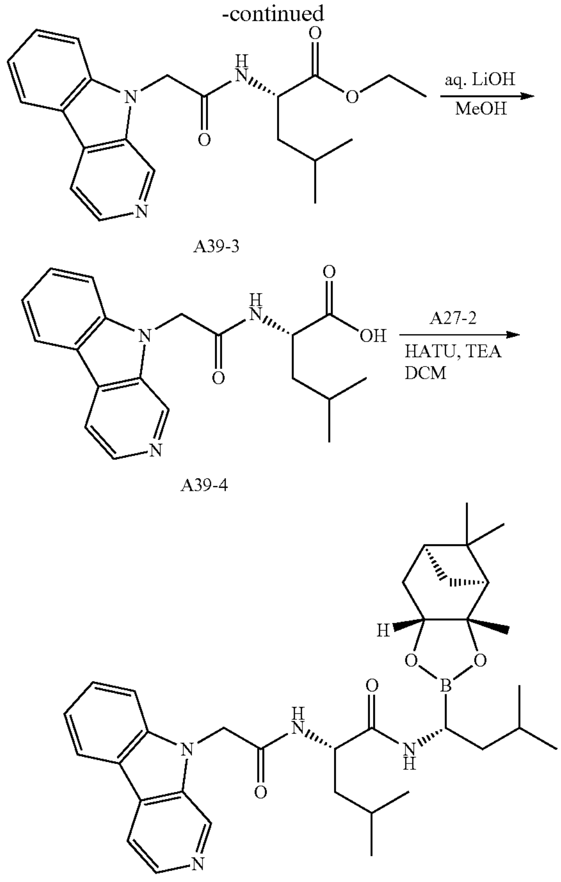

A39-3

A39-4

A39

1. Synthesis of Intermediate A39-1

9H-pyrido[3,4-b]indole (3 g, 18 mmol) was dissolved in N,N-dimethylformamide (DMF) (25 mL), potassium hydroxide solid (3 g, 54 mmol) was added at low temperature. The reaction was carried out at room temperature for 1 h. Ethyl bromoacetate (7.4 g, 45 mmol) was added, and the reaction was carried out at room temperature for 16 h. TLC showed that the reaction of the raw materials was complete. After adding water, it was extracted with ethyl acetate (80 mL*3), the organic phases were combined, and the solvent was spin-dried to obtain yellow solid compound A39-1 (1 g, yield 22%).

2. Synthesis of Intermediate A39-2

A39-1 (lg, 4 mmol) was dissolved in MeOH (15 mL), and LiGH (6 mL, 1M) aqueous solution was added at low temperature. The mixture was reacted at room temperature for 2 h. TLC showed that the raw materials were completely reacted. The solvent was spin-dried, and diluted hydrochloric acid was added to adjust the pH to 3-4. The mixture was extracted with ethyl acetate (20 mL*3), the organic phases were combined, and the solvent was spin-dried to obtain compound A39-2 (790 mg, yield 88%).

3. Synthesis of Intermediate A39-3

A39-2 (225 mg, 1 mmol) and L-leucine ethyl ester (353 mg, 1.8 mmol) were dissolved in DCM (4 mL), and HATU (760 mg, 2 mmol) and TEA (350 mg, 3.5 mmol) were added. The mixture was reacted at room temperature for 2 hours. After adding water, the mixture was extracted with DCM (20 mL*3). The organic phases were combined, and after the solvent was spin-dried, the organic phases were purified with prep-TLC to obtain white solid compound A39-3 (160 mg, yield 44%).

4. Synthesis of Intermediate A39-4

A39-3 (160 mg, 0.44 mmol) was dissolved in MeOH (4 mL), and LiGH (1 mL, 1M) aqueous solution was added at low temperature and the mixture was reacted at room temperature for 2 h. TLC showed that the raw materials were completely reacted. The solvent was spin-dried, and diluted hydrochloric acid was added to adjust the pH to 3-4. The mixture was extracted with ethyl acetate (10 mL*3), the organic phases were combined, and the solvent was spin-dried to obtain compound A39-4 (110 mg, yield 74%).

5. Synthesis of Compound A39

A39-4 (100 mg, 0.3 mmol) and A1-2 (170 mg, 0.45 mmol) were dissolved in DCM (3 mL), and HATU (230 mg, 0.6 mmol) and TEA (120 mg, 1.2 mmol) were added and the mixture was reacted at room temperature for 2 hours. After adding water, the mixture was extracted with DCM (15 mL*3). The organic phases were combined, and after the solvent was spin-dried, the crude product was purified by medium pressure preparative liquid chromatography to obtain a white solid compound A39 (12 mg, yield 6.8%).

$^1$H NMR (400 MHz, DMSO) δ 9.01 (s, 1H), 8.96 (s, 1H), 8.78 (d, J=8.3 Hz, 1H), 8.38 (d, J=5.2 Hz, 1H), 8.30-8.24 (m, 2H), 8.13 (d, J=5.2 Hz, 1H), 7.65-7.53 (m, 2H), 7.29 (t, J=7.3 Hz, 1H), 5.22 (q, J=16.9 Hz, 2H), 4.43 (dd, J=14.3, 8.9 Hz, 1H), 4.10 (d, J=6.7 Hz, 1H), 2.55 (d, J=8.8 Hz, 1H), 2.27-2.16 (m, 1H), 2.08-1.95 (m, 2H), 1.85 (t, J=5.6 Hz, 1H), 1.81 (d, J=5.5 Hz, 1H), 1.65 (dd, J=16.6, 9.4 Hz, 4H), 1.58-1.40 (m, 3H), 1.33 (d, J=10.1 Hz, 1H), 1.28 (s, 4H), 1.22 (d, J=9.9 Hz, 6H), 0.93-0.89 (m, 3H), 0.83 (dd, J=9.6, 4.4 Hz, 12H).

ESI-MS $(M+H)^+$: 545.

The synthesis method of compound A40-A41 is the same as that of A39, except that the 9H-pyrido[3,4-b]indole in the first step was replaced with the corresponding amine.

Example 40

Compound A40

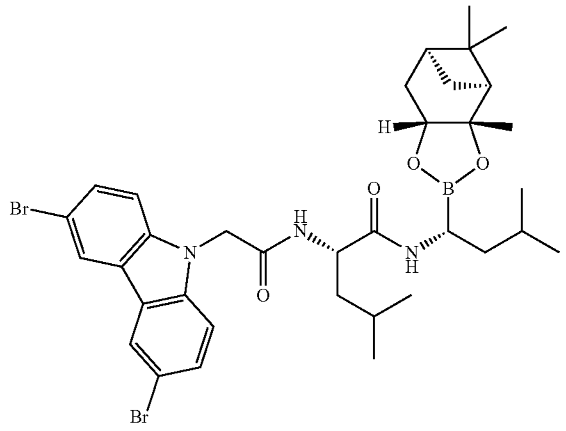

$^1$H NMR (400 MHz, DMSO) δ 8.92 (d, J=2.9 Hz, 1H), 8.63 (d, J=8.1 Hz, 1H), 8.48 (d, J=1.8 Hz, 2H), 7.57 (dt, J=18.6, 5.3 Hz, 4H), 5.11 (d, J=19.7 Hz, 2H), 4.41 (dd, J=14.4, 8.8 Hz, 1H), 4.10 (d, J=6.8 Hz, 1H), 1.86 (s, 2H), 1.64 (d, J=13.7 Hz, 5H), 1.39-1.25 (m, 7H), 1.23 (d, J=9.3 Hz, 5H), 0.91 (d, J=6.6 Hz, 3H), 0.88-0.75 (m, 12H).

ESI-MS $(M+H)^+$: 744.

Example 41

Compound A41

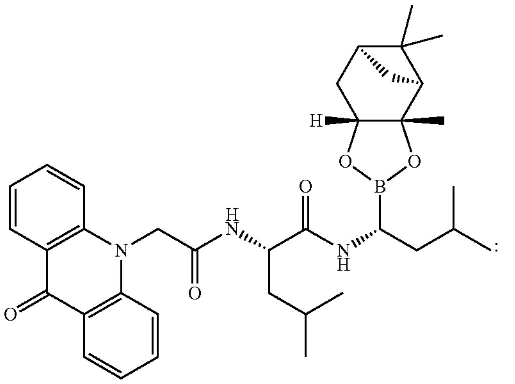

$^1H$ NMR (400 MHz, DMSO) δ 8.96 (s, 1H), 8.73 (d, J=7.9 Hz, 1H), 8.35 (dd, J=8.0, 1.5 Hz, 2H), 7.77 (t, J=7.0 Hz, 2H), 7.61 (s, 2H), 7.35 (s, 2H), 5.24 (s, 2H), 4.52-4.43 (m, 1H), 4.12 (d, J=6.8 Hz, 1H), 2.58 (s, 1H), 2.22 (d, J=11.3 Hz, 1H), 2.01 (dd, J=14.4, 7.0 Hz, 3H), 1.87 (t, J=5.6 Hz, 1H), 1.83 (d, J=6.2 Hz, 1H), 1.66 (d, J=13.8 Hz, 3H), 1.59-1.44 (m, 3H), 1.35-1.25 (m, 6H), 0.93 (d, J=6.6 Hz, 3H), 0.85 (dd, J=6.5, 4.0 Hz, 12H).

ESI-MS $(M+H)^+$: 614.

Example 42

Compound A42

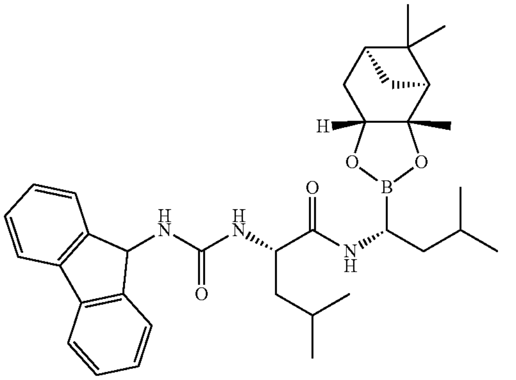

Compound A42 was synthesized as follows:

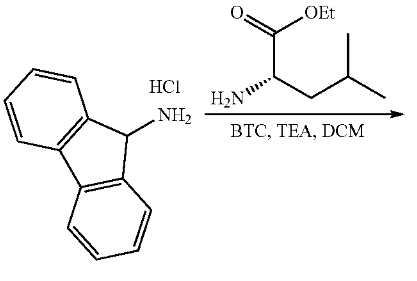

-continued

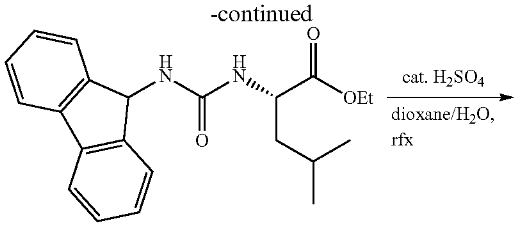

A42-1

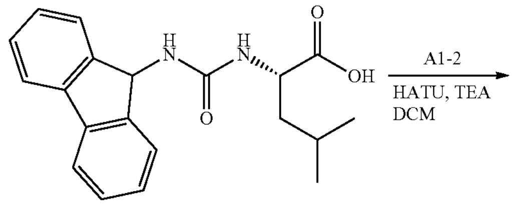

A42-2

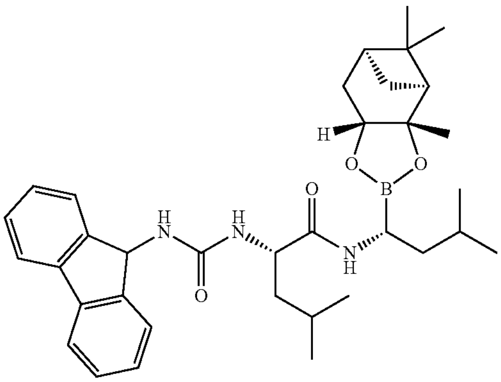

A42

1. Synthesis of Intermediate A42-1

9-Aminofluorene hydrochloride (1 g, 4.60 mmol) was dissolved in 20 mL of dichloromethane, and triethylamine (1.91 mL) and triphosgene (550 mg, 1.85 mmol) were sequentially added under ice bath. After stirring for 30 min L-leucine ethyl ester (920 mg, 5.04 mmol) was added thereto. After reacting at room temperature for 1 hour, the reaction was quenched by adding water (10 mL), and extracted with dichloromethane (20 mL*3). The organic phases were combined, dried and spin-dried. The solute was slurried with petroleum ether/ethyl acetate mixed solution, and then filtered to obtain a white solid (400 mg, 200 yield).

2. Synthesis of Intermediate A42-2

A42-1 (290 mg, 0.79 mmol) was dissolved in 10 mL of dioxane/water (10:1), and one drop of concentrated sulfuric acid was added. After refluxing overnight, it was cooled to room temperature. The mixture was diluted with 20 mL ofwater. The aqueous phase was extracted with ethyl acetate (20 mL*3) and then combined, dried and spin-dried to obtain a white solid (200 mg, 7400 yield).

3. Synthesis of Compound A42

Compound A42-2 (200 mg, 0.59 mmol) was dissolved in dichloromethane (20 mL), HATU (340 mg, 0.89 mmol), A1-2 (190 mg, 0.71 mmol) and triethylamine (0.3 mL) were added in sequence. After reacting at room temperature for 3 hours, the mixture was diluted with water (20 mL). The aqueous phase was extracted with dichloromethane (20 mL*3). The organic phases were combined, dried and spin-dried, and the solute was purified by medium pressure preparative liquid chromatography to obtain a white solid (45 mg, 13% yield).

$^1$H NMR (400 MHz, DMSO) δ 9.16 (s, 1H), 7.84 (d, J=7.5 Hz, 2H), 7.51 (d, J=7.4 Hz, 2H), 7.41 (t, J=7.4 Hz, 2H), 7.31 (dt, J=9.8, 7.9 Hz, 2H), 6.55 (d, J=8.6 Hz, 1H), 6.13 (d, J=8.3 Hz, 1H), 5.82 (d, J=8.8 Hz, 1H), 4.45 (dd, J=15.3, 7.7 Hz, 1H), 4.07 (d, J=6.5 Hz, 1H), 2.56 (s, 1H), 2.21 (d, J=11.2 Hz, 1H), 2.00 (dd, J=14.3, 6.8 Hz, 3H), 1.85 (t, J=5.5 Hz, 1H), 1.78 (s, 1H), 1.64 (d, J=11.4 Hz, 2H), 1.50-1.35 (m, 4H), 1.26 (t, J=11.7 Hz, 11H), 0.90 (dd, J=17.8, 6.5 Hz, 10H).

ESI-MS (M+Na)$^+$: 608.

Example 43

Compound A43

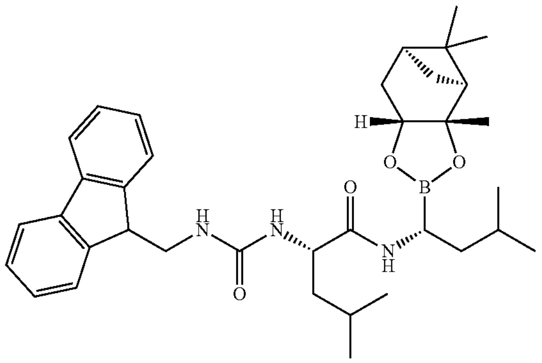

Compound A43 was synthesized as follows:

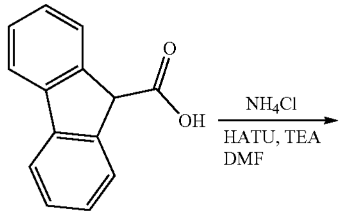

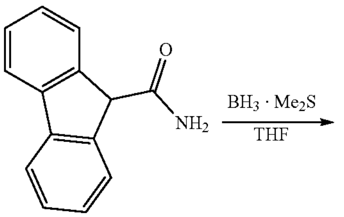

A43-1

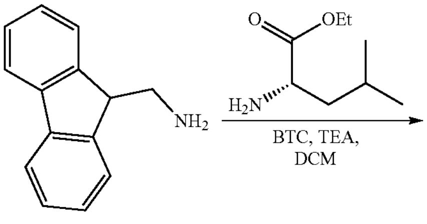

A43-2

-continued

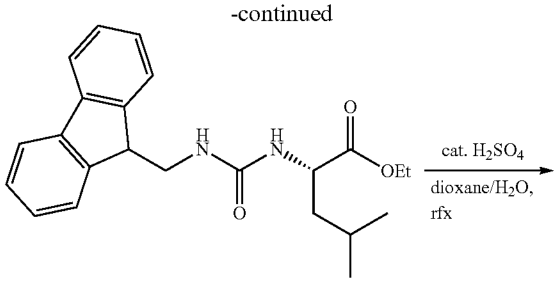

A43-3

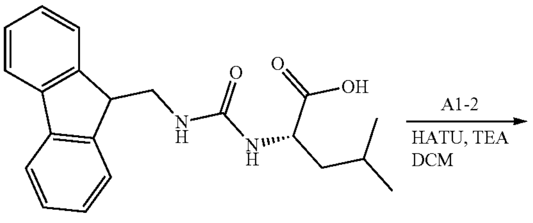

A43-4

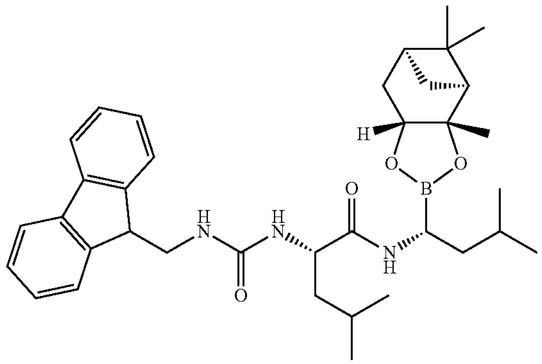

A43

1. Synthesis of Intermediate A43-1

9-Fluorenic acid (10 g, 47.6 mmol) was dissolved in 50 mL DMF, and HATU (27 g, 71.0 mmol), ammonium chloride (25.5 g, 476.6 mmol) and triethylamine (66 mL) were added in sequence. After reacting at room temperature for 48 hours, the mixture was diluted with water (200 mL). The aqueous phase was extracted with ethyl acetate (30 mL*3). The organic phases were combined, dried and spin-dried, and the solute was purified by column to obtain a white solid (1.6 g, 16% yield).

2. Synthesis of Intermediate A43-2

A43-1 (1.4 g, 6.69 mmol) was dissolved in 20 mL THF, and borane dimethyl sulfide solution (BH3.Me2S) (10M, 1.35 mL) was added and the mixture was refluxed for 3 h. After cooling to room temperature, the reaction was quenched with 1M HCl. The aqueous phase was basified with saturated sodium bicarbonate solution and extracted with ethyl acetate (20 mL*3). The organic phases were combined, dried and spin-dried, and the solute was purified by column to obtain a pale yellow solid (540 mg, 41% yield).

3. Synthesis of Intermediate A43-3

A43-2 (540 mg, 2.77 mmol) was dissolved in 10 mL of dichloromethane, and triethylamine (1.15 mL) and triphosgene (330 mg, 1.11 mmol) were sequentially added under ice bath. After stirring for 30 min, L-leucine ethyl ester (590 mg, 3.01 mmol) was added. After reacting at room temperature for 1 hour, the reaction was quenched by adding water (10 mL), and extracted with dichloromethane (20 mL*3).

The organic phases were combined, dried and spin-dried, and the solute was slurried with petroleum ether/ethyl acetate mixed solution, and then filtered to obtain a white solid (850 mg, 80% yield).

4. Synthesis of Intermediate A43-4

A43-3 (370 mg, 0.97 mmol) was dissolved in 10 mL of dioxane/water (10:1), and one drop of concentrated sulfuric acid was added. After refluxing overnight, it was cooled to room temperature. The mixture was diluted with 20 mL of water. The aqueous phase was extracted with ethyl acetate (20 mL*3) and then combined, dried and spin-dried to obtain a white solid (240 mg, 70% yield).

5. Synthesis of Compound A43

Compound A43-4 (240 mg, 0.68 mmol) was dissolved in dichloromethane (20 mL), and HATU (460 mg, 1.21 mmol), A27-2 (250 mg, 0.94 mmol) and triethylamine (0.4 mL) were added in sequence. After reacting at room temperature for 3 hours, it was diluted with water (20 mL). The aqueous phase was extracted with dichloromethane (20 mL*3). The organic phases were combined, dried and spin-dried, and the solute was purified by medium pressure preparative liquid chromatography to obtain a white solid (70 mg, 11% yield).

$^1$H NMR (400 MHz, DMSO) δ 9.11 (s, 1H), 7.87 (d, J=7.5 Hz, 2H), 7.60 (t, J=6.7 Hz, 2H), 7.39 (td, J=7.3, 2.6 Hz, 2H), 7.31 (ddd, J=15.0, 7.5, 3.8 Hz, 2H), 6.30 (d, J=8.5 Hz, 1H), 6.20 (t, J=5.7 Hz, 1H), 4.31 (dd, J=14.9, 8.5 Hz, 1H), 4.05 (dd, J=12.1, 6.6 Hz, 2H), 3.52-3.36 (m, 2H), 2.23-2.13 (m, 1H), 2.05-1.92 (m, 2H), 1.80 (dd, J=14.0, 8.0 Hz, 2H), 1.72-1.32 (m, 6H), 1.19 (d, J=13.5 Hz, 6H), 0.84 (ddd, J=13.9, 12.1, 7.0 Hz, 17H).

ESI-MS $(M+Na)^+$: 622.1.

Example 44

Compound A44

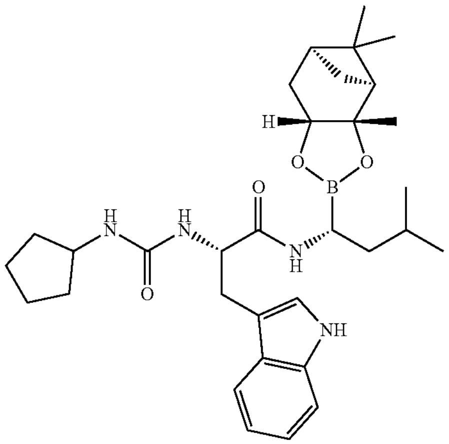

Compound A44 was synthesized as follows:

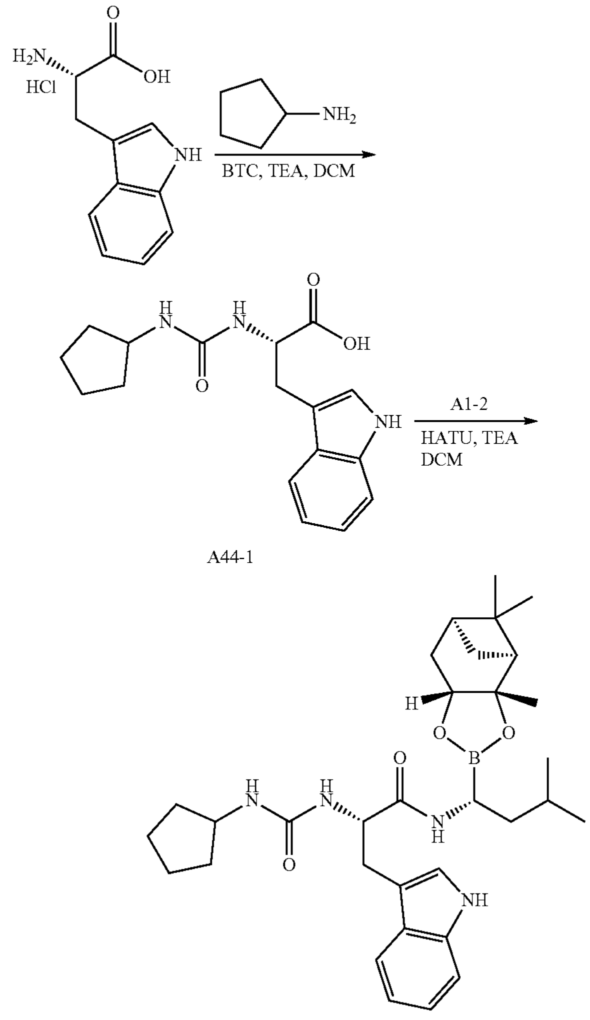

A44-1

A44

1. Synthesis of Intermediate A44-1

Cyclopentylamine (115 mg, 1.35 mmol) was dissolved in 10 mL of dichloromethane, and triethylamine (270 mg, 2.67 mmol) and triphosgene (160 mg, 0.54 mmol) were added sequentially under ice bath. After reacting for 30 min, L-tryptophan hydrochloride (325 mg, 1.35 mmol) was added. After reacting at room temperature for 1 hour, 1M HCl was added to adjust to acidity. The mixture was extracted with dichloromethane (20 mL*3). The organic phases were combined, dried and spin-dried to obtain a crude product (260 mg, 60%).

2. Synthesis of Compound A44

A44-1 (260 mg, 0.82 mmol) was dissolved in 15 mL of dichloromethane, and HATU (470 mg, 1.23 mmol), A1-2 (260 mg, 0.98 mmol) and triethylamine (125 mg, 1.24 mmol) were sequentially added thereto. After reacting at room temperature for 2 hours, it was diluted with water (10 mL). The organic phase was extracted with dichloromethane (10 mL*3) and then combined, dried and spin-dried. The solute was purified by medium pressure preparative liquid chromatography to obtain a white solid (70 mg, 15% yield).

$^1$H NMR (400 MHz, DMSO) δ 10.89 (s, 1H), 9.02 (s, 1H), 7.57 (d, J=8.0 Hz, 1H), 7.31 (d, J=8.1 Hz, 1H), 7.14-7.02 (m,

2H), 6.97 (t, J=7.0 Hz, 1H), 6.09 (d, J=7.3 Hz, 1H), 5.85 (d, J=8.3 Hz, 1H), 4.52 (dd, J=14.9, 7.0 Hz, 1H), 4.08 (d, J=6.6 Hz, 1H), 3.80 (dd, J=13.2, 6.5 Hz, 1H), 3.07-2.89 (m, 2H), 2.49-2.45 (m, 2H), 2.27-2.15 (m, 1H), 2.00 (d, J=7.7 Hz, 1H), 1.85 (t, J=5.6 Hz, 1H), 1.79 (s, 1H), 1.77-1.62 (m, 3H), 1.61-1.42 (m, 5H), 1.37 (d, J=9.9 Hz, 1H), 1.25-1.15 (m, 8H), 0.82 (dd, J=11.9, 9.4 Hz, 10H).

ESI-MS $(M+Na)^+$: 585.1.

The synthesis method of compound A45 is the same as that of A44, except that raw material cyclopentylamine in the first step was replaced with cyclopentanol.

Example 45

Compound A45

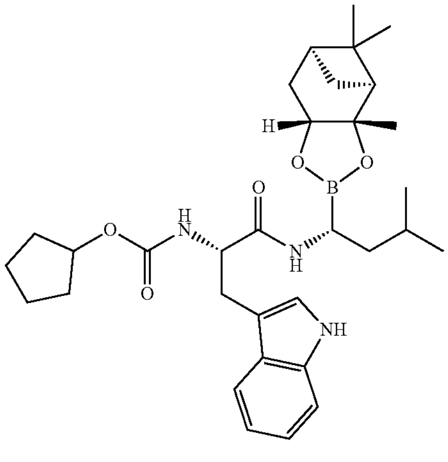

$^1$H NMR (400 MHz, DMSO) δ 10.87 (s, 1H), 9.05 (s, 1H), 7.60 (d, J=7.7 Hz, 1H), 7.32 (d, J=8.1 Hz, 1H), 7.24-7.12 (m, 2H), 7.06 (t, J=7.5 Hz, 1H), 6.98 (t, J=7.4 Hz, 1H), 4.86 (s, 1H), 4.42-4.18 (m, 1H), 4.09 (d, J=7.0 Hz, 1H), 3.09-2.88 (m, 2H), 2.51 (s, 1H), 2.27-2.16 (m, 1H), 2.02-1.94 (m, 1H), 1.85 (t, J=5.6 Hz, 1H), 1.80 (s, 1H), 1.76-1.40 (m, 10H), 1.37 (d, J=9.9 Hz, 1H), 1.26-1.17 (m, 7H), 0.86-0.79 (m, 9H).

ESI-MS $(M+Na)^+$: 586.2.

Example 46

Compound A46

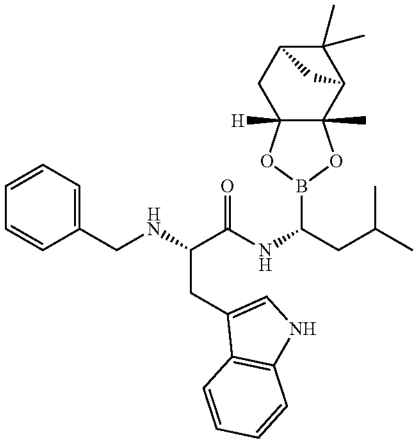

Compound A46 was synthesized as follows

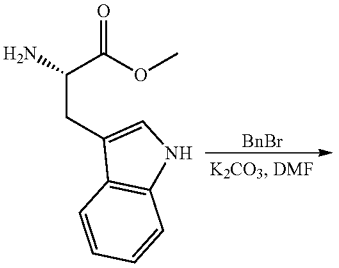

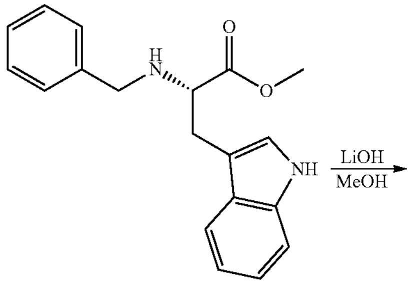

A46-1

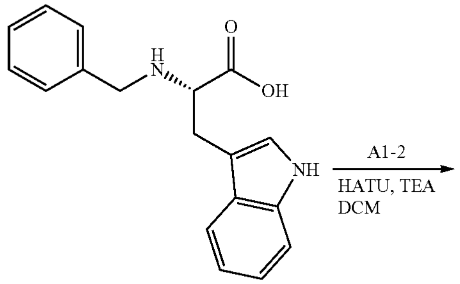

A46-2

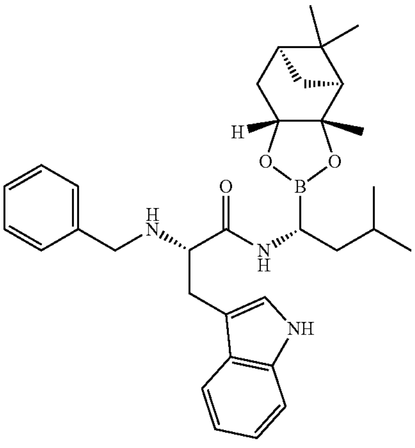

A46

1. Synthesis of Intermediate A46-1

L-tryptophan methyl ester (500 mg, 2.29 mmol), benzyl bromide (550 mg, 3.21 mmol) and potassium carbonate (640 mg, 4.64 mmol) were dissolved in 10 mL DMF. After reacting at room temperature for 2 hours, the mixture was diluted with 100 mL water. The aqueous phase was extracted with ethyl acetate (20 mL*3). The organic phases were combined, dried, spin-dried, and purified with a preparation plate to obtain a white solid (420 mg, 59% yield).

2. Synthesis of Intermediate A46-2

A46-1 (420 mg, 1.36 mmol) and LiGH (120 mg, 2.72 mmol) were dissolved in methanol/water (3:1, 24 mL). After reacting at 70° C. for 2 hours, the methanol was spun off, and the aqueous phase was adjusted to acidity with 2M HCl. The obtained solid was filtered to obtain a white solid (350 mg, 87% yield).

3. Synthesis of Compound A46

A46-2 (350 mg, 1.19 mmol) was dissolved in 15 mL of dichloromethane, and HATU (680 mg, 1.78 mmol), A1-2 (380 mg, 1.43 mmol) and triethylamine (580 mg, 5.74 mmol) were added sequentially. After reacting at room temperature for 2 hours, it was diluted with water (10 mL). The organic phase was extracted with dichloromethane (10 mL*3) and then combined, dried and spin-dried. The solute was purified by medium pressure preparative liquid chromatography to obtain a white solid (180 mg, 27% yield).

$^1$H NMR (400 MHz, DMSO) δ 10.89 (s, 1H), 9.03 (s, 1H), 7.52 (d, J=7.8 Hz, 1H), 7.35-7.17 (m, 7H), 7.14 (d, J=2.2 Hz, 1H), 7.05 (t, J=7.0 Hz, 1H), 6.95 (t, J=7.0 Hz, 1H), 4.09 (d, J=6.7 Hz, 1H), 3.69 (dd, J=13.2, 4.9 Hz, 1H), 3.61-3.55 (m, 1H), 3.51 (d, J=7.2 Hz, 1H), 3.01 (tt, J=14.2, 6.9 Hz, 2H), 2.44 (d, J=7.6 Hz, 1H), 2.21 (s, 2H), 1.86 (t, J=5.5 Hz, 1H), 1.79 (s, 1H), 1.65 (d, J=13.9 Hz, 1H), 1.49 (ddd, J=48.1, 21.7, 8.6 Hz, 3H), 1.29 (s, 4H), 1.16 (d, J=7.5 Hz, 2H), 0.81 (dd, J=19.4, 8.4 Hz, 10H).

ESI-MS $(M+H)^+$: 542.2.

Example 47

Compound A47

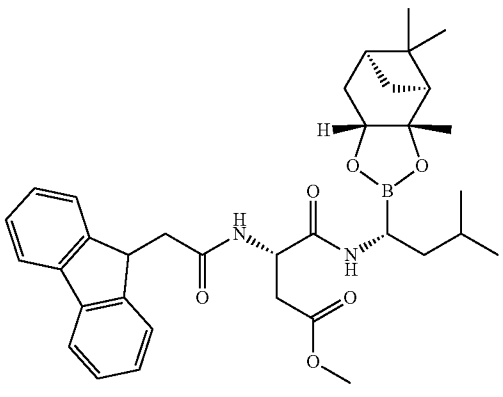

Compound A47 was synthesized as follows

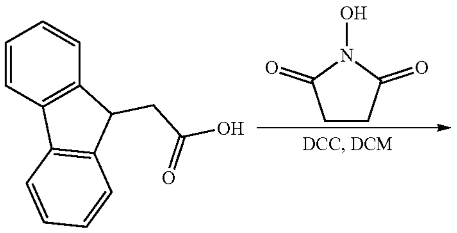

-continued

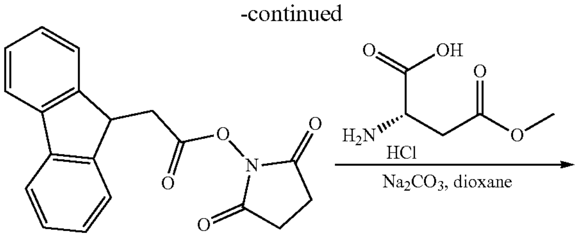

A47-1

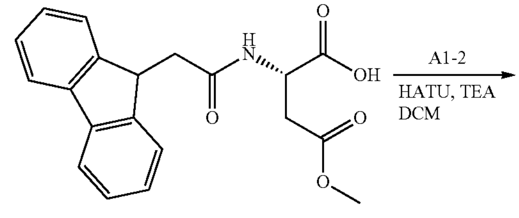

A47-2

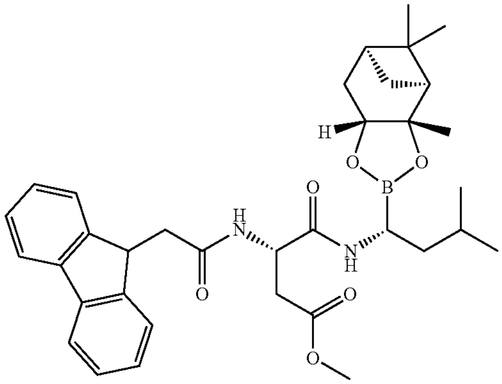

A47

1. Synthesis of Intermediate A47-1

9-Fluoreneacetic acid (500 mg, 2.23 mmol), N-hydroxysuccinimide (256 mg, 2.23 mmol) and DCC (460 mg, 2.23 mmol) were dissolved in 20 mL of dichloromethane. After reacting overnight at room temperature, the mixture was filtered. The filtrate was spin-dried, and the solute was purified with prep-TLC to obtain a white solid (850 mg, 100%).

2. Synthesis of Intermediate A47-2

L-aspartic acid-beta-methyl ester hydrochloride (490 mg, 2.66 mmol) and sodium carbonate (850 mg, 7.94 mmol) were dissolved in dioxane/water (3.1, 16 mL), and A47-1 (850 mg, 2.33 mmol) was added under ice bath. After reacting overnight at room temperature, the solvent was spin-dried. The aqueous phase was adjusted to acidity with 2M HCl and extracted with ethyl acetate (20 mL*3). The organic phases were combined, dried and spin-dried to obtain a pale yellow solid (690 mg, 83% yield).

3. Synthesis of Compound A47

A47-2 (690 mg, 1.95 mmol) was dissolved in 25 mL of dichloromethane, and HATU (1120 mg, 2.93 mmol), A1-2 (620 mg, 2.34 mmol) and triethylamine (950 mg, 9.45 mmol) were added sequentially. After reacting at room temperature for 2 hours, it was diluted with water (20 mL). The organic phase was extracted with dichloromethane (20 mL*3), and then combined, dried and spin-dried. The solute was purified by medium pressure preparative liquid chromatography to obtain a white solid (140 mg, 11% yield).

$^1$H NMR (400 MHz, DMSO) δ 8.65 (d, J=3.8 Hz, 1H), 8.37 (d, J=8.2 Hz, 1H), 7.86 (d, J=7.5 Hz, 2H), 7.53 (dd,

J=19.1, 7.6 Hz, 2H), 7.38 (t, J=7.3 Hz, 2H), 7.29 (t, J=6.9 Hz, 2H), 4.91 (dd, J=13.6, 8.1 Hz, 1H), 4.35 (t, J=7.4 Hz, 1H), 4.15 (d, J=6.7 Hz, 1H), 3.61 (d, J=4.4 Hz, 3H), 2.77-2.58 (m, 4H), 2.46 (d, J=8.1 Hz, 1H), 2.27-2.18 (m, 1H), 2.00 (dd, J=14.5, 6.9 Hz, 1H), 1.88 (t, J=5.6 Hz, 1H), 1.80 (s, 1H), 1.68 (dd, J=22.6, 10.3 Hz, 2H), 1.40-1.24 (m, 8H), 0.84 (dd, J=17.5, 8.9 Hz, 10H).

ESI-MS $(M+Na)^+$:623.2.

The synthesis method of compound A48 is the same as that of A47, except that the raw material L-aspartic acid-beta-methyl ester was replaced with L-asparagine or $N^4$-methyl-L-asparagine.

Example 48

Compound A48

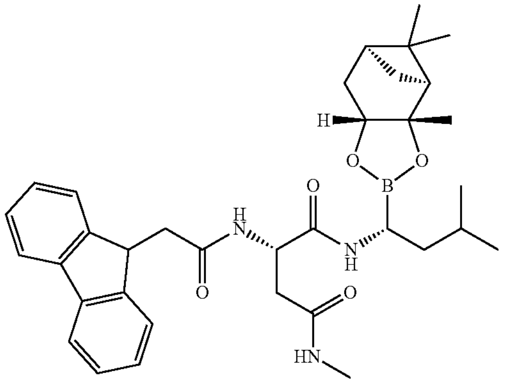

$^1$H NMR (400 MHz, DMSO) δ 8.84 (d, J=36.1 Hz, 1H), 8.26 (d, J=6.9 Hz, 1H), 7.85 (d, J=6.7 Hz, 2H), 7.78 (s, 1H), 7.61-7.46 (m, 2H), 7.37 (s, 2H), 7.29 (s, 2H), 4.93 (s, 1H), 4.34 (s, 1H), 4.10 (d, J=7.4 Hz, 1H), 2.56 (d, J=15.2 Hz, 7H), 1.86 (ddd, J=65.9, 58.1, 43.7 Hz, 10H), 1.38 (d, J=55.7 Hz, 3H), 1.03-0.65 (m, 12H).

ESI-MS $(M+Na)^+$: 622.2.

Example 49

Compound A49

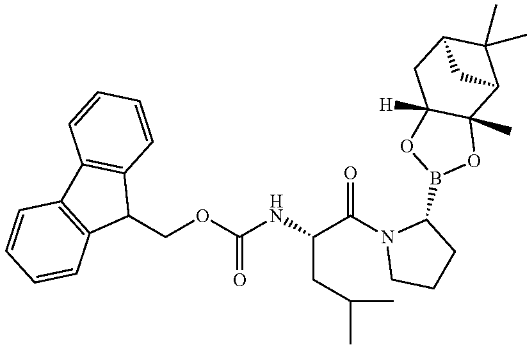

Compound A49 was synthesized as follows:

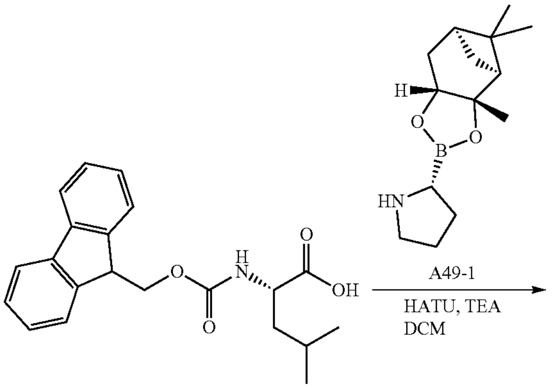

A22-1

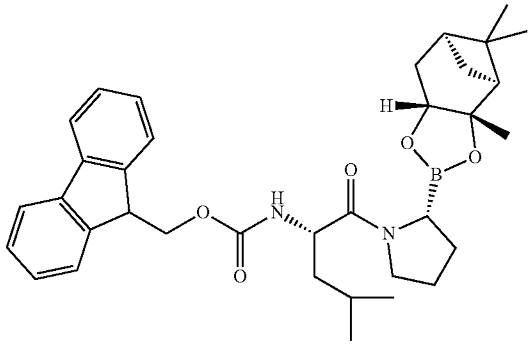

A49

A22-1 (210 mg, 0.59 mmol) was dissolved in 5 mL of dichloromethane, and HATU (340 mg, 0.89 mmol), A49-1 (229 mg, 0.80 mmol) and triethylamine (180 mg, 1.78 mmol) were added sequentially. After reacting at room temperature for 2 hours, it was diluted with water (10 mL). The organic phase was extracted with dichloromethane (10 mL*3) and then combined, dried and spin-dried. The solute was purified by medium pressure preparative liquid chromatography to obtain a white solid (180 mg, 52% yield).

$^1$H NMR (400 MHz, DMSO) δ 7.90 (d, J=7.5 Hz, 2H), 7.73 (d, J=7.5 Hz, 2H), 7.68 (d, J=8.2 Hz, 1H), 7.42 (t, J=7.3 Hz, 2H), 7.37-7.28 (m, 2H), 4.33-4.12 (m, 5H), 3.66 (t, J=8.4 Hz, 1H), 3.38 (s, 1H), 2.90 (dd, J=10.5, 6.6 Hz, 1H), 2.33-2.21 (m, 1H), 2.09-1.99 (m, 2H), 1.96-1.80 (m, 4H), 1.73-1.55 (m, 3H), 1.53-1.44 (m, 1H), 1.37 (td, J=8.6, 4.3 Hz, 1H), 1.31 (s, 3H), 1.28-1.19 (m, 5H), 0.89 (dd, J=11.1, 6.6 Hz, 5H), 0.80 (d, J=13.1 Hz, 3H).

ESI-MS $(M+H)^+$: 584.

Example 50

Compound A50

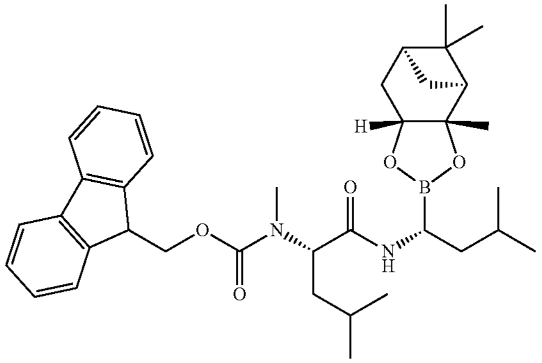

Compound A50 was synthesized as follows

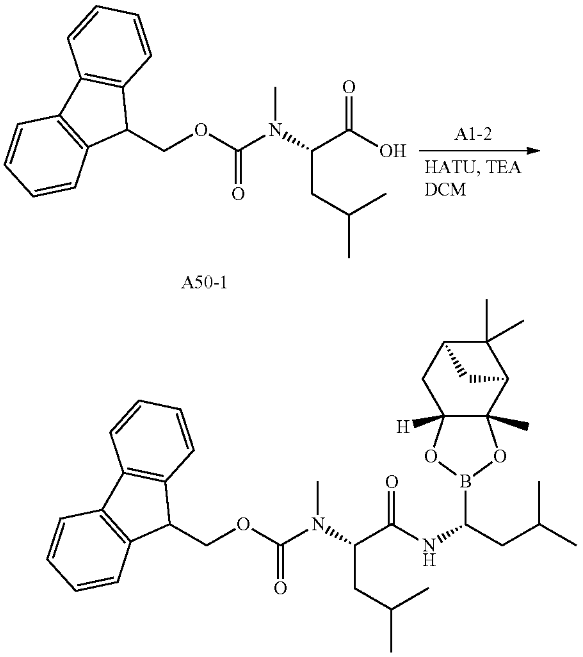

A50-1

A50

A50-1 (367 mg, 1 mmol) was dissolved in 5 mL of dichloromethane, and HATU (494 mg, 1.3 mmol), A1-2 (493 mg, 1.3 mmol) and triethylamine (303 mg, 3 mmol) were added sequentially. After reacting at room temperature for 2 hours, it was diluted with water (10 mL). The organic phase was extracted with dichloromethane (10 mL*3) and then combined, dried and spin-dried. The solute was purified by medium pressure preparative liquid chromatography to obtain a white solid (58 mg, 9% yield).

$^1$H NMR (400 MHz, DMSO) δ 9.06 (s, 1H), 7.92 (d, J=7.5 Hz, 2H), 7.64 (d, J=7.2 Hz, 2H), 7.44 (t, J=7.4 Hz, 2H), 7.35 (t, J=7.4 Hz, 2H), 4.77 (s, 1H), 4.46 (d, J=7.1 Hz, 1H), 4.33 (dt, J=17.2, 6.3 Hz, 2H), 4.10 (d, J=8.2 Hz, 1H), 2.74 (s, 3H), 2.21 (d, J=8.4 Hz, 1H), 2.03 (s, 1H), 1.83 (d, J=20.3 Hz, 2H), 1.62 (ddd, J=43.2, 20.8, 6.4 Hz, 4H), 1.39-1.28 (m, 3H), 1.25 (d, J=6.4 Hz, 7H), 0.97-0.75 (m, 15H).

ESI-MS $(M+H)^+$: 615.

Example 51

Compound A51

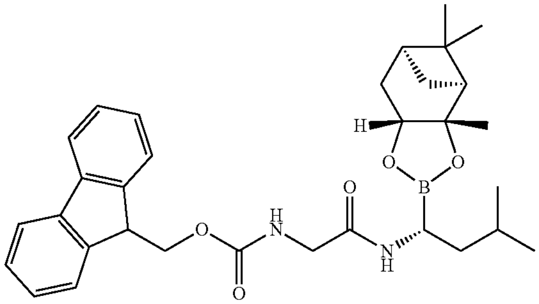

$^1$H NMR (400 MHz, DMSO) δ 8.84 (s, 1H), 7.89 (d, J=7.5 Hz, 2H), 7.71 (d, J=7.5 Hz, 2H), 7.65 (t, J=6.1 Hz, 1H), 7.42 (t, J=7.4 Hz, 2H), 7.33 (t, J=7.3 Hz, 2H), 4.34-4.16 (m, 3H), 4.06 (d, J=7.3 Hz, 1H), 3.75 (d, J=6.0 Hz, 2H), 2.56 (s, 1H), 2.23-2.13 (m, 1H), 2.05-1.96 (m, 1H), 1.83 (t, J=5.6 Hz, 1H), 1.80-1.73 (m, 1H), 1.72-1.58 (m, 2H), 1.36-1.27 (m, 2H), 1.22 (d, J=9.9 Hz, 7H), 0.89-0.73 (m, 9H).

The synthesis method of compound A51 is the same as that of compound A22.

Example 52

Compound A52

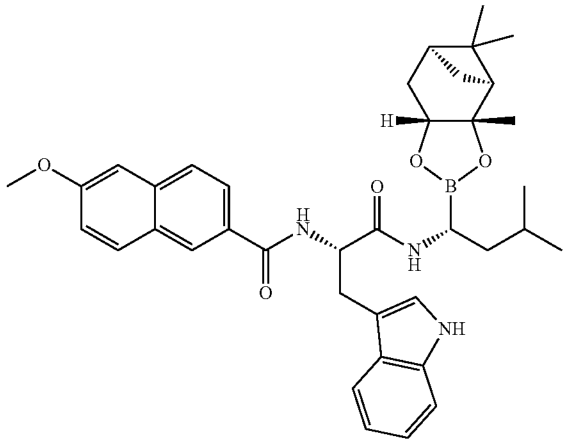

$^1$H NMR (400 MHz, DMSO) δ 10.83 (s, 1H), 9.11 (d, J=10.1 Hz, 1H), 8.61 (dd, J=22.6, 8.1 Hz, 1H), 8.33 (d, J=13.6 Hz, 1H), 7.94-7.80 (m, 3H), 7.69 (d, J=7.7 Hz, 1H), 7.36 (d, J=2.1 Hz, 1H), 7.34-7.19 (m, 3H), 7.08-6.98 (m, 2H), 4.95-4.84 (m, 1H), 4.14-4.07 (m, 1H), 3.89 (s, 3H), 3.24-3.18 (m, 2H), 2.61-2.55 (m, 1H), 2.27-2.16 (m, 1H), 2.06-1.97 (m, 1H), 1.89-1.76 (m, 2H), 1.72-1.60 (m, 2H), 1.38 (t, J=10.1 Hz, 1H), 1.32-1.21 (m, 8H), 0.85-0.80 (m, 9H).

The synthesis method of compound A52 is the same as that of compound A24.

Example 53

Compound A53

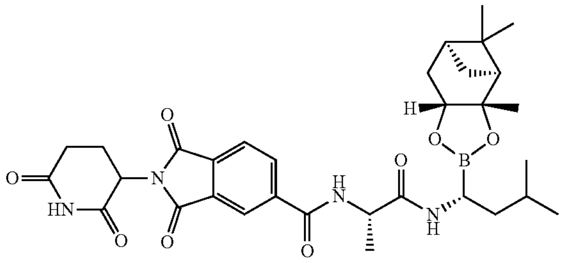

$^{1}$H NMR (400 MHz, DMSO) δ 11.14 (s, 1H), 9.07 (d, J=7.2 Hz, 1H), 8.95 (s, 1H), 8.44 (s, 1H), 8.34 (d, J=8.0 Hz, 1H), 8.08-7.98 (m, 1H), 5.20 (dd, J=12.9, 5.4 Hz, 1H), 4.63 (t, J=7.2 Hz, 1H), 4.08 (d, J=6.6 Hz, 1H), 2.98-2.84 (m, 1H), 2.70-2.52 (m, 3H), 2.25-2.16 (m, 1H), 2.13-2.05 (m, 1H), 2.04-1.97 (m, 1H), 1.84-1.72 (m, 2H), 1.73-1.57 (m, 2H), 1.38 (d, J=7.3 Hz, 3H), 1.33-1.25 (m, 3H), 1.22 (t, J=4.1 Hz, 6H), 0.89-0.74 (m, 9H).

The synthesis method of compound A53 is the same as that of compound A24.

Example 54

Compound A54

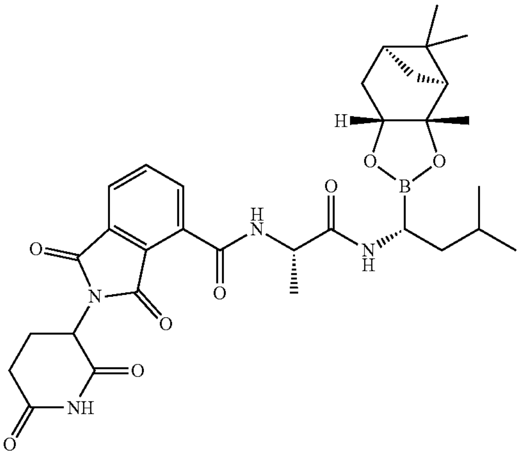

$^{1}$H NMR (400 MHz, DMSO) δ 11.15 (d, J=2.7 Hz, 1H), 9.29 (dd, J=22.3, 7.3 Hz, 1H), 8.76 (d, J=3.3 Hz, 1H), 8.08-7.91 (m, 3H), 5.20 (ddd, J=12.9, 5.3, 2.4 Hz, 1H), 4.64-4.56 (m, 1H), 4.12 (d, J=8.6 Hz, 1H), 2.98-2.82 (m, 1H), 2.68-2.52 (m, 3H), 2.27-2.18 (m, 1H), 2.13-1.97 (m, 2H), 1.86 (t, J=5.4 Hz, 1H), 1.83-1.75 (m, 1H), 1.71-1.58 (m, 2H), 1.36-1.32 (m, 4H), 1.28-1.19 (m, 8H), 0.87-0.78 (m, 9H).

The synthesis method of compound A54 is the same as that of compound A24.

Example 55

Compound A55

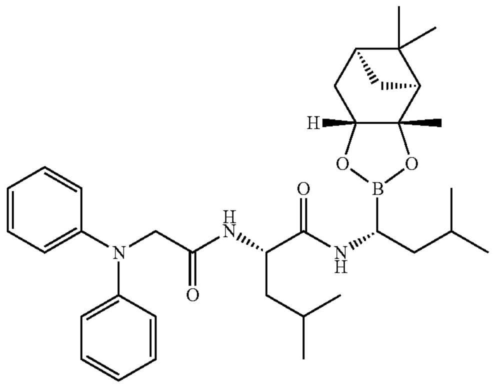

$^{1}$H NMR (400 MHz, DMSO) δ 8.92-8.79 (m, 1H), 8.25-8.12 (m, 1H), 7.24 (t, J=7.9 Hz, 4H), 7.03-6.89 (m, 6H), 4.48-4.38 (m, 1H), 4.38-4.29 (m, 2H), 4.12-4.05 (m, 1H), 2.57-2.51 (m, 1H), 2.24-2.16 (m, 1H), 2.05-1.97 (m, 1H), 1.84 (t, J=5.5 Hz, 1H), 1.80-1.75 (m, 1H), 1.71-1.60 (m, 2H), 1.54-1.38 (m, 3H), 1.36-1.29 (m, 1H), 1.28-1.20 (m, 8H), 0.87-0.72 (m, 15H).

The synthesis method of compound A55 is the same as that of compound A39.

Example 56

Compound A56

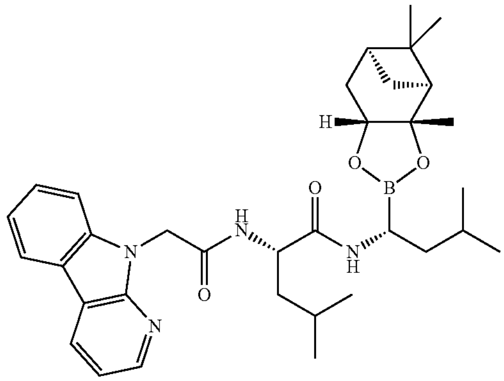

$^{1}$H NMR (400 MHz, DMSO) δ 8.94-8.82 (m, 1H), 8.65-8.53 (m, 2H), 8.44-8.42 (m, 1H), 8.21 (d, J=7.7 Hz, 1H), 7.54-7.39 (m, 2H), 7.31-7.22 (m, 2H), 5.22-5.11 (m, 2H), 4.47-4.37 (m, 1H), 4.15-4.06 (m, 1H), 2.60-2.52 (m, 1H), 2.27-2.16 (m, 1H), 2.08-1.98 (m, 1H), 1.89-1.76 (m, 2H), 1.74-1.60 (m, 3H), 1.59-1.42 (m, 2H), 1.34 (dt, J=12.5, 6.3 Hz, 1H), 1.30-1.20 (m, 8H), 0.95-0.76 (m, 15H).

The synthesis method of compound A56 is the same as compound 39.

Example 57

Compound A57

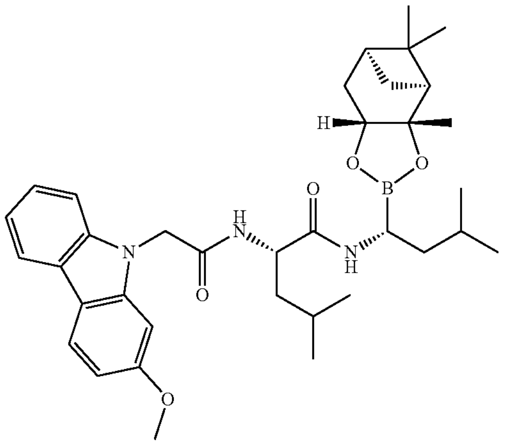

$^1$H NMR (400 MHz, DMSO) δ 8.88 (dd, J=18.4, 3.1 Hz, 1H), 8.60 (dd, J=27.6, 8.4 Hz, 1H), 8.00 (t, J=8.8 Hz, 2H), 7.43 (t, J=7.7 Hz, 1H), 7.34-7.26 (m, 1H), 7.15 (t, J=7.4 Hz, 1H), 7.09 (t, J=1.9 Hz, 1H), 6.80 (dd, J=8.5, 1.3 Hz, 1H), 5.13-4.95 (m, 2H), 4.50-4.41 (m, 1H), 4.15-4.09 (m, 1H), 3.85 (s, 3H), 2.59-2.53 (m, 1H), 2.27-2.17 (m, 1H), 2.08-1.98 (m, 1H), 1.89-1.78 (m, 2H), 1.71-1.59 (m, 3H), 1.55-1.43 (m, 2H), 1.38-1.31 (m, 1H), 1.28-1.18 (m, 8H), 0.89 (dd, J=6.3, 5.3 Hz, 3H), 0.84-0.80 (m, 12H).

The synthesis method of compound A57 is the same as that of compound 39.

Example 58

Compound A58

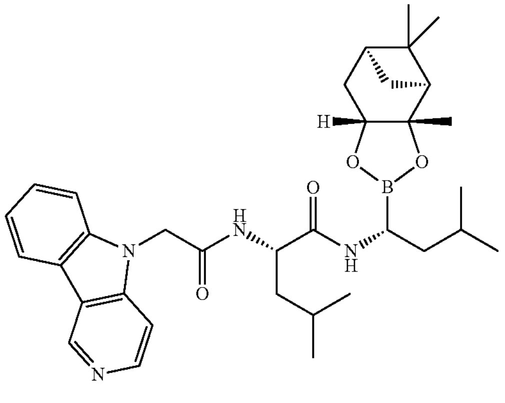

$^1$H NMR (400 MHz, DMSO) δ 9.35 (s, 1H), 8.98 (d, J=2.9 Hz, 1H), 8.71 (d, J=8.2 Hz, 1H), 8.45 (d, J=5.8 Hz, 1H), 8.26 (d, J=7.7 Hz, 1H), 7.58-7.53 (m, 2H), 7.52-7.46 (m, 1H), 7.31 (t, J=7.4 Hz, 1H), 5.13 (dd, J=35.0, 16.9 Hz, 2H), 4.47-4.38 (m, 1H), 4.14-4.05 (m, 1H), 2.59-2.53 (m, 1H), 2.26-2.17 (m, 1H), 2.08-1.98 (m, 1H), 1.89-1.77 (m, 2H), 1.71-1.60 (m, 3H), 1.58-1.41 (m, 2H), 1.34 (d, J=10.1 Hz, 1H), 1.31-1.19 (m, 8H), 0.92-0.81 (m, 15H).

The synthesis method of compound A58 is the same as that of compound 39.

Example 59

Compound A59

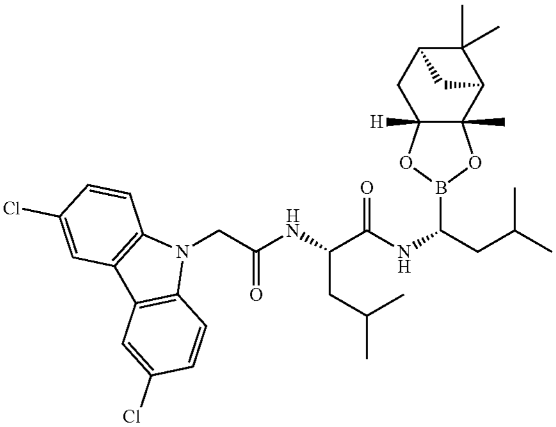

$^1$H NMR (400 MHz, DMSO) δ 8.96 (s, 1H), 8.65 (d, J=7.9 Hz, 1H), 8.33 (d, J=1.7 Hz, 2H), 7.59-7.56 (m, 2H), 7.48-7.44 (m, 2H), 5.11 (dd, J=36.1, 16.9 Hz, 2H), 4.45-4.34 (m, 1H), 4.09 (d, J=8.5 Hz, 1H), 2.58-2.52 (m, 1H), 2.26-2.16 (m, 1H), 2.07-1.97 (m, 1H), 1.88-1.76 (m, 2H), 1.70-1.57 (m, 3H), 1.57-1.40 (m, 2H), 1.33 (d, J=9.9 Hz, 1H), 1.28-1.15 (m, 8H), 0.93-0.73 (m, 15H).

The synthesis method of compound A59 is the same as that of compound 39.

Example 60

Compound A60

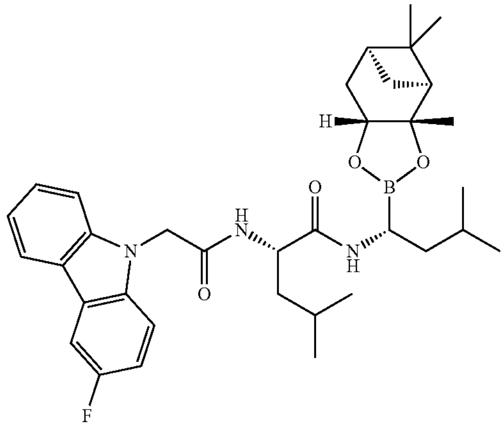

$^1$H NMR (400 MHz, DMSO) δ 9.00-8.90 (m, 1H), 8.71-8.62 (m, 1H), 8.16 (d, J=7.8 Hz, 1H), 8.00 (dd, J=9.2, 2.5 Hz, 1H), 7.56-7.48 (m, 2H), 7.46-7.41 (m, 1H), 7.30-7.23 (m, 1H), 7.20 (t, J=7.4 Hz, 1H), 5.20-4.98 (m, 2H), 4.47-4.40 (m, 1H), 4.16-4.09 (m, 1H), 2.57-2.52 (m, 1H), 2.28-2.17 (m, 1H), 2.08-2.00 (m, 1H), 1.90-1.78 (m, 2H), 1.72-1.60 (m, 3H), 1.57-1.41 (m, 2H), 1.35 (d, J=8.7 Hz, 1H), 1.31-1.16 (m, 8H), 0.95-0.76 (m, 15H).

The synthesis method of compound A60 is the same as that of compound 39.

Example 61

Compound A61

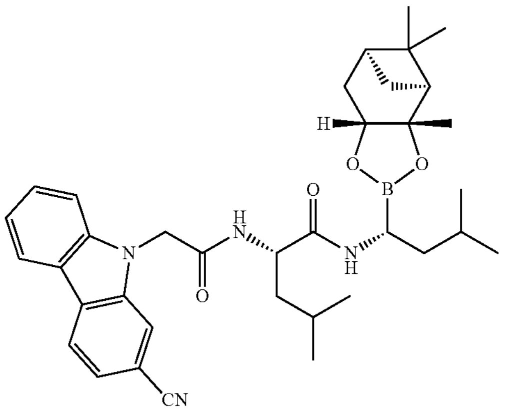

$^1$H NMR (400 MHz, DMSO) δ 8.99 (s, 1H), 8.68 (d, J=8.2 Hz, 1H), 8.37 (d, J=8.0 Hz, 1H), 8.28 (d, J=7.8 Hz, 1H), 8.16 (s, 1H), 7.60 (d, J=7.8 Hz, 2H), 7.54 (t, J=7.7 Hz, 1H), 7.30 (t, J=7.4 Hz, 1H), 5.26-5.12 (m, 2H), 4.44-4.37 (m, 1H), 4.09 (d, J=6.8 Hz, 1H), 2.58-2.54 (m, 1H), 2.26-2.17 (m, 1H), 2.06-1.95 (m, 1H), 1.87-1.77 (m, 2H), 1.73-1.52 (m, 4H), 1.49-1.40 (m, 1H), 1.31 (d, J=8.1 Hz, 1H), 1.29-1.17 (m, 8H), 0.94-0.78 (m, 15H).

The synthesis method of compound A61 is the same as that of compound 39.

Example 62

Compound A62

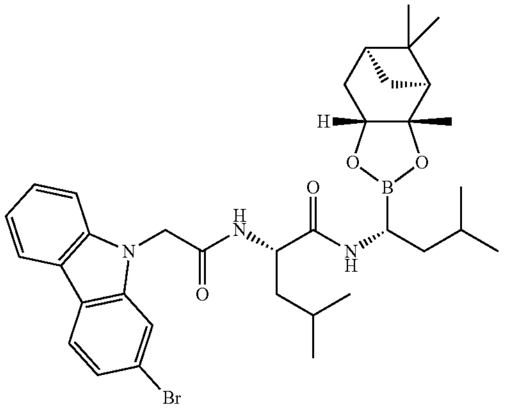

$^1$H NMR (400 MHz, DMSO) δ 8.98 (s, 1H), 8.65 (d, J=8.3 Hz, 1H), 8.16 (d, J=7.7 Hz, 1H), 8.10 (d, J=8.3 Hz, 1H), 7.82 (d, J=1.4 Hz, 1H), 7.52 (d, J=8.2 Hz, 1H), 7.44 (t, J=7.4 Hz, 1H), 7.34 (dd, J=8.3, 1.5 Hz, 1H), 7.23 (t, J=7.3 Hz, 1H), 5.10 (s, 2H), 4.43 (dd, J=14.1, 9.3 Hz, 1H), 4.10 (d, J=7.0 Hz, 1H), 2.60-2.53 (m, 1H), 2.27-2.16 (m, 1H), 2.07-2.00 (m, 1H), 1.89-1.77 (m, 2H), 1.75-1.52 (m, 4H), 1.50-1.41 (m, 1H), 1.33 (d, J=10.2 Hz, 1H), 1.28-1.22 (m, 8H), 0.92-0.80 (m, 15H).

The synthesis method of compound A62 is the same as that of compound 39.

Example 63

Compound A63

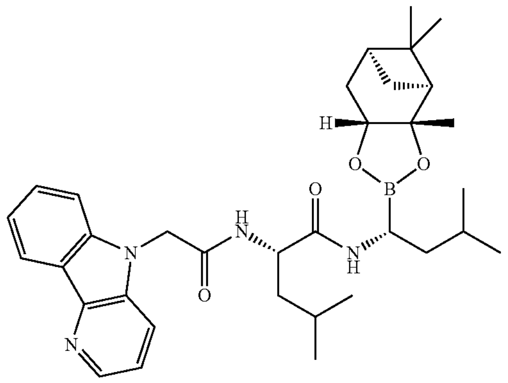

$^1$H NMR (400 MHz, DMSO) δ 9.00-8.85 (m, 1H), 8.73 (dd, J=19.6, 8.3 Hz, 1H), 8.56 (d, J=4.5 Hz, 1H), 8.27 (d, J=7.8 Hz, 1H), 8.13 (d, J=7.3 Hz, 1H), 7.60 (ddd, J=18.2, 14.1, 7.3 Hz, 3H), 7.34 (t, J=7.3 Hz, 1H), 5.31-5.12 (m, 2H), 4.46-4.38 (m, 1H), 4.16-4.08 (m, 1H), 2.53 (d, J=8.4 Hz, 1H), 2.28-2.13 (m, 1H), 2.09-2.00 (m, 1H), 1.89-1.77 (m, 2H), 1.71-1.58 (m, 3H), 1.56-1.42 (m, 2H), 1.38-1.19 (m, 10H), 0.94-0.75 (m, 14H).

The synthesis method of compound A63 is the same as that of compound 39.

Example 64

Compound A64

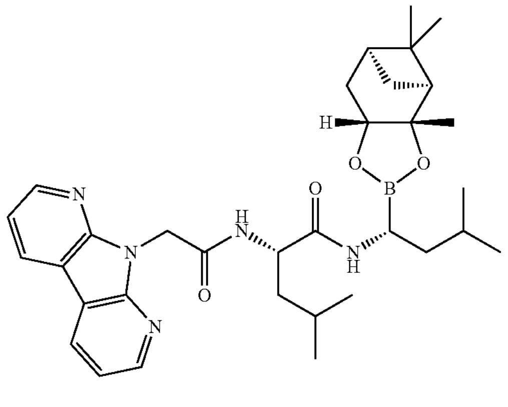

$^1$H NMR (400 MHz, DMSO) δ 8.61 (dd, J=7.7, 1.2 Hz, 2H), 8.49 (dd, J=4.8, 1.2 Hz, 2H), 8.44 (d, J=8.2 Hz, 1H), 7.85 (t, J=5.5 Hz, 1H), 7.34 (dd, J=7.6, 4.9 Hz, 2H), 5.15 (q, J=16.5 Hz, 2H), 4.23 (t, J=7.5 Hz, 1H), 3.06 (qd, J=13.1, 6.0 Hz, 2H), 2.23 (ddd, J=17.1, 16.7, 7.4 Hz, 1H), 2.03-1.74 (m, 2H), 1.72-1.40 (m, 5H), 1.32-1.18 (m, 9H), 0.85 (ddd, J=15.9, 11.4, 5.2 Hz, 16H).

The synthesis method of compound A64 is the same as that of compound 39.

Example 65

Compound A65

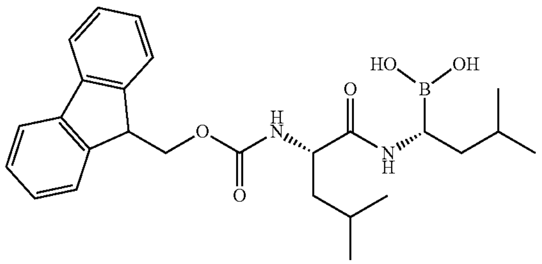

Compound A65 was synthesized as follows:

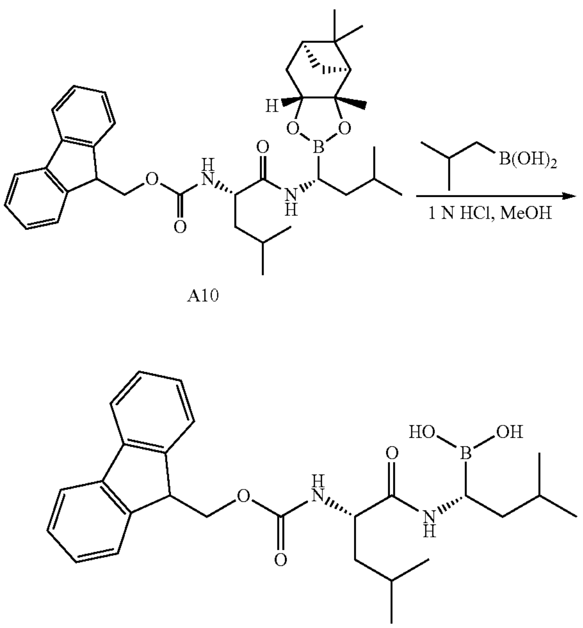

A10

A65

The raw material A10 (150 mg, 0.25 mmol) and the compound isobutylboronic acid (102 mg, 1 mmol) were dissolved in methanol, and diluted hydrochloric acid (1N, 1.5 mL) was added. The reaction was carried out at 70° C. for 6 h. Through spot plate monitoring, the raw material was reacted completely. The solvent was spin-dried. The produce was purified by medium pressure preparative liquid chromatography directly to obtain a white solid (42 mg, 36% yield).

$^1$H NMR (400 MHz, $CD_3OD$) δ 7.85 (d, J=7.6 Hz, 1H), 7.66 (t, J=6.8 Hz, 1H), 7.41 (t, J=7.4 Hz, 1H), 7.31 (td, J=7.4, 2.3 Hz, 1H), 4.33-4.14 (m, 4H), 3.95 (dd, J=9.0, 6.0 Hz, 1H), 3.00 (dd, J=9.1, 5.8 Hz, 1H), 1.57-1.44 (m, 2H), 1.44-1.34 (m, 2H), 1.34-1.16 (m, 3H), 0.85 (d, J=6.5 Hz, 3H), 0.82-0.72 (m, 9H).

ESI-MS $(M+H)^+$: 467.

The synthesis method of compound A66-A83 is the same as that of A65, except that A10 was replaced with the corresponding borate.

Example 66

Compound A66

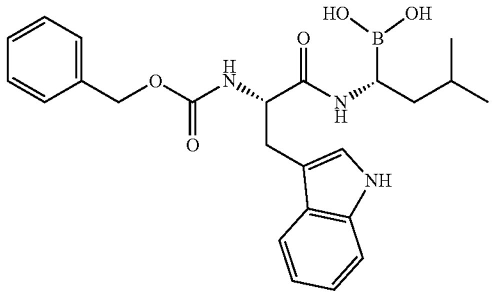

$^1$H NMR (400 MHz, MeOD) δ 7.57 (d, J=7.8 Hz, 1H), 7.37-7.24 (m, 6H), 7.14-7.07 (m, 2H), 7.03 (t, J=7.3 Hz, 1H), 5.05 (q, J=12.4 Hz, 2H), 4.64 (t, J=7.6 Hz, 1H), 3.25 (dt, J=16.2, 8.0 Hz, 2H), 2.55 (dd, J=9.5, 5.6 Hz, 1H), 1.25-1.16 (m, 1H), 1.12-0.99 (m, 2H), 0.77 (t, J 5=6.0 Hz, 6H).

ESI-MS $(M+H)^+$: 452.

Example 67

Compound A67

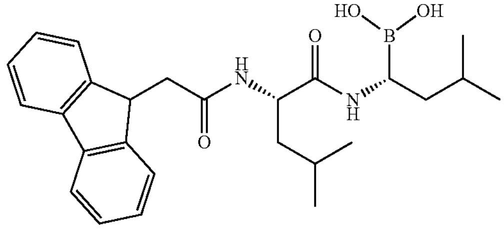

$^1$H NMR (400 MHz, MeOD) δ 7.78 (d, J=7.5 Hz, 2H), 7.55 (t, J=9.9 Hz, 1H), 7.48 (d, J=7.5 Hz, 1H), 7.36 (t, J=7.4 Hz, 2H), 7.33-7.23 (m, 2H), 4.72 (dd, J=9.7, 5.2 Hz, 1H), 4.38 (t, J=7.4 Hz, 1H), 2.77 (dd, J=14.6, 7.0 Hz, 2H), 2.58 (dd, J=14.7, 8.0 Hz, 1H), 1.73-1.53 (m, 4H), 1.37 (dd, J=12.9, 5.5 Hz, 2H), 0.97 (dd, J=15.0, 6.6 Hz, 12H).

ESI-MS $(M+H)^+$: 451.

Example 68

Compound A68

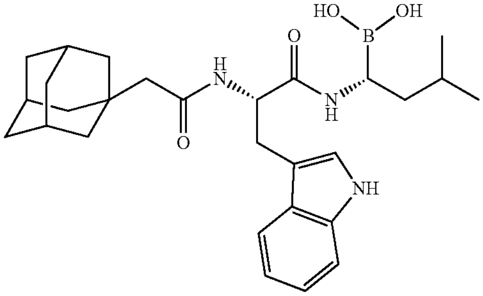

$^1$H NMR (400 MHz, $CD_3OD$) δ 7.61 (d, J=7.6 Hz, 1H), 7.32 (dd, J=7.9, 3.5 Hz, 1H), 7.14 (s, 1H), 7.11-7.00 (m, 2H), 4.93 (d, J=8.0 Hz, 1H), 3.17 (dd, J=18.1, 12.0 Hz, 1H), 2.67-2.57 (m, 1H), 1.95-1.86 (m, 2H), 1.81 (d, J=19.8 Hz, 3H), 1.64 (t, J=14.0 Hz, 3H), 1.56-1.37 (m, 7H), 1.31 (d, J=12.0 Hz, 5H), 1.13 (d, J=5.6 Hz, 1H), 0.89 (d, J=6.8 Hz, 3H), 0.85-0.78 (m, 3H).

ESI-MS $(M+H)^+$: 494.

Example 69

Compound A69

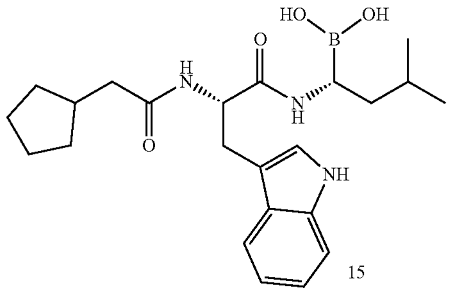

$^1$H NMR (400 MHz, MeOD) δ 7.60 (d, J=7.7 Hz, 1H), 7.33 (d, J=8.0 Hz, 1H), 7.18-7.00 (m, 3H), 4.87 (d, J=8.4 Hz, 1H), 3.28-3.16 (m, 2H), 2.65-2.54 (m, 1H), 2.22-2.16 (m, 2H), 1.75-1.44 (m, 6H), 1.32-0.95 (m, 6H), 0.90-0.76 (m, 6H).

ESI-MS $(M+Na)^+$: 450.0.

Example 70

Compound A70

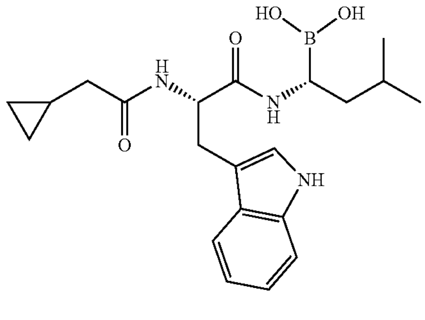

$^1$H NMR (400 MHz, DMSO) δ 10.83 (d, J=26.1 Hz, 1H), 8.67 (s, 1H), 7.92 (dd, J=37.5, 8.2 Hz, 1H), 7.53 (s, 1H), 7.32 (d, J=8.1 Hz, 1H), 7.15 (dd, J=21.9, 1.9 Hz, 1H), 7.05 (t, J=7.4 Hz, 1H), 6.96 (dd, J=15.9, 7.9 Hz, 1H), 4.67 (dd, J=13.5, 8.3 Hz, 1H), 4.55-4.45 (m, 1H), 3.25-3.07 (m, 1H), 3.01 (dd, J=14.7, 8.7 Hz, 1H), 2.90 (t, J=11.8 Hz, 1H), 2.64 (s, 1H), 2.06-1.90 (m, 2H), 1.59 (ddd, J=25.0, 13.3, 6.3 Hz, 1H), 1.44-1.16 (m, 3H), 0.84 (d, J=6.2 Hz, 6H).

ESI-MS $(M+H)^+$: 400.

Example 71

Compound A71

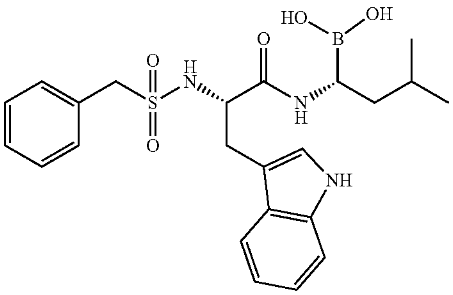

$^1$H NMR (400 MHz, MeOD) δ 7.50 (d, J=7.8 Hz, 1H), 7.37-7.27 (m, 4H), 7.22 (dd, J=7.7, 1.6 Hz, 2H), 7.14-7.03 (m, 3H), 4.24 (dd, J=8.4, 7.1 Hz, 1H), 4.11 (d, J=13.8 Hz, 1H), 4.01 (d, J=13.8 Hz, 1H), 3.21 (dd, J=14.1, 8.5 Hz, 1H), 3.11 (dd, J=14.1, 6.9 Hz, 1H), 2.58 (dd, J=9.8, 5.4 Hz, 1H), 1.18 (dq, J=12.7, 6.4 Hz, 1H), 1.12-0.96 (m, 2H), 0.81-0.72 (m, 6H).

ESI-MS $(M+H)^+$: 472.

Example 72

Compound A72

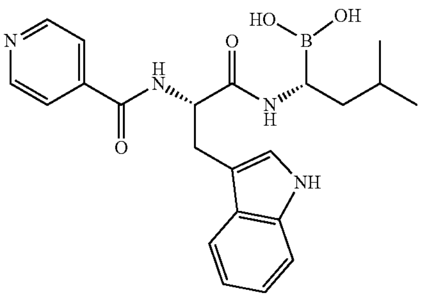

$^1$H NMR (400 MHz, MeOD) δ 8.68 (dd, J=4.5, 1.6 Hz, 2H), 7.73 (dd, J=4.5, 1.6 Hz, 2H), 7.64 (d, J=7.8 Hz, 1H), 7.34 (d, J=8.0 Hz, 1H), 7.17 (s, 1H), 7.08 (ddd, J=14.9, 13.9, 7.0 Hz, 2H), 5.05 (dd, J=8.5, 7.3 Hz, 1H), 3.45-3.33 (m, 2H), 2.61 (dd, J=9.6, 5.6 Hz, 1H), 1.35-1.19 (m, 2H), 1.10-1.04 (m, 1H), 0.79 (t, J=6.4 Hz, 6H).

ESI-MS $(M+H)^+$: 423.

Example 73

Compound A73

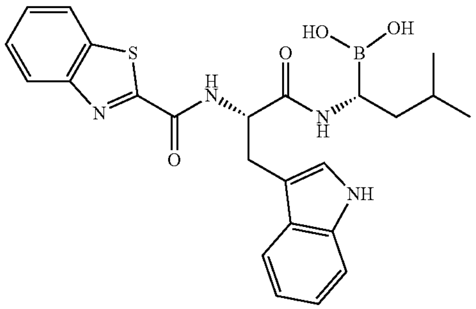

$^1$H NMR (400 MHz, MeOD) δ 8.09 (dt, J=12.6, 6.5 Hz, 2H), 7.72-7.49 (m, 3H), 7.34 (d, J=8.0 Hz, 1H), 7.21 (d, J=4.3 Hz, 1H), 7.07 (dt, J=25.7, 7.2 Hz, 2H), 5.10 (dd, J=15.9, 8.6 Hz, 1H), 3.54-3.37 (m, 2H), 2.64 (dd, J=9.2, 6.2 Hz, 1H), 1.31 (dd, J=14.1, 6.7 Hz, 2H), 1.18-1.09 (m, 1H), 0.83 (ddd, J=20.3, 6.4, 4.2 Hz, 6H).

ESI-MS $(M+H)^+$: 479.

Example 74

Compound A74

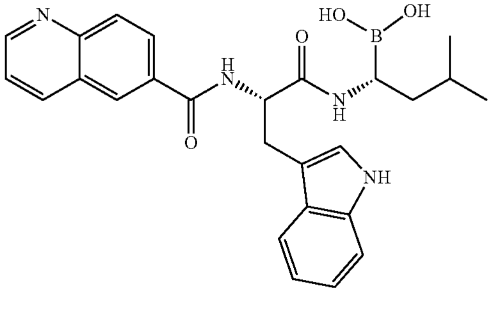

$^1$H NMR (400 MHz, MeOD) δ 8.95 (dd, J=4.3, 1.6 Hz, 1H), 8.45 (d, J=8.4 Hz, 1H), 8.39 (d, J=1.7 Hz, 1H), 8.12 (dt, J=19.3, 5.4 Hz, 2H), 7.68 (d, J=7.7 Hz, 1H), 7.63 (dd, J=8.3, 4.3 Hz, 1H), 7.36 (d, J=8.0 Hz, 1H), 7.20 (s, 1H), 7.09 (dt, J=23.0, 7.0 Hz, 2H), 5.12 (t, J=7.8 Hz, 1H), 3.55-3.39 (m, 2H), 2.63 (dd, J=9.6, 5.7 Hz, 1H), 1.27 (d, J=19.9 Hz, 3H), 1.13-1.05 (m, 2H), 0.80 (t, J=6.6 Hz, 6H).

ESI-MS $(M+H)^+$: 473.

Example 75

Compound A75

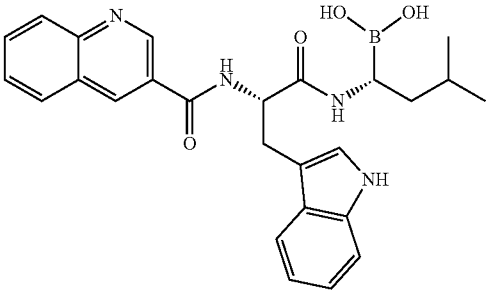

$^1$H NMR (400 MHz, MeOD) δ 9.14 (d, J=20.0 Hz, 1H), 8.66 (d, J=34.7 Hz, 1H), 8.12-7.93 (m, 2H), 7.87 (d, J=5.5 Hz, 1H), 7.68 (t, J=7.3 Hz, 2H), 7.35 (d, J=8.1 Hz, 1H), 7.22 (d, J=5.1 Hz, 1H), 7.08 (dt, J=13.7, 6.7 Hz, 2H), 5.18 (dt, J=15.3, 7.4 Hz, 1H), 3.54-3.35 (m, 2H), 2.73-2.58 (m, 1H), 1.39-1.21 (m, 2H), 1.16-1.06 (m, 1H), 0.92-0.74 (m, 6H).

ESI-MS $(M+H)^+$: 473.

Example 76

Compound A76

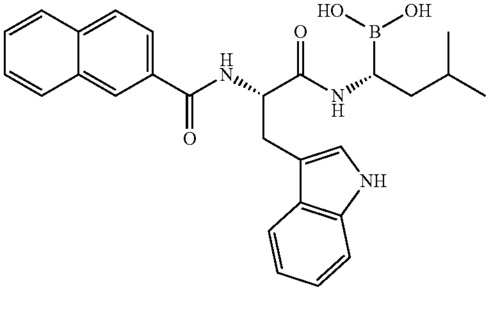

$^1$H NMR (400 MHz, MeOD) δ 8.29 (d, J=28.9 Hz, 1H), 7.98-7.88 (m, 3H), 7.82 (ddd, J=16.7, 8.6, 1.8 Hz, 1H), 7.69 (t, J=7.1 Hz, 1H), 7.63-7.51 (m, 2H), 7.36 (d, J=7.8 Hz, 1H), 7.21 (d, J=4.6 Hz, 1H), 7.16-7.03 (m, 2H), 5.24-5.07 (m, 1H), 3.57-3.38 (m, 2H), 2.72-2.56 (m, 1H), 1.37-1.26 (m, 2H), 1.14-1.06 (m, 1H), 0.91-0.75 (m, 6H).

ESI-MS $(M+H)^+$: 472.

Example 77

Compound A77

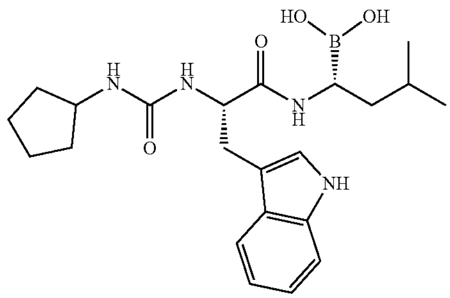

$^1$H NMR (400 MHz, MeOD) δ 7.60 (d, J=7.7 Hz, 1H), 7.33 (d, J=8.0 Hz, 1H), 7.14-7.00 (m, 3H), 4.74 (t, J=7.4 Hz, 1H), 3.92 (p, J=6.4 Hz, 1H), 3.19 (d, J=7.4 Hz, 2H), 2.57 (dd, J=9.5, 5.8 Hz, 1H), 1.87 (dt, J=12.8, 6.5 Hz, 2H), 1.73-1.53 (m, 4H), 1.35-1.20 (m, 3H), 1.17-1.01 (m, 2H), 0.79 (dd, J=6.5, 4.1 Hz, 6H).

ESI-MS $(M+Na)^+$: 450.9.

Example 78

Compound A78

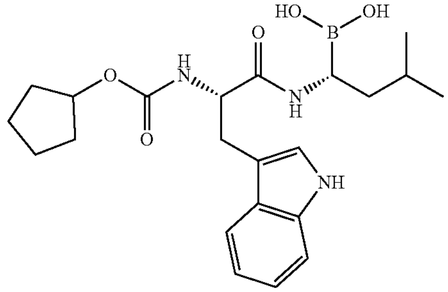

$^1$H NMR (400 MHz, MeOD) δ 7.59 (d, J=7.8 Hz, 1H), 7.34 (d, J=8.0 Hz, 1H), 7.17-7.00 (m, 3H), 4.96 (d, J=19.7 Hz, 1H), 4.61 (t, J=7.6 Hz, 1H), 3.28-3.12 (m, 2H), 2.57 (dd, J=9.5, 5.4 Hz, 1H), 1.89-1.45 (m, 8H), 1.31-0.99 (m, 3H), 0.79 (t, J=6.3 Hz, 6H).

ESI-MS $(M+Na)^+$: 452.2.

Example 79

Compound A79

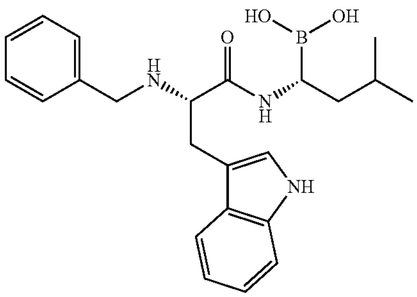

$^1$H NMR (400 MHz, MeOD) δ 7.52 (d, J=7.8 Hz, 1H), 7.34 (d, J=8.1 Hz, 1H), 7.30-7.18 (m, 5H), 7.13-7.06 (m, 2H), 7.04-6.97 (m, 1H), 3.74 (dd, J=14.8, 10.2 Hz, 2H), 3.62 (d, J=13.1 Hz, 1H), 3.24-3.15 (m, 2H), 2.56 (dd, J=9.8, 5.5 Hz, 1H), 1.24 (dd, J=12.6, 6.4 Hz, 1H), 1.18-1.00 (m, 2H), 0.80 (dd, J=6.5, 4.8 Hz, 6H).

ESI-MS $(M-H_2O)^+$:390.1.

Example 80

Compound A80

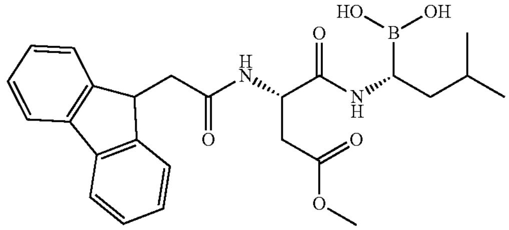

$^1$H NMR (400 MHz, MeOD) δ 7.78 (d, J=7.5 Hz, 2H), 7.53 (dd, J=17.4, 7.4 Hz, 2H), 7.37 (t, J=7.4 Hz, 2H), 7.30 (td, J=7.4, 2.7 Hz, 2H), 5.11 (t, J=6.7 Hz, 1H), 4.39 (t, J=7.4 Hz, 1H), 3.70 (s, 3H), 2.88 (d, J=6.7 Hz, 2H), 2.83-2.70 (m, 2H), 2.60 (dd, J=14.8, 7.9 Hz, 1H), 1.69 (dt, J=13.6, 6.7 Hz, 1H), 1.38 (t, J=7.3 Hz, 2H), 0.93 (t, J=9.8 Hz, 6H).

ESI-MS $(M+Na)^+$: 489.

Example 81

Compound A81

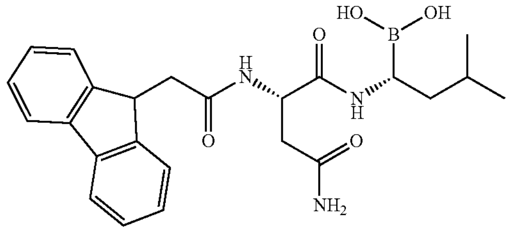

$^1$H NMR (400 MHz, MeOD) δ 7.78 (d, J=7.4 Hz, 2H), 7.54 (dd, J=17.9, 7.5 Hz, 2H), 7.36 (t, J=7.5 Hz, 2H), 7.31 (dt, J=11.7, 3.7 Hz, 2H), 5.11 (t, J=6.6 Hz, 1H), 4.59 (s, 4H), 4.39 (t, J=7.4 Hz, 1H), 2.83-2.68 (m, 4H), 2.67-2.57 (m, 1H), 1.68 (dd, J=13.5, 7.0 Hz, 1H), 1.39 (dd, J=15.2, 7.5 Hz, 2H), 0.93 (t, J=9.4 Hz, 6H).

ESI-MS $(M+Na)^+$: 474.

Example 82

Compound A82

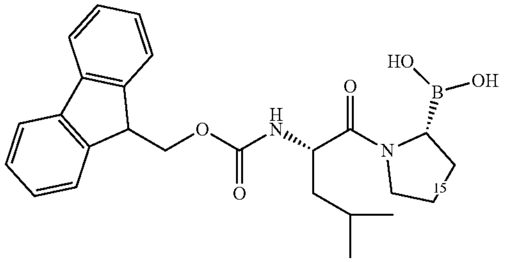

$^1$H NMR (400 MHz, MeOD) δ 7.80 (d, J=7.5 Hz, 2H), 7.70-7.58 (m, 2H), 7.39 (t, J=7.4 Hz, 2H), 7.32 (q, J=7.4 Hz, 2H), 4.46-4.37 (m, 2H), 4.21 (t, J=6.6 Hz, 1H), 3.72 (t, J=9.6 Hz, 1H), 3.41 (dd, J=17.1, 9.9 Hz, 1H), 3.07 (dd, J=11.2, 6.4 Hz, 1H), 2.85 (d, J=7.2 Hz, 1H), 2.14 (d, J=9.9 Hz, 1H), 2.03-1.88 (m, 2H), 1.76-1.42 (m, 4H), 0.94 (dt, J=18.1, 9.1 Hz, 5H).

ESI-MS $(M+H)^+$: 451.

Example 83

Compound A83

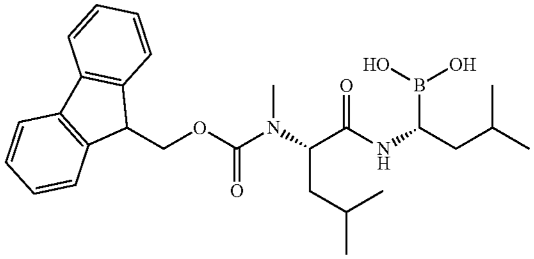

$^1$H NMR (400 MHz, MeOD) δ 7.80 (d, J=7.5 Hz, 2H), 7.61 (t, J=6.6 Hz, 2H), 7.40 (t, J=7.4 Hz, 2H), 7.31 (t, J=7.4 Hz, 2H), 5.02-4.90 (m, 1H), 4.57 (d, J=6.5 Hz, 2H), 4.48 (d, J=5.8 Hz, 1H), 4.26 (t, J=5.8 Hz, 1H), 2.78 (d, J=29.8 Hz, 3H), 2.65 (t, J=7.5 Hz, 1H), 1.78 (s, 1H), 1.62 (ddd, J=20.6, 13.7, 7.7 Hz, 2H), 1.40-1.26 (m, 3H), 0.93 (dd, J=17.9, 6.5 Hz, 12H).

ESI-MS $(M+H)^+$: 481.

Example 84

Compound A84

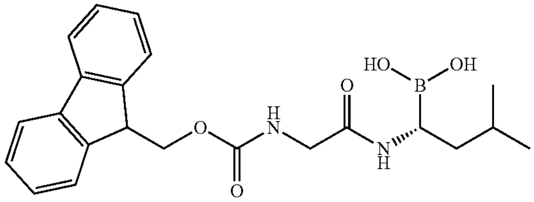

$^1$H NMR (400 MHz, $CD_3OD$) δ 7.80 (d, J=7.5 Hz, 2H), 7.64 (t, J=13.9 Hz, 2H), 7.39 (t, J=7.4 Hz, 2H), 7.31 (t, J=7.4 Hz, 2H), 4.47-4.32 (m, 2H), 4.23 (t, J=6.8 Hz, 1H), 4.01 (s, 2H), 2.70 (t, J=7.6 Hz, 1H), 1.71-1.61 (m, 1H), 1.34 (t, J=7.3 Hz, 2H), 0.91 (d, J=6.6 Hz, 6H).

The synthesis method of compound A84 is the same as that of compound A51.

Example 85

Compound A85

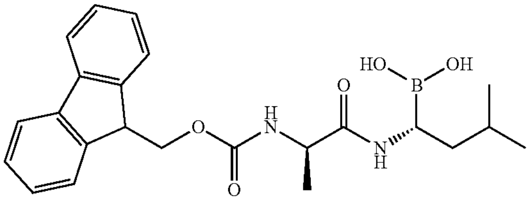

$^1$H NMR (400 MHz, CD3OD) δ 7.80 (d, J=7.5 Hz, 2H), 7.71-7.60 (m, 2H), 7.39 (t, J=7.4 Hz, 2H), 7.32 (t, J=7.4 Hz, 2H), 4.47-4.31 (m, 3H), 4.22 (t, J=6.6 Hz, 1H), 2.68 (t, J=7.5 Hz, 1H), 1.72-1.62 (m, 1H), 1.39 (t, J=9.8 Hz, 3H), 1.34 (t, J=7.3 Hz, 2H), 0.91 (d, J=6.6 Hz, 6H).

The synthesis method of compound A85 is the same as that of compound A51.

Example 86

Compound A86

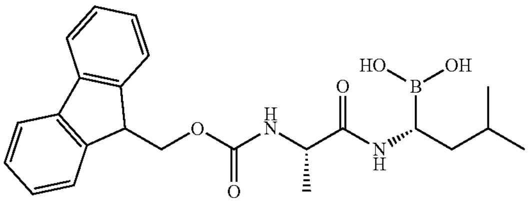

$^1$H NMR (400 MHz, CD3OD) δ 7.80 (d, J=7.5 Hz, 2H), 7.67 (t, J=6.8 Hz, 2H), 7.39 (t, J=7.4 Hz, 2H), 7.32 (t, J=7.4 Hz, 2H), 4.44-4.33 (m, 3H), 4.22 (t, J=6.7 Hz, 1H), 2.69 (t, J=7.6 Hz, 1H), 1.70-1.58 (m, 1H), 1.41 (d, J=7.2 Hz, 3H), 1.32 (t, J=7.3 Hz, 2H), 0.91 (d, J=6.6 Hz, 6H).

The synthesis method of compound A86 is the same as that of compound A51.

Example 87

Compound A87

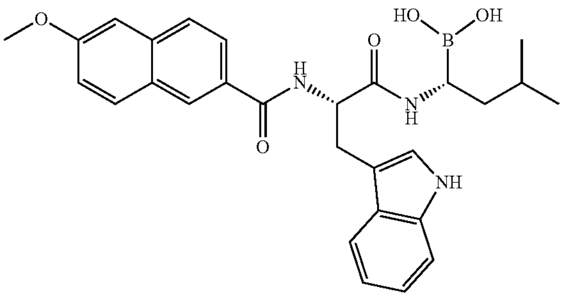

$^1$H NMR (400 MHz, CD3OD) δ 8.26-8.14 (m, 1H), 7.87-7.74 (m, 3H), 7.69 (dd, J=7.2, 6.3 Hz, 1H), 7.36 (d, J=7.9 Hz, 1H), 7.28 (dd, J=5.2, 2.5 Hz, 1H), 7.23-7.16 (m, 2H), 7.16-7.00 (m, 2H), 5.21-5.07 (m, 1H), 3.93 (s, 3H), 3.55-3.34 (m, 2H), 2.67-2.61 (m, 1H), 1.38-1.31 (m, 1H), 1.30-1.02 (m, 2H), 0.89-0.78 (m, 6H).

The synthesis method of compound A87 is the same as that of compound A51.

Example 88

Compound A88

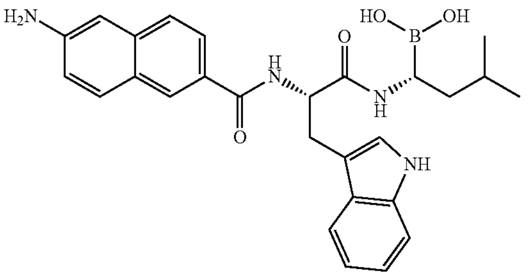

$^1$H NMR (400 MHz, CD3OD) δ 8.10 (d, J=25.3 Hz, 1H), 7.72-7.63 (m, 3H), 7.55 (t, J=8.3 Hz, 1H), 7.36 (d, J=7.8 Hz, 1H), 7.20 (d, J=3.5 Hz, 1H), 7.15-7.02 (m, 3H), 6.97 (dd, J=4.5, 2.2 Hz, 1H), 5.17-5.07 (m, 1H), 3.50-3.36 (m, 2H), 2.68-2.59 (m, 1H), 1.65-1.54 (m, 1H), 1.39-1.31 (m, 2H), 0.91-0.78 (m, 6H).

The synthesis method of compound A88 is the same as that of compound A51.

Example 89

Compound A89

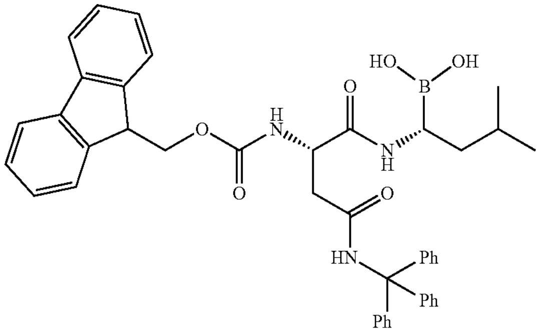

$^1$H NMR (400 MHz, CD3OD) δ 7.79 (d, J=7.4 Hz, 2H), 7.65 (dd, J=7.1, 3.2 Hz, 2H), 7.39 (t, J=7.4 Hz, 2H), 7.33-7.15 (m, 17H), 4.68 (dd, J=7.6, 5.4 Hz, 1H), 4.47-4.37 (m, 2H), 4.21 (t, J=6.5 Hz, 1H), 2.94-2.67 (m, 3H), 1.69-1.56 (m, 1H), 1.38-1.27 (m, 2H), 0.93-0.81 (m, 6H).

The synthesis method of compound A89 is the same as that of compound A51.

Example 90

Compound A90

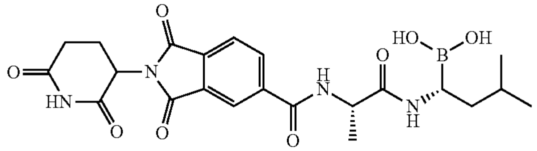

$^1$H NMR (400 MHz, CD3OD) δ 8.37 (d, J=0.7 Hz, 1H), 8.32 (dd, J=7.8, 1.5 Hz, 1H), 8.00 (dd, J=7.8, 0.6 Hz, 1H), 5.18 (dd, J=12.5, 5.5 Hz, 1H), 4.81-4.76 (m, 1H), 2.94-2.69 (m, 4H), 2.22-2.11 (m, 1H), 1.73-1.60 (m, 1H), 1.56 (d, J=8.6 Hz, 3H), 1.36 (t, J=7.3 Hz, 2H), 0.93 (d, J=6.6 Hz, 6H).

The synthesis method of compound A90 is the same as that of compound A51.

Example 91

Compound A91

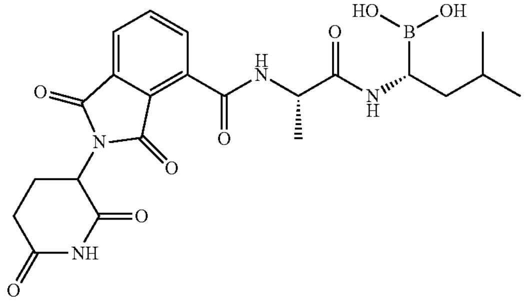

$^1H$ NMR (400 MHz, CD3OD) δ 8.17-8.07 (m, 2H), 7.99 (t, J=7.6 Hz, 1H), 5.25 (dd, J=12.6, 5.5 Hz, 1H), 4.59 (s, 1H), 3.00-2.86 (m, 1H), 2.85-2.70 (m, 3H), 2.26-2.17 (m, 1H), 1.77-1.62 (m, 1H), 1.56 (d, J=10.9 Hz, 3H), 1.46-1.32 (m, 2H), 0.98-0.89 (m, 6H).

The synthesis method of compound A91 is the same as that of compound A51.

Example 92

Compound A92

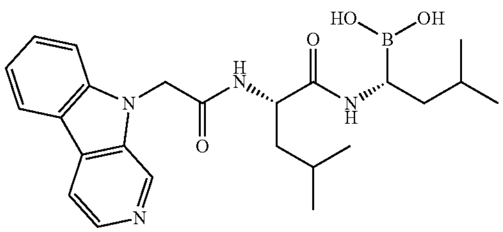

$^1H$ NMR (400 MHz, CD3OD) δ 8.86 (s, 1H), 8.36 (d, J=5.3 Hz, 1H), 8.24 (d, J=7.9 Hz, 1H), 8.15 (d, J=5.3 Hz, 1H), 7.67-7.60 (m, 1H), 7.56 (d, J=8.3 Hz, 1H), 7.34 (t, J=7.4 Hz, 1H), 5.31-5.11 (m, 2H), 4.64-4.57 (m, 1H), 2.66 (t, J=7.6 Hz, 1H), 1.82-1.66 (m, 2H), 1.65-1.55 (m, 2H), 1.28 (t, J=7.3 Hz, 2H), 0.98 (d, J=6.3 Hz, 3H), 0.92 (d, J=6.3 Hz, 3H), 0.88 (d, J=6.6 Hz, 6H).

The synthesis method of compound A92 is the same as that of compound A51.

Example 93

Compound A93

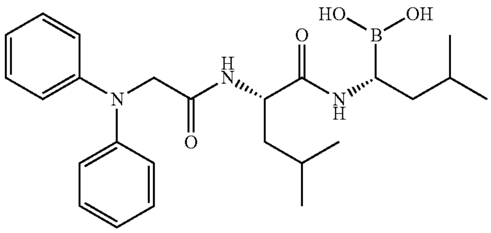

$^1H$ NMR (400 MHz, CD3OD) δ 7.26 (t, J=7.9 Hz, 4H), 7.08-7.01 (m, 4H), 6.98 (t, J=7.4 Hz, 2H), 4.72-4.63 (m, 1H), 4.48-4.34 (m, 2H), 2.74-2.62 (m, 1H), 1.72-1.59 (m, 2H), 1.58-1.37 (m, 2H), 1.40-1.29 (m, 2H), 0.92-0.82 (m, 12H).

The synthesis method of compound A93 is the same as that of compound A51.

Example 94

Compound A94

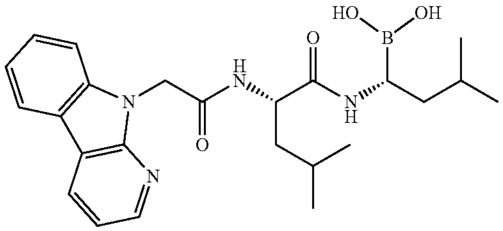

$^1H$ NMR (400 MHz, CD3OD) δ 8.49 (dd, J=7.7, 1.1 Hz, 1H), 8.41 (dt, J=4.9, 1.6 Hz, 1H), 8.15 (d, J=7.8 Hz, 1H), 7.56-7.45 (m, 2H), 7.34-7.24 (m, 2H), 5.28-5.14 (m, 2H), 4.72-4.61 (m, 1H), 2.67 (t, J=7.6 Hz, 1H), 1.78-1.57 (m, 4H), 1.36-1.27 (m, 2H), 1.00-0.85 (m, 12H).

The synthesis method of compound A94 is the same as that of compound A51.

Example 95

Compound A95

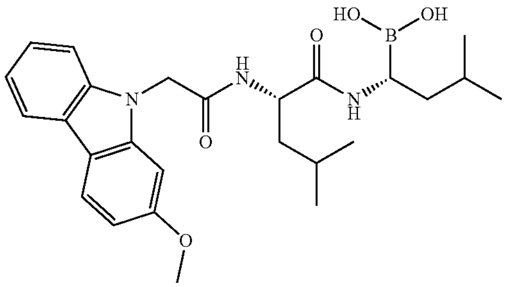

$^1H$ NMR (400 MHz, CD3OD) δ 7.95 (dd, J=12.0, 8.1 Hz, 2H), 7.40-7.29 (m, 2H), 7.18 (dd, J=10.7, 4.5 Hz, 1H), 6.95 (t, J=2.2 Hz, 1H), 6.84 (dd, J=8.5, 1.6 Hz, 1H), 5.09-4.96 (m, 2H), 4.73-4.63 (m, 1H), 3.90 (s, 3H), 2.70-2.61 (m, 1H), 1.75-1.54 (m, 4H), 1.32-1.27 (m, 2H), 0.96-0.86 (m, 12H).

The synthesis method of compound A95 is the same as that of compound A51.

Example 96

Compound A96

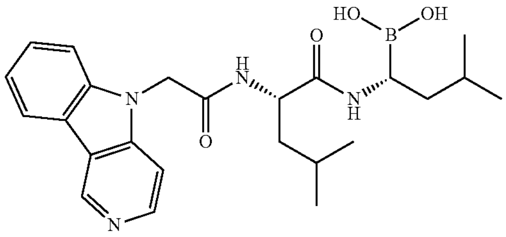

$^1H$ NMR (400 MHz, CD3OD) δ 9.29 (s, 1H), 8.54-8.37 (m, 1H), 8.26 (d, J=7.8 Hz, 1H), 7.64-7.53 (m, 3H), 7.44-

7.35 (m, 1H), 5.28-5.10 (m, 2H), 4.67-4.62 (m, 1H), 2.68 (t, J=7.6 Hz, 1H), 1.84-1.68 (m, 2H), 1.66-1.54 (m, 2H), 1.32-1.27 (m, 2H), 1.01-0.86 (m, 12H).

The synthesis method of compound A96 is the same as that of compound A51.

Example 97

Compound A97

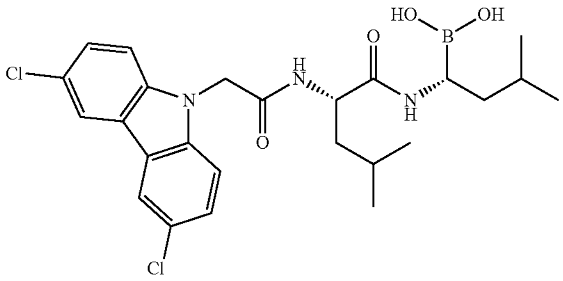

$^1$H NMR (400 MHz, CD3OD) δ 8.09 (s, 2H), 7.43 (s, 4H), 5.08 (q, J=16.9 Hz, 2H), 4.63-4.59 (m, 1H), 2.67 (t, J=7.5 Hz, 1H), 1.80-1.54 (m, 4H), 1.31-1.27 (m, 2H), 1.02-0.85 (m, 12H).

The synthesis method of compound A97 is the same as that of compound A51.

Example 98

Compound A98

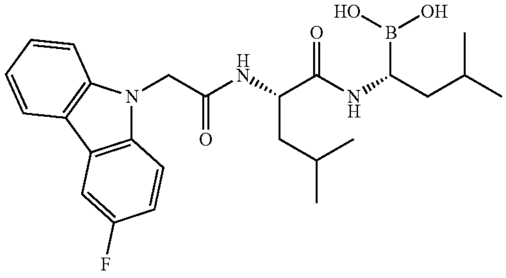

$^1$H NMR (400 MHz, CD3OD) δ 8.07 (d, J=7.8 Hz, 1H), 7.80 (d, J=8.9 Hz, 1H), 7.50-7.38 (m, 3H), 7.24-7.17 (m, 2H), 5.14-5.02 (m, 2H), 4.67-4.61 (m, 1H), 2.67 (t, J=7.3 Hz, 1H), 1.77-1.52 (m, 4H), 1.38-1.24 (m, 2H), 1.01-0.87 (m, 12H).

The synthesis method of compound A98 is the same as that of compound A51.

Example 99

Compound A99

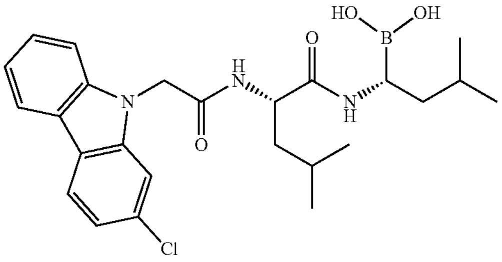

$^1$H NMR (400 MHz, CD3OD) δ 8.06 (dd, J=12.1, 8.1 Hz, 2H), 7.50-7.40 (m, 3H), 7.24 (dd, J=10.6, 5.1 Hz, 1H), 7.20 (d, J=8.3 Hz, 1H), 5.13-5.02 (m, 2H), 4.67-4.63 (m, 1H), 2.71-2.63 (m, 1H), 1.78-1.55 (m, 4H), 1.33-1.26 (m, 2H), 1.02-0.88 (m, 12H).

The synthesis method of compound A99 is the same as that of compound A51.

Example 100

Compound A100

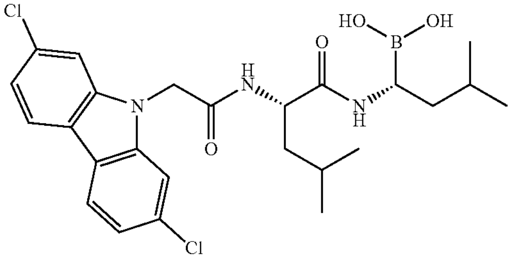

$^1$H NMR (400 MHz, CD3OD) δ 8.04 (d, J=8.3 Hz, 2H), 7.51 (d, J=1.6 Hz, 2H), 7.23 (dd, J=8.3, 1.7 Hz, 2H), 5.07 (s, 2H), 4.68-4.64 (m, 1H), 2.68 (t, J=7.6 Hz, 1H), 1.77-1.56 (m, 4H), 1.29-1.25 (m, 2H), 1.01-0.89 (m, 12H).

The synthesis method of compound A100 is the same as that of compound A51.

Example 101

Compound A101

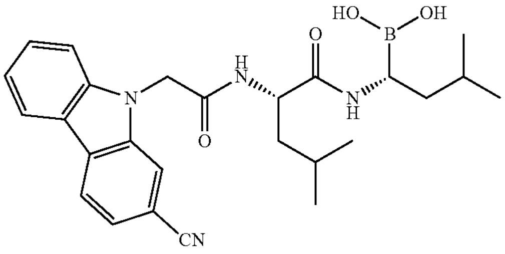

$^1$H NMR (400 MHz, CD3OD) δ 8.26 (d, J=8.0 Hz, 1H), 8.20 (d, J=7.9 Hz, 1H), 7.90 (s, 1H), 7.55-7.52 (m, 3H), 7.32

(t, J=7.3 Hz, 1H), 5.24-5.10 (m, 2H), 4.63 (dd, J=9.5, 5.5 Hz, 1H), 2.67 (t, J=7.6 Hz, 1H), 1.81-1.67 (m, 2H), 1.66-1.56 (m, 2H), 1.31-1.27 (m, 2H), 1.03-0.87 (m, 12H).

The synthesis method of compound A101 is the same as that of compound A51.

Example 102

Compound A102

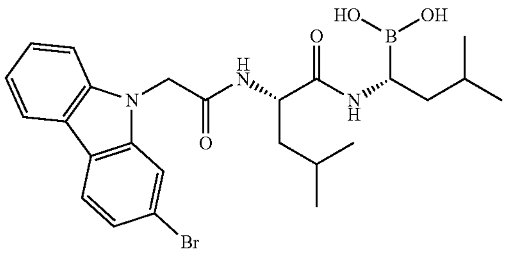

$^1$H NMR (400 MHz, CD3OD) δ 8.08 (d, J=7.8 Hz, 1H), 7.99 (d, J=8.3 Hz, 1H), 7.64 (d, J=1.4 Hz, 1H), 7.50-7.41 (m, 2H), 7.34 (dd, J=8.3, 1.5 Hz, 1H), 7.29-7.21 (m, 1H), 5.13-5.01 (m, 2H), 4.67-4.60 (m, 1H), 2.68 (t, J=7.6 Hz, 1H), 1.80-1.66 (m, 2H), 1.67-1.56 (m, 2H), 1.32-1.28 (m, 2H), 1.02-0.85 (m, 12H).

The synthesis method of compound A102 is the same as that of compound A51.

Example 103

Compound A103

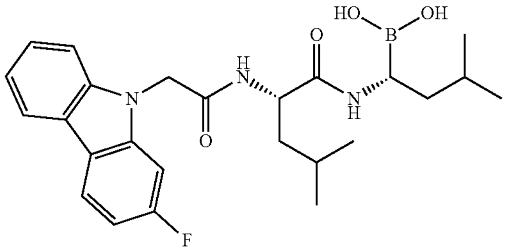

$^1$H NMR (400 MHz, CD3OD) δ 8.07-8.04 (m, 2H), 7.45-7.38 (m, 2H), 7.27-7.16 (m, 2H), 7.00-6.94 (m, 1H), 5.06 (q, J=17.2 Hz, 2H), 4.67-4.63 (m, 1H), 2.67 (t, J=7.6 Hz, 1H), 1.82-1.55 (m, 4H), 1.34-1.28 (m, 2H), 1.01-0.84 (m, 12H).

The synthesis method of compound A103 is the same as that of compound A51.

Example 104

Compound A104

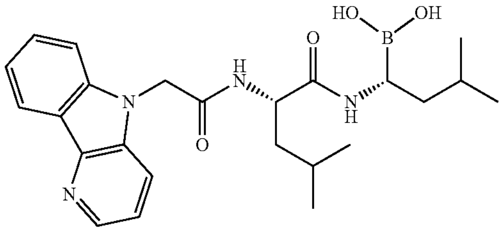

$^1$H NMR (400 MHz, CD3OD) δ 8.45 (d, J=4.7 Hz, 1H), 8.32 (d, J=7.8 Hz, 1H), 7.97-7.89 (m, 1H), 7.62-7.44 (m, 3H), 7.34 (t, J=7.4 Hz, 1H), 5.23-5.06 (m, 2H), 4.72-4.60 (m, 1H), 2.67 (t, J=7.6 Hz, 1H), 1.81-1.55 (m, 4H), 1.29 (t, J=7.3 Hz, 2H), 1.00-0.83 (m, 12H).

The synthesis method of compound A104 is the same as that of compound A51.

Example 105

Compound A105

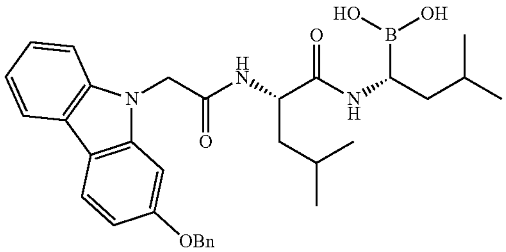

$^1$H NMR (400 MHz, CD3OD) δ 7.96 (t, J=8.1 Hz, 2H), 7.49 (d, J=7.3 Hz, 2H), 7.42-7.29 (m, 5H), 7.18 (t, J=7.2 Hz, 1H), 7.06 (d, J=2.1 Hz, 1H), 6.92 (dd, J=8.5, 2.1 Hz, 1H), 5.21-5.13 (m, 2H), 5.09-4.97 (m, 2H), 4.66-4.62 (m, 1H), 2.66 (t, J=7.6 Hz, 1H), 1.76-1.51 (m, 4H), 1.35-1.26 (m, 2H), 0.95-0.85 (m, 12H).

The synthesis method of compound A105 is the same as that of compound A51.

Example 106

Compound A106

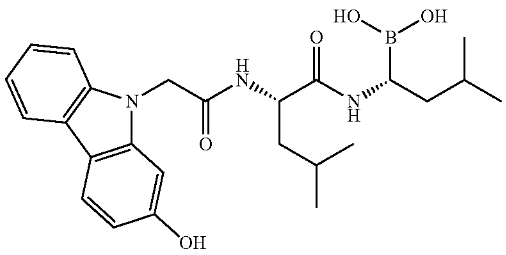

$^1$H NMR (400 MHz, CD3OD) δ 7.94 (d, J=7.7 Hz, 1H), 7.86 (d, J=8.4 Hz, 1H), 7.36-7.29 (m, 2H), 7.20-7.11 (m,

1H), 6.80-6.70 (m, 2H), 5.06-4.91 (m, 2H), 4.69-4.64 (m, 1H), 2.68 (t, J=7.6 Hz, 1H), 1.77-1.50 (m, 4H), 1.31-1.24 (m, 2H), 1.00-0.85 (m, 12H).

The synthesis method of compound A106 is the same as that of compound A51.

Example 107

Compound A107

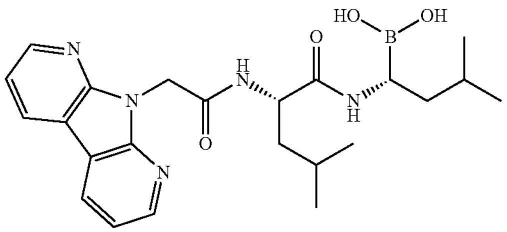

$^1$H NMR (400 MHz, CD3OD) δ 8.56 (dd, J=7.7, 1.4 Hz, 2H), 8.49 (dd, J=5.0, 1.4 Hz, 2H), 7.36 (dd, J=7.7, 5.0 Hz, 2H), 5.39-5.25 (m, 2H), 4.63 (dd, J=9.4, 5.4 Hz, 1H), 2.67 (t, J=7.2 Hz, 1H), 1.85-1.61 (m, 4H), 1.15 (t, J=7.2 Hz, 3H), 1.00-0.86 (m, 12H).

The synthesis method of compound A107 is the same as that of compound A51.

Effect Example 1: Anti-Cancer Activity Test of the Compound of the Present Disclosure Experimental Method:

1. Cell Culture Method.

Cell culture medium: Roswell medium RPMI-1640 (+L-glutamine) was added with 10% fetal bovine serum, with 100 units penicillin and 100 μg streptomycin per ml.

Cell culture conditions: 5% $CO_2$, 95% humidity, cultured at 37° C. constant temperature.

2. Cell Inoculation, Drugs Dosing and Culture.

Logarithmic growth phase HL-60, human chronic myeloid leukemia cells (K562), human esophageal squamous cell carcinoma cells (KYSE510), human large cell lung cancer cells (H460) were inoculated into 96-well cell culture plates, $2\times10^4$ cells per well. Different concentrations of active compounds (dissolved in dimethyl sulfoxide (DMSO) stock solution) were added, so that the final concentration of DMSO was 0.2%, and the control group was DMSO. Each group was repeated three times.

3. Mtt Experiment.

After culturing for 72 hours, 20 L of thiazolyl blue (MTT) (5 mg/ml, ready for use, dissolved in 1×PBS for cell culture) was added to each well, and incubated at 37° C. for 3 hours.

The 96-well cell culture plates were centrifuged at 1000 rpm for 10 minutes. The supernatant was discarded; 200 μL of DMSO was added to each well and the plate was shaken for 5 minutes.

The absorbance of each well was detected at 570 nm wavelength with a microplate reader, and the IC50 of the compounds was calculated.

TABLE 1

The IC50 value of the compound of the present disclosure on the inhibition of HL60 cells.

| Compound No. | HL60/IC50 |
|---|---|
| A1 | A |
| A2 | A |
| A3 | C |
| A4 | A |
| A5 | A |
| A6 | A |
| A7 | A |
| A8 | A |
| A9 | B |
| A10 | A |
| A11 | B |
| A12 | A |
| A13 | A |
| A14 | A |
| A15 | A |
| A16 | A |
| A17 | A |
| A18 | A |
| A19 | B |
| A20 | A |
| A21 | A |
| A22 | B |
| A23 | B |
| A24 | A |
| A25 | A |
| A26 | C |
| A27 | A |
| A28 | C |
| A29 | A |
| A30 | A |
| A31 | A |
| A32 | A |
| A33 | C |
| A34 | B |
| A35 | B |
| A36 | A |
| A37 | A |
| A38 | B |
| A39 | C |
| A40 | C |
| A41 | C |
| A42 | A |
| A43 | A |
| A44 | A |
| A45 | A |
| A46 | B |
| A47 | A |
| A48 | A |
| A49 | D |
| A50 | D |
| A51 | A |
| A52 | A |
| A53 | D |
| A54 | D |
| A55 | C |
| A56 | C |
| A57 | C |
| A58 | B |
| A59 | C |
| A60 | C |
| A61 | B |
| A62 | B |
| A63 | B |
| A64 | C |
| A65 | A |
| A66 | A |
| A67 | A |
| A68 | B |
| A69 | A |
| A70 | A |
| A71 | A |
| A72 | C |
| A73 | A |
| A74 | A |
| A75 | A |

TABLE 1-continued

| The IC50 value of the compound of the present disclosure on the inhibition of HL60 cells. | |
|---|---|
| Compound No. | HL60/IC50 |
| A76 | A |
| A77 | A |
| A78 | A |
| A79 | B |
| A80 | A |
| A81 | B |
| A82 | D |
| A83 | D |
| A84 | A |
| A85 | B |
| A86 | A |
| A87 | A |
| A88 | A |
| A89 | B |
| A90 | D |
| A91 | D |
| A92 | B |
| A93 | C |
| A94 | C |
| A95 | C |
| A96 | B |
| A97 | C |
| A98 | C |
| A99 | B |
| A100 | C |
| A101 | B |
| A102 | B |
| A103 | C |
| A104 | B |
| A105 | B |
| A106 | B |
| A107 | C |

Note: A represents that the IC50 of the compound is below 100 nM, B represents that the IC50 of the compound is 100~500 nM, C represents that the IC50 of the compound is 500 nM~2 μM, and D represents the IC50 of the compound is 2~10 μM.

The experimental results of Tables 1, 2 shows that the compound of the present disclosure has excellent inhibitory effects on HL60, K562, KYSE510, and H460 cells, and can be used for cancer prevention and treatment.

TABLE 2

| The IC50 value of the compound of the present disclosure on the inhibition of other c-Myc high-expressing cells. | | | |
|---|---|---|---|
| Compound No. | K562/IC50 | KYSE510/IC50 | H460/IC50 |
| A10 | A | A | A |
| A67 | A | A | A |
| A69 | A | A | A |

Note: A represents that the IC50 of the compound is below 100 nM.

Effect Example 2: Test of the Binding Affinity Effect of the Compound of the Present Disclosure on C-Myc Protein 1. Experiment Preparation 10×PBS-P was diluted into 1.05×PBS-P buffer solution for later use. The c-Myc370-412-biotin peptide was dissolved in chromatographic pure DMSO to prepare a 1 mM stock solution. The molecules were dissolved in chromatographic pure DMSO to prepare a 10 mM stock solution. Part of 1.05×PBS-P buffer was added to chromatographic pure DMSO to prepare 1.00×PBS-P buffer (5% DMSO, ready for use).

The highest solubility of each small molecule in the 1.00×PBS-P buffer (5% DMSO) system was tested respectively. This solubility was used as the highest concentration tested for small molecule activity.

2. Protein Immobilization

The c-Myc370-412-biotin peptide stock solution was added to 1.05×PBS-P buffer to prepare a 50 μM solution, and then diluted with 1.00×PBS-P buffer (5% DMSO) to 1 g/ml for protein immobilization.

After washing the sample channel and reference channel of the chip with 1.00×PBS-P buffer (5% DMSO), an automatic mode was used to immobilize the protein in the sample channel. The target amount of the immobilized protein was 500RU. The immobilization was successful. The buffer was used continuously to flush until equilibrium.

3. Small Molecule Activity Test.

Buffer was used to prepare different concentrations of small molecule compounds for sample testing. The system was 1.00×PBS-P buffer (5% DMSO). The difference was detected between the response of small molecules flowing through the sample channel and the reference channel.

The experimental conditions were a flow rate of 30 μL/min, binding time of 120 seconds, and dissociation time of 240 seconds. After each binding and dissociation test, 50% DMSO was used to flush the tubing, and 10 mM glycine-HCl buffer (pH 2.1) was used to flush the surface of the chip to wash away the remaining compound molecules.

TABLE 2

| Determination of the binding constant of the compound of the present disclosure on the c-Myc protein. | |
|---|---|
| Compound No. | SPR Kd |
| A2 | B |
| A3 | B |
| A4 | A |
| A5 | B |
| A6 | A |
| A7 | A |

Note: A represents that the Kd of the compound is below 100 nM, B represents that the Kd of the compound is 100~500 nM The content of the present disclosure only exemplifies some specific implementations as claimed, in which the technical features recorded in one or more technical solutions can be combined with any one or more technical solutions, and these technical solutions obtained by combination are also within the protection scope of the present application, just as these combined technical solutions have been specifically recorded in the present disclosure.

The invention claimed is:

1. A compound or a pharmaceutically acceptable salt, a solvate, a stereoisomer or a prodrug thereof, wherein the compound has the following structures:

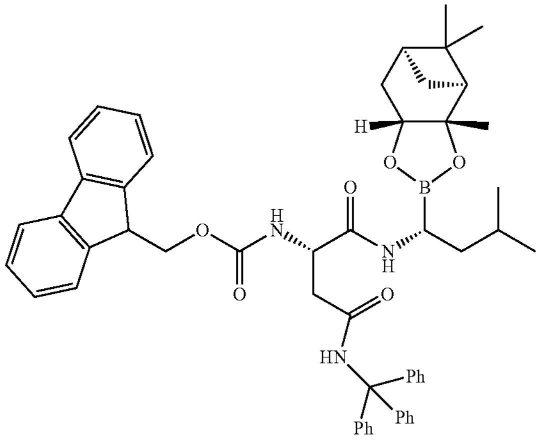
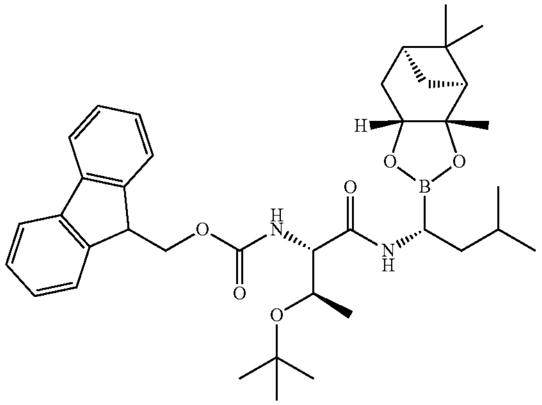
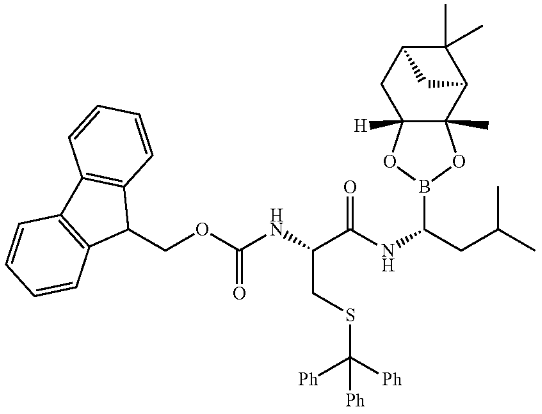
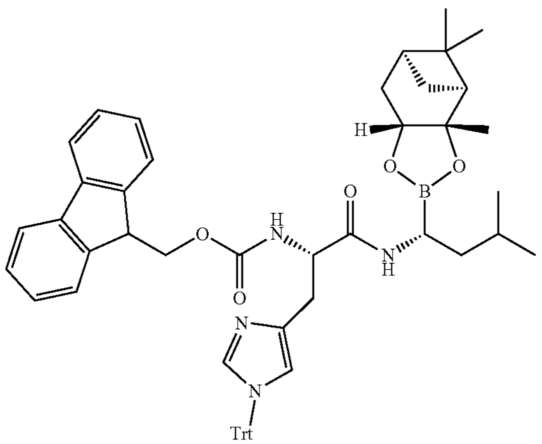
-continued
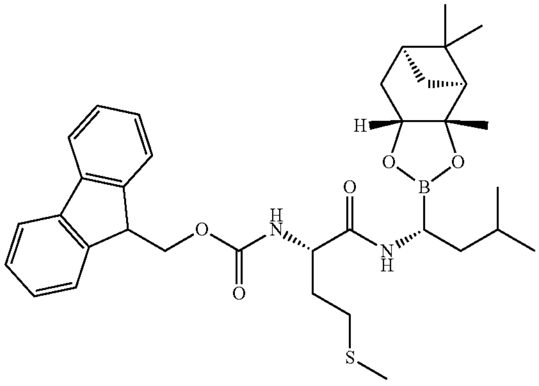
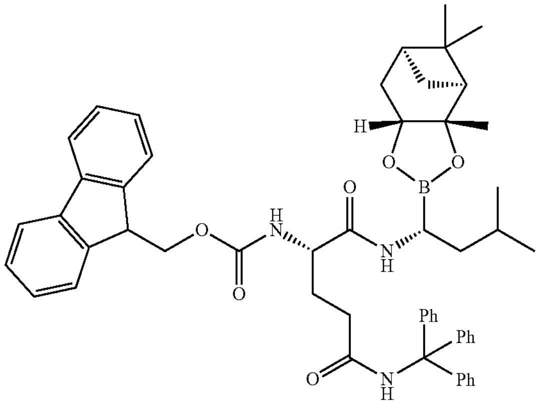
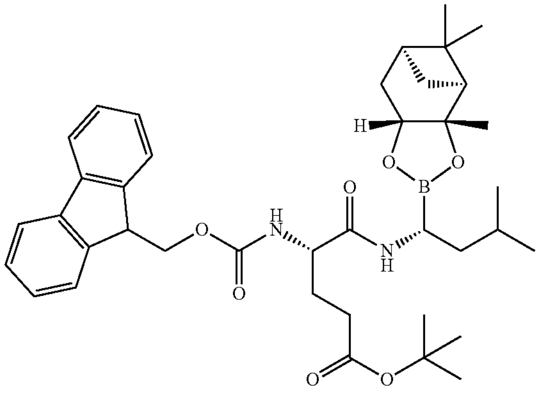
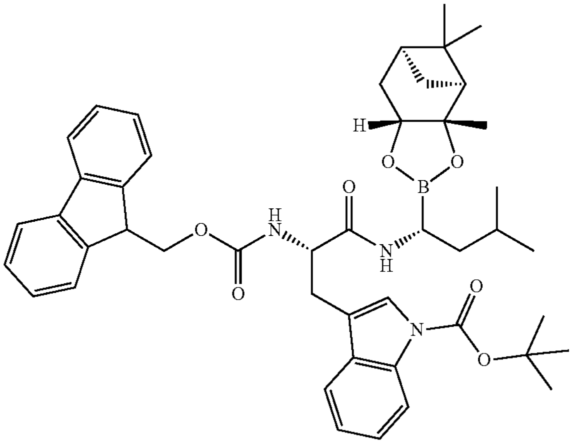

-continued
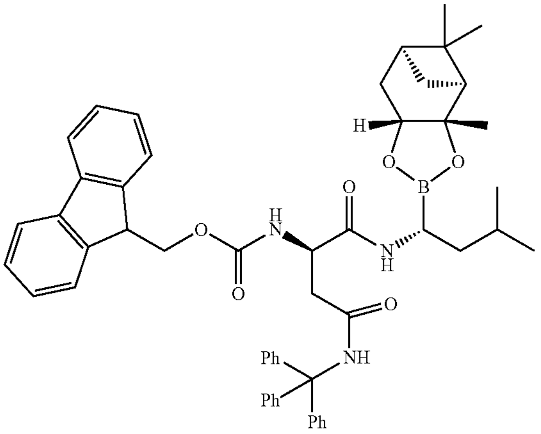
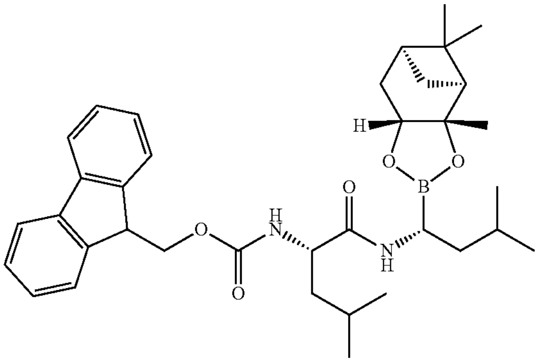
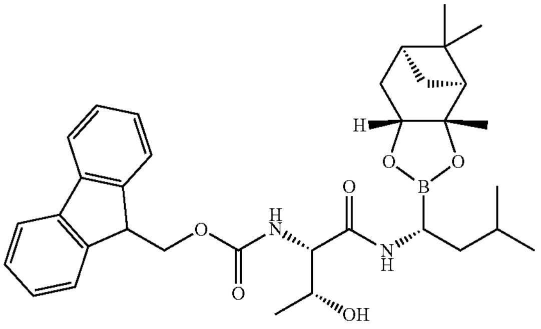
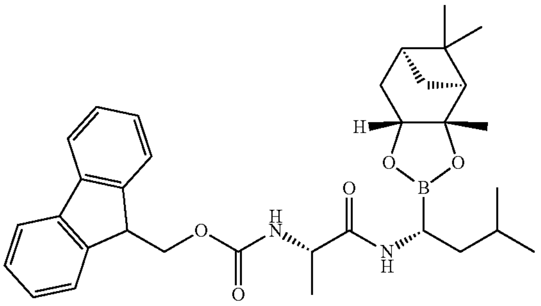
-continued
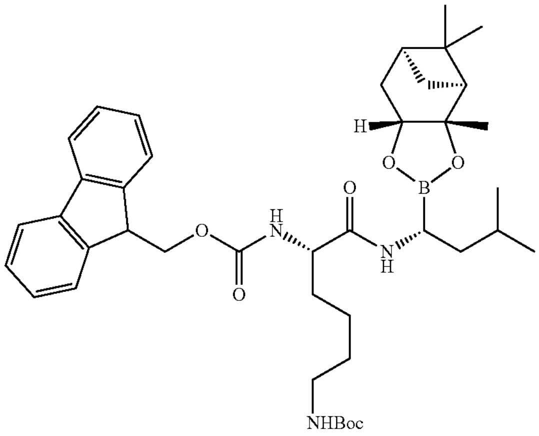
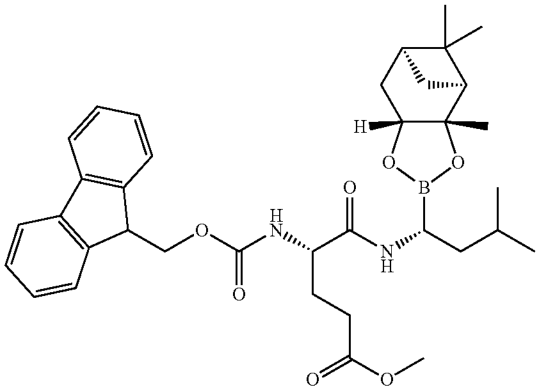
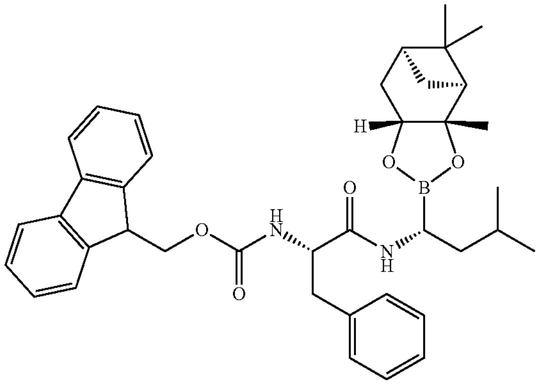
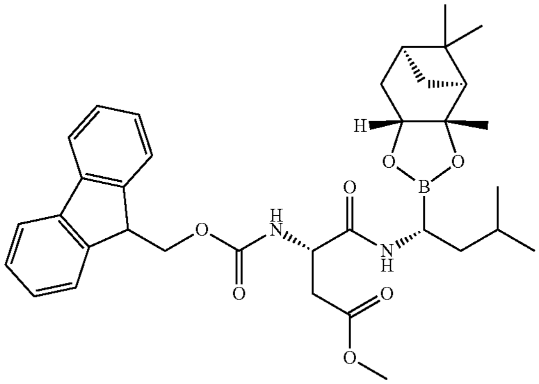

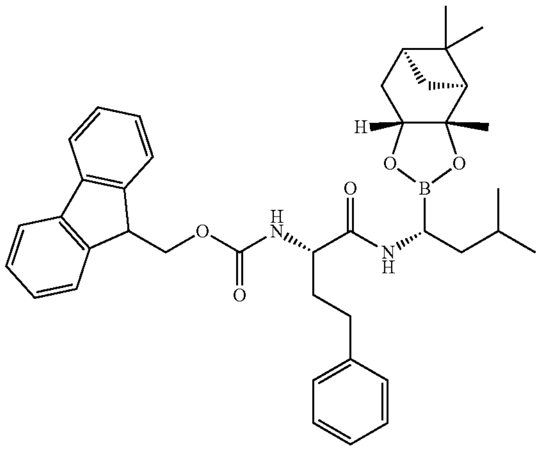
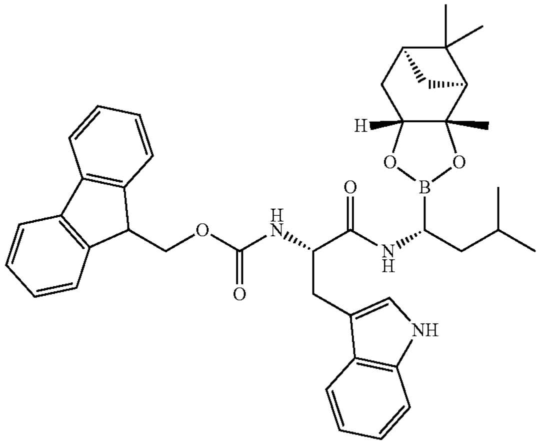
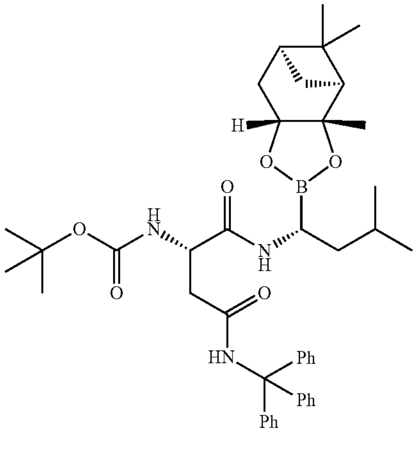
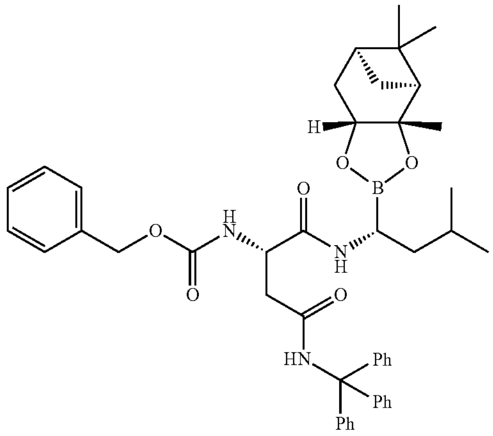
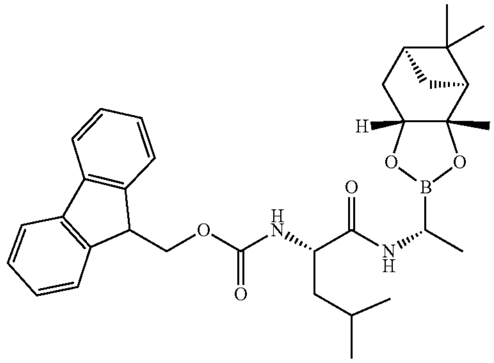
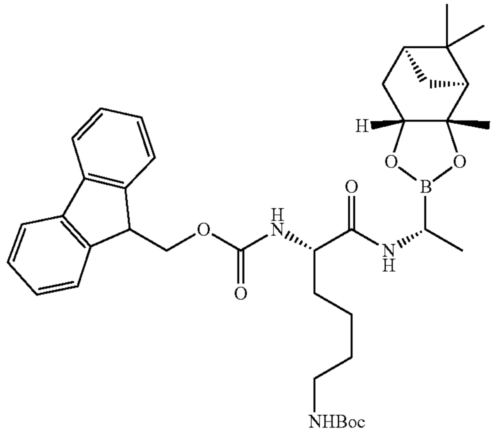
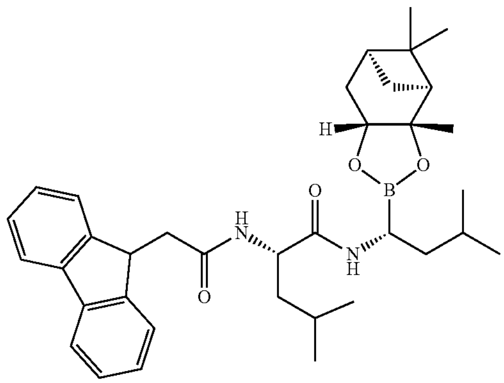

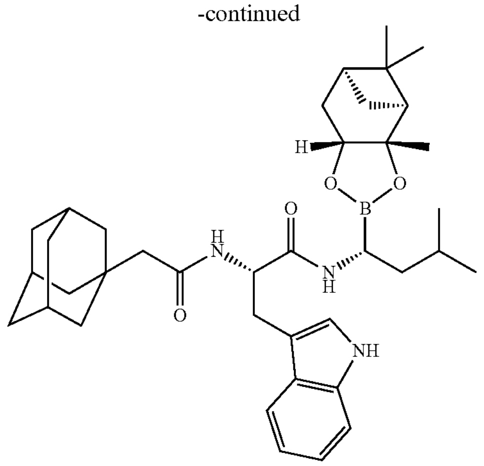
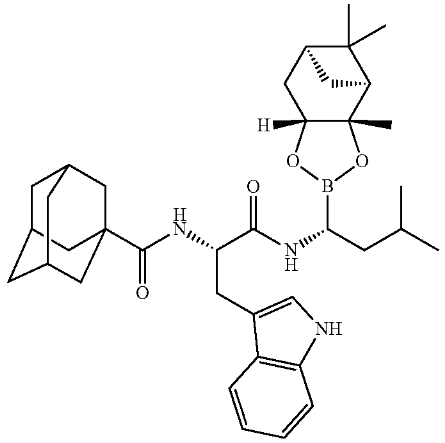
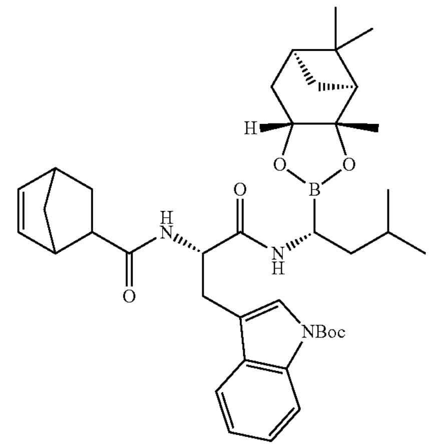
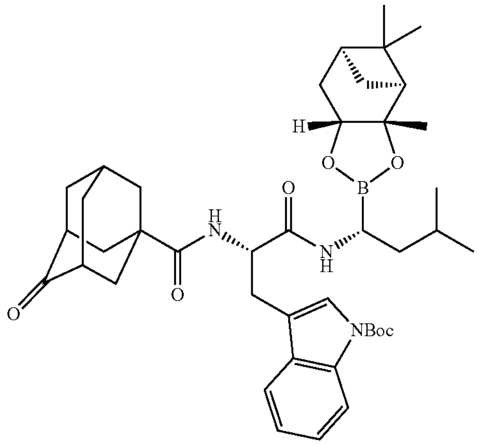
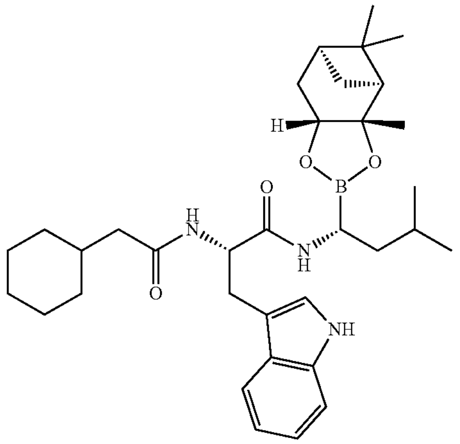
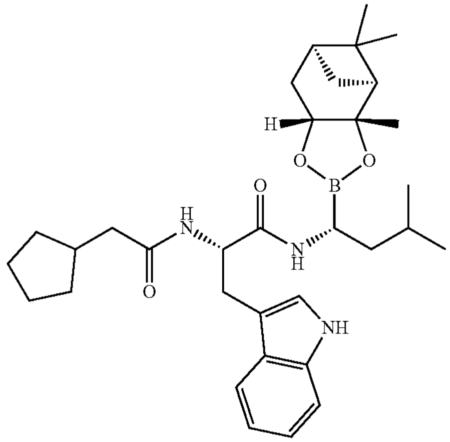

-continued
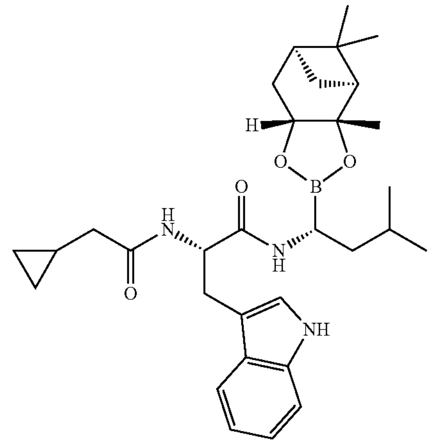
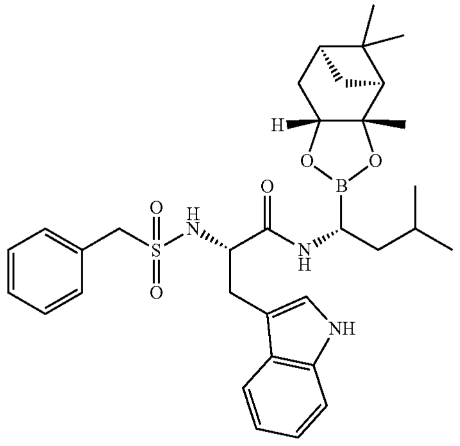
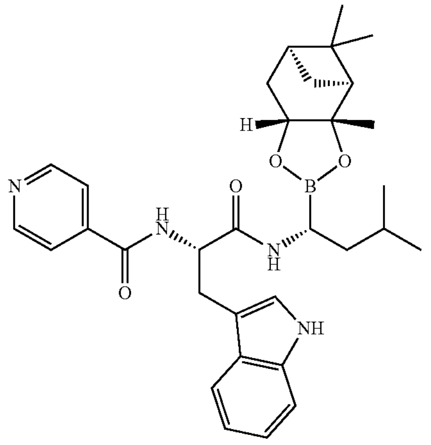
-continued
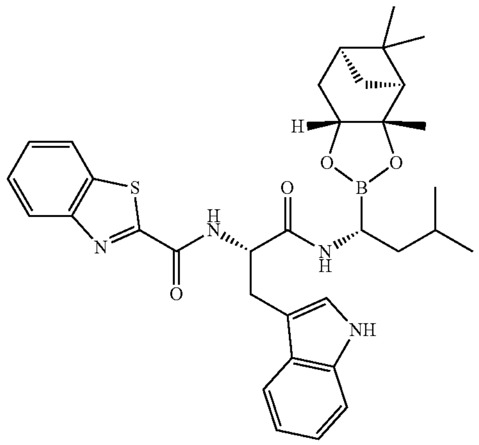
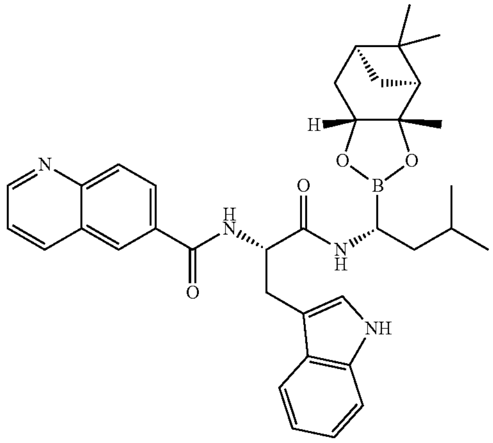
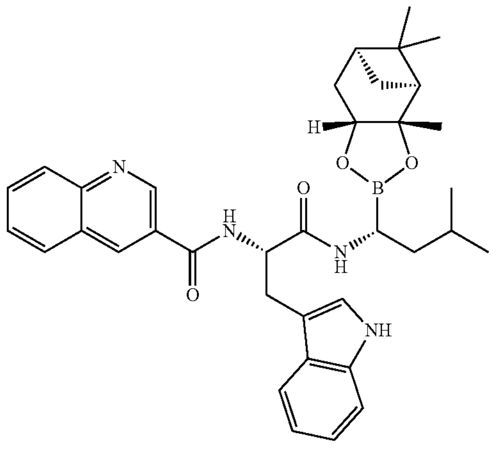

-continued
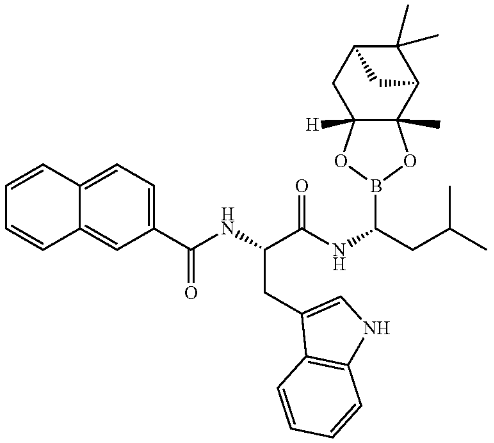
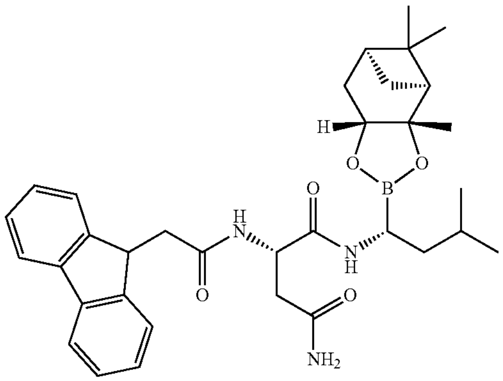
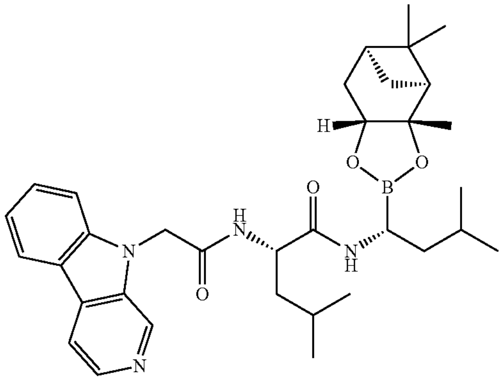
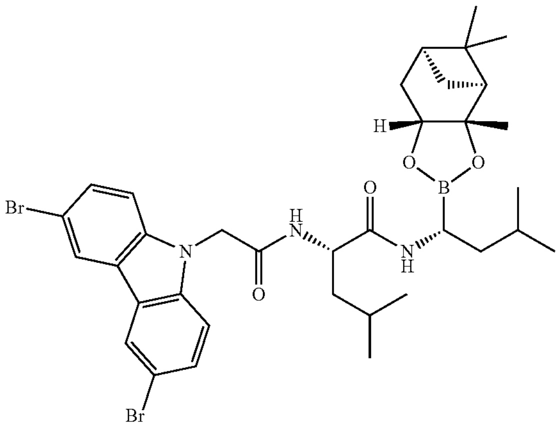
-continued
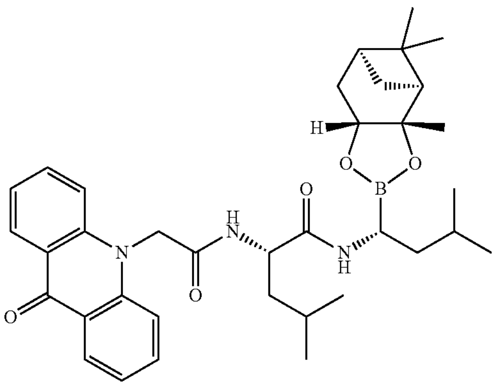
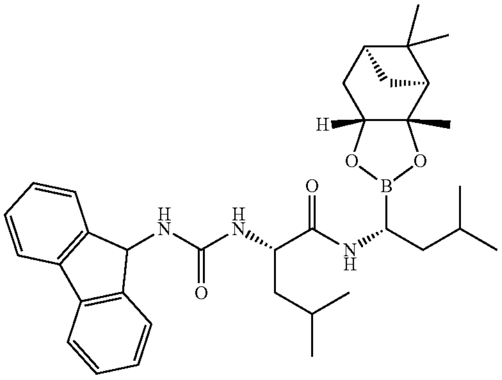
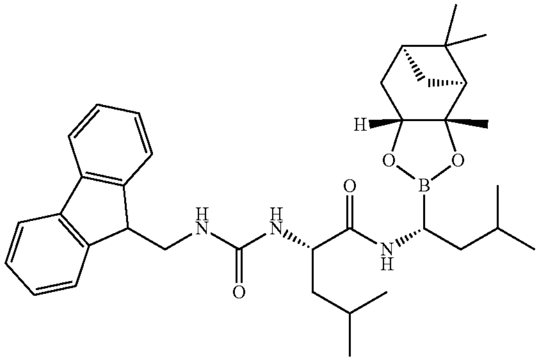
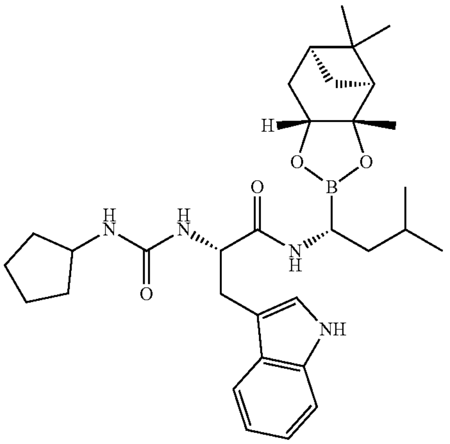

-continued
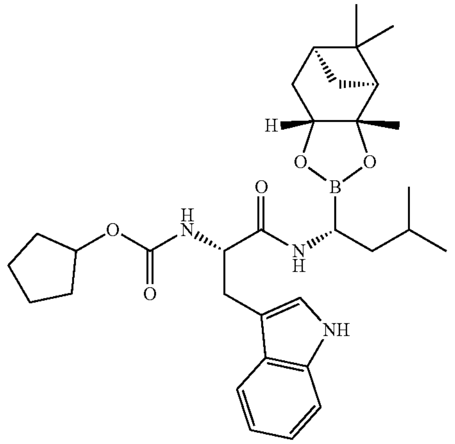
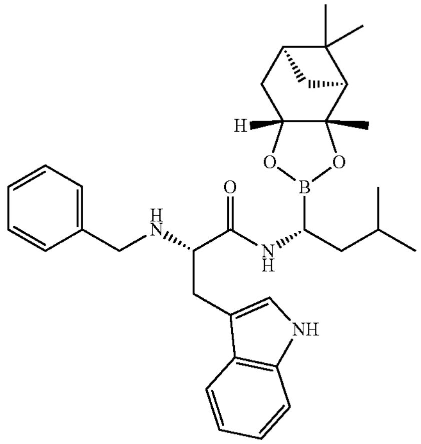
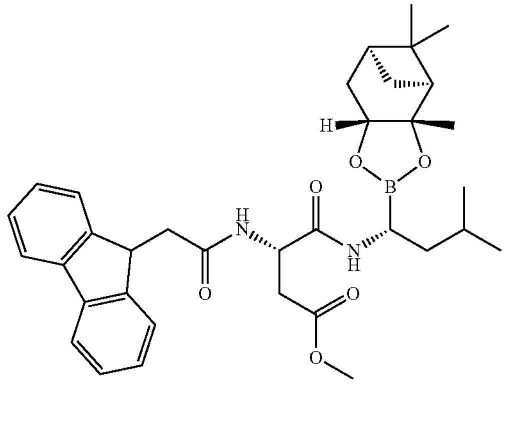
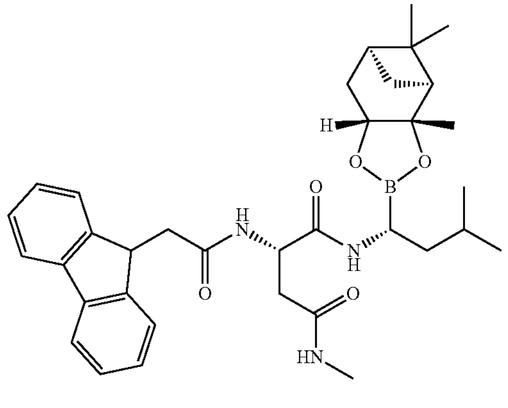
-continued
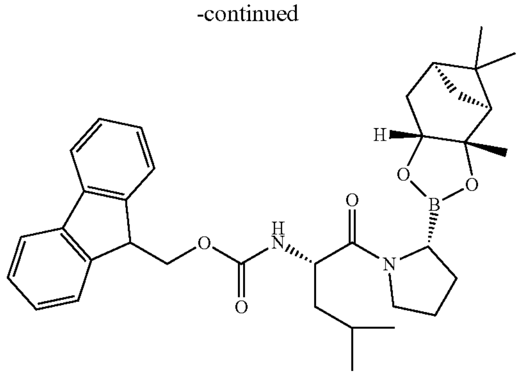
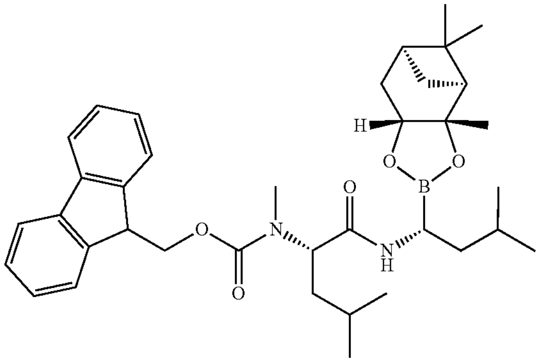
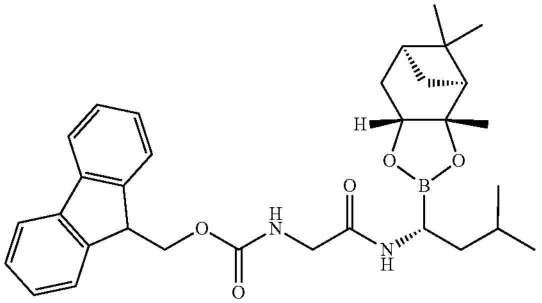
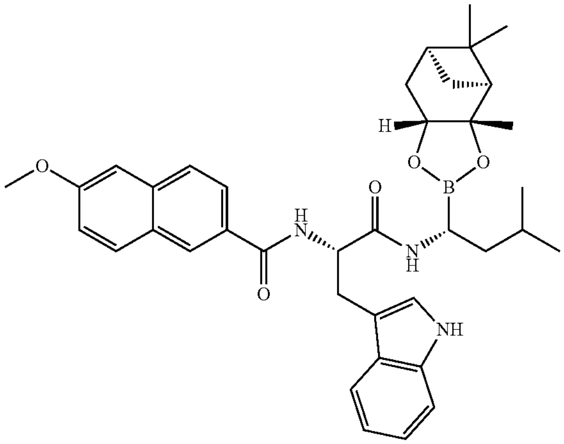
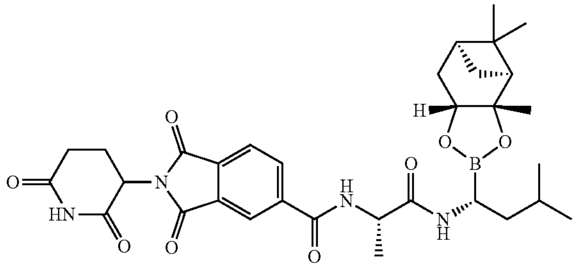

-continued
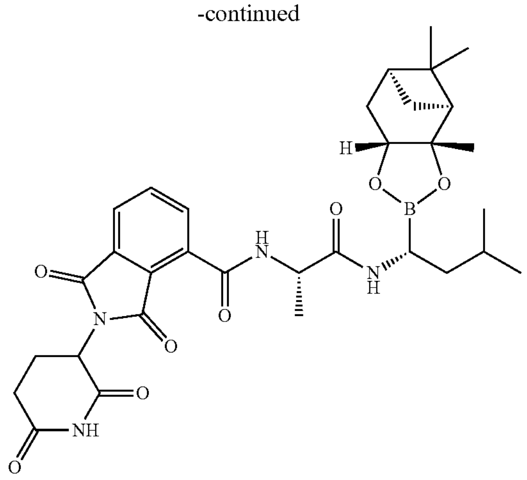
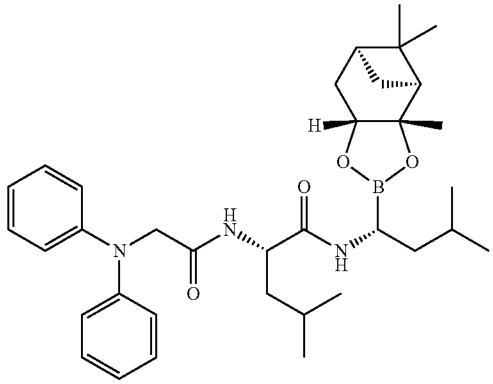
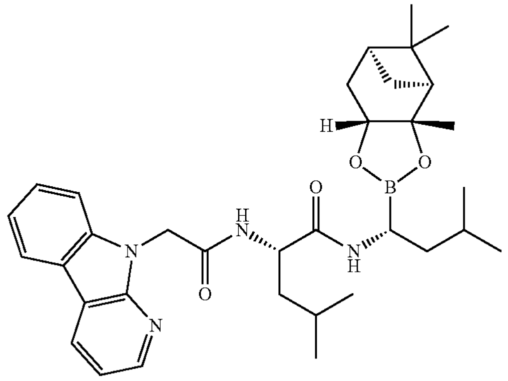
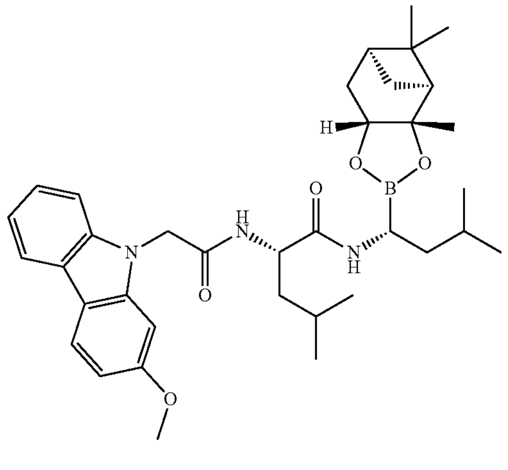
-continued
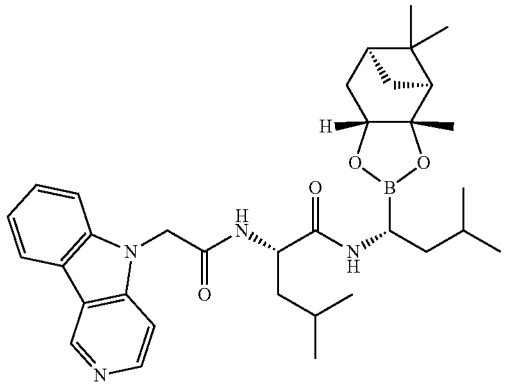
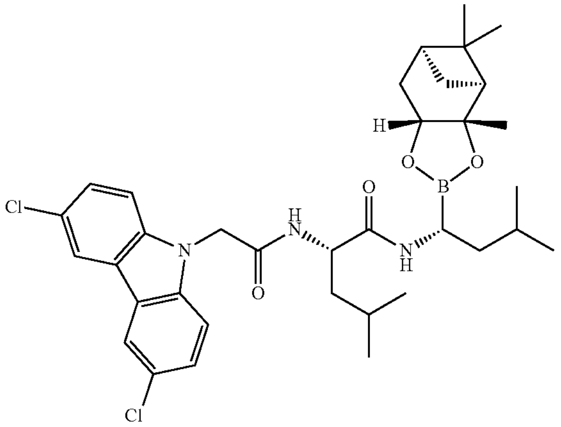
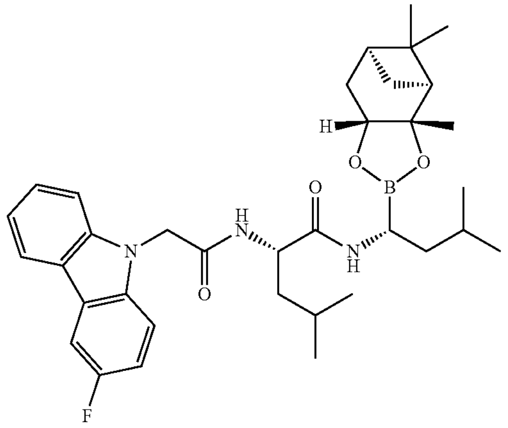
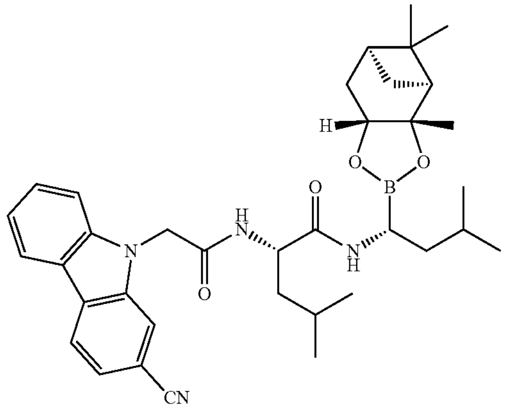

-continued
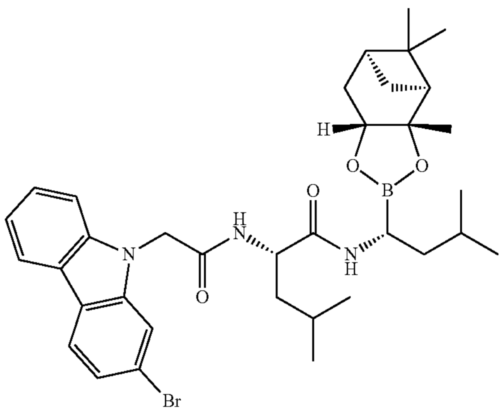
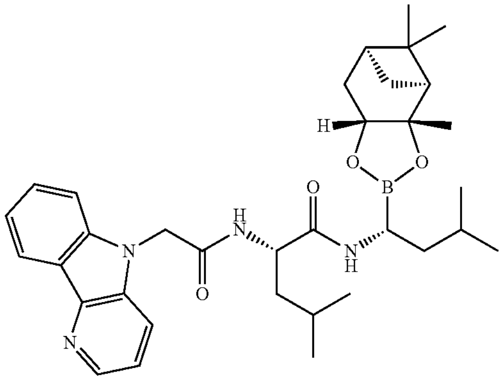
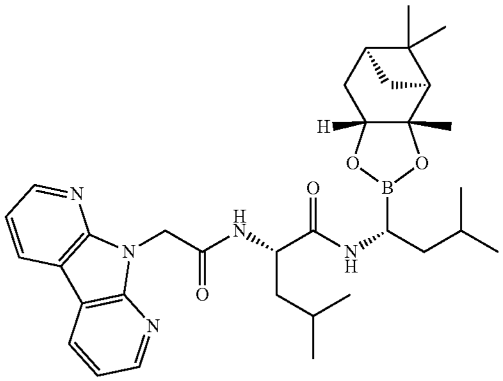
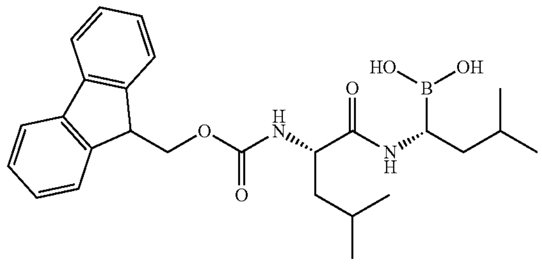
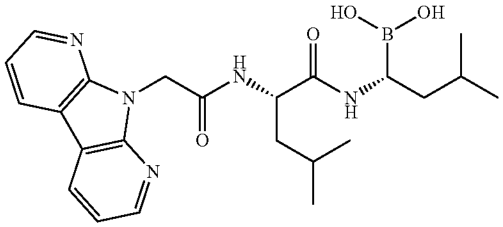
-continued
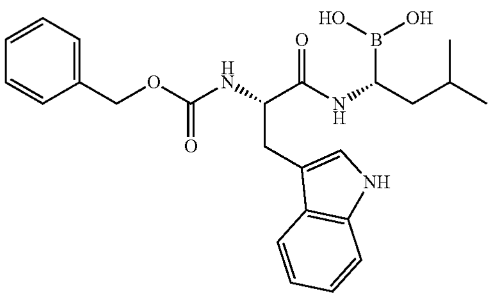
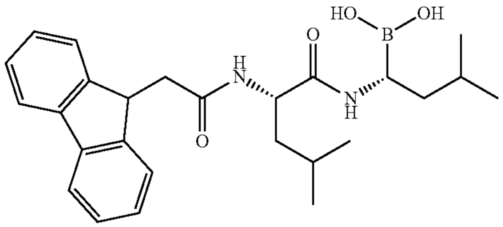
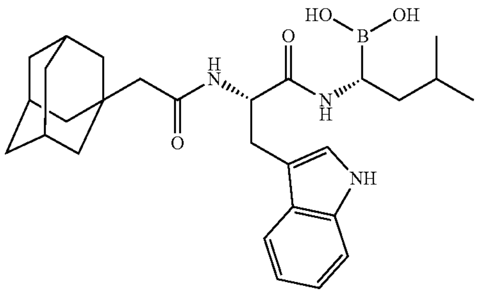
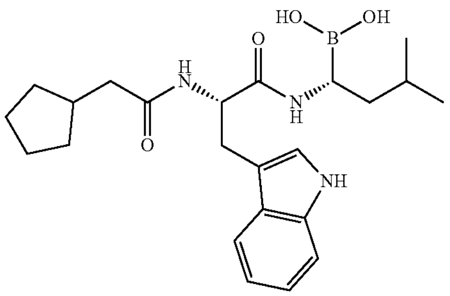
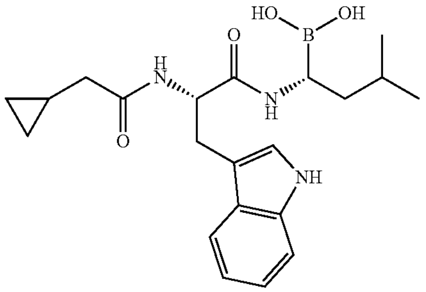
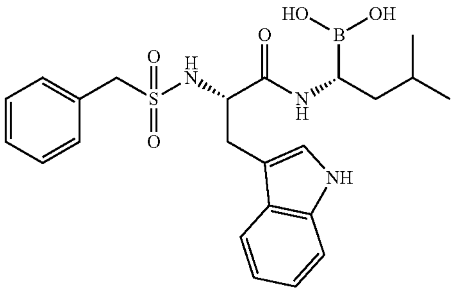

-continued
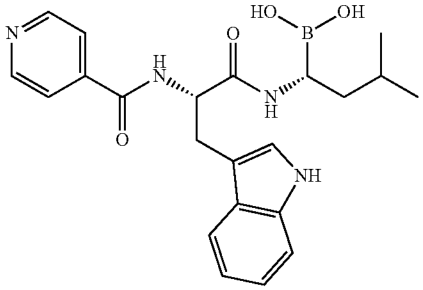
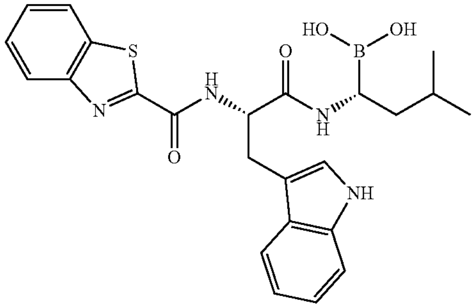
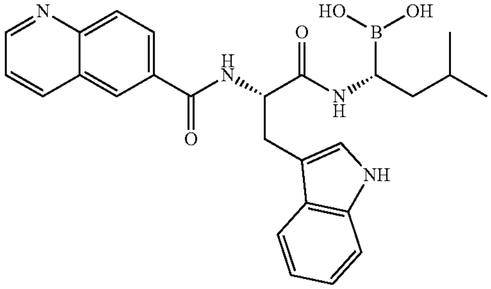
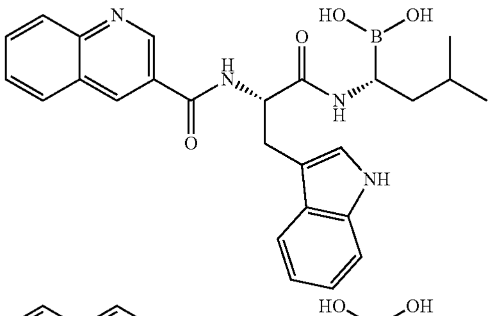
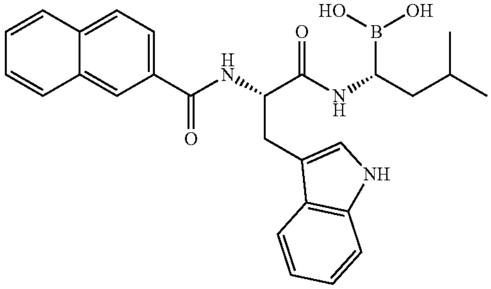
-continued
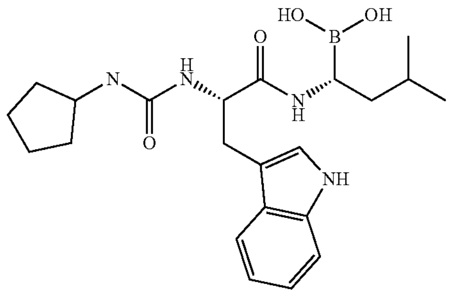
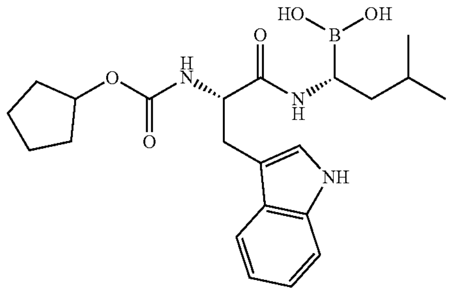
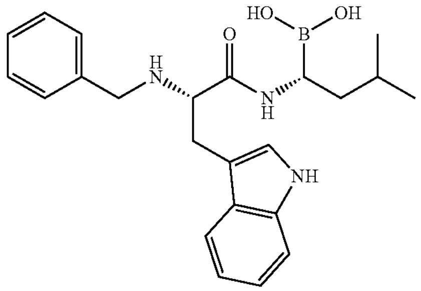
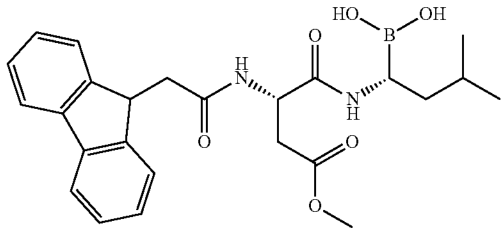
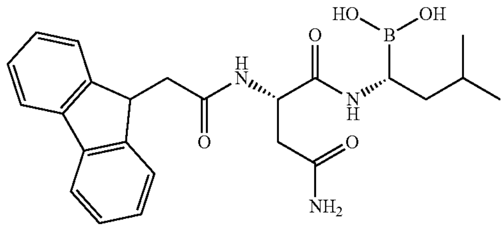
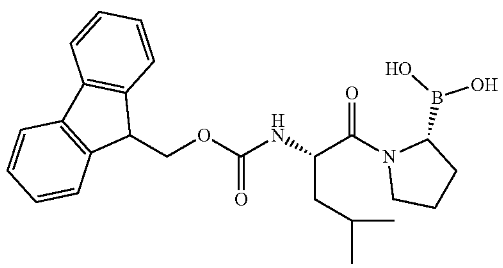

-continued
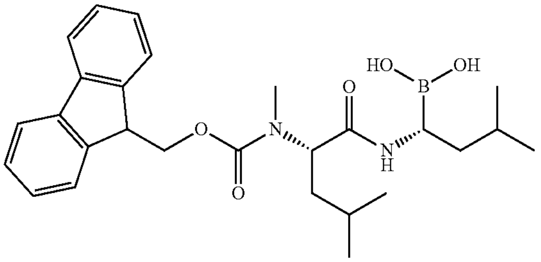
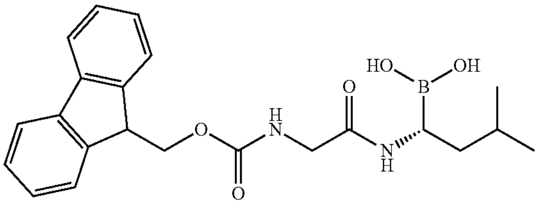
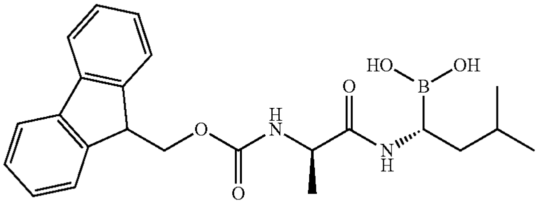
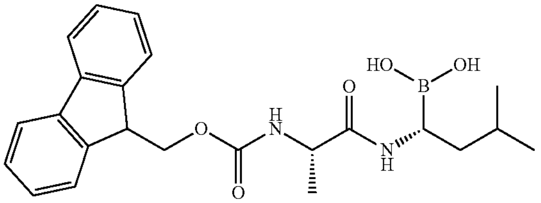
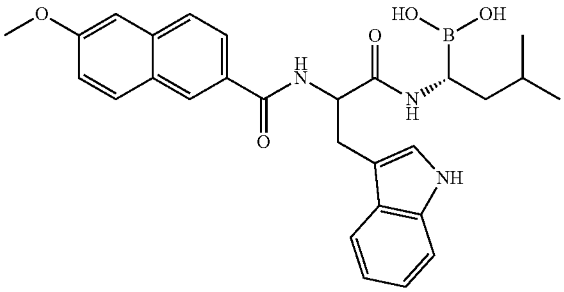
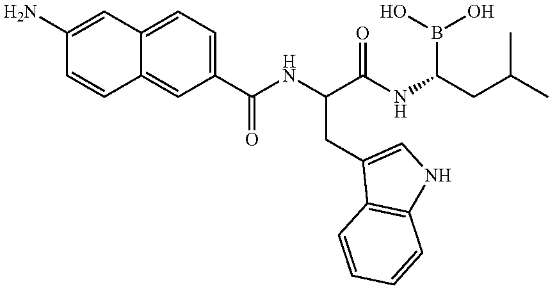
-continued
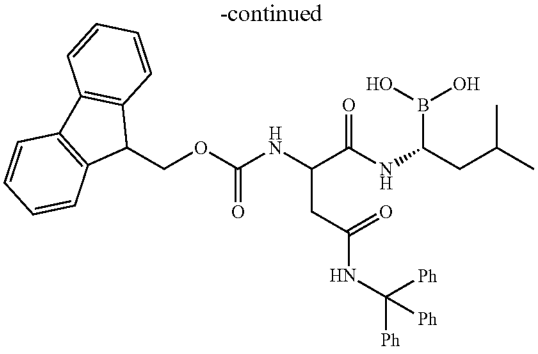
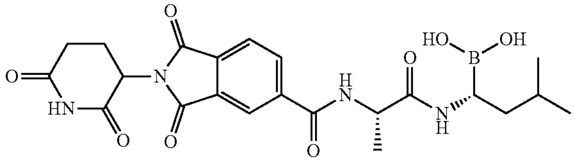
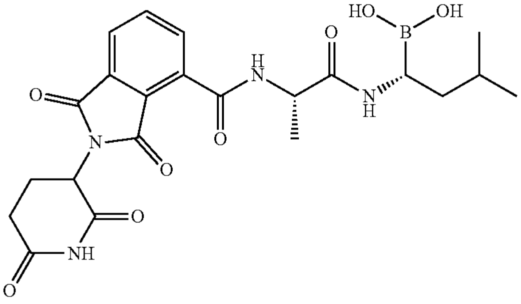
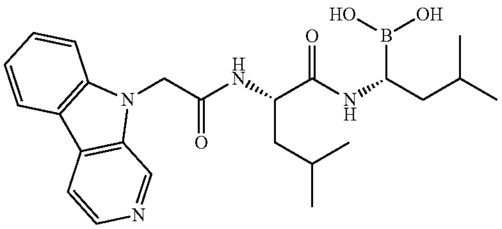
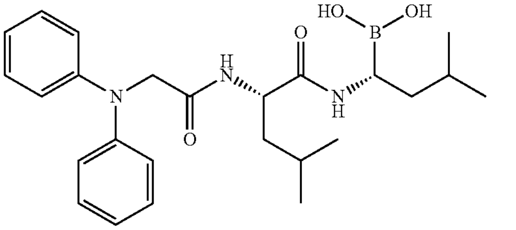
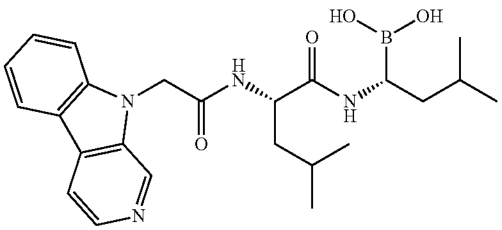

-continued
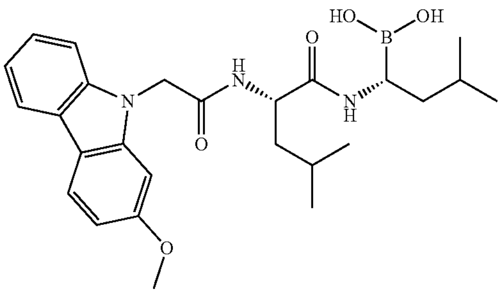
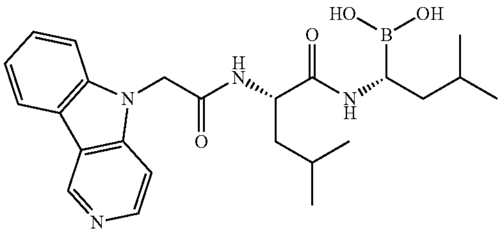
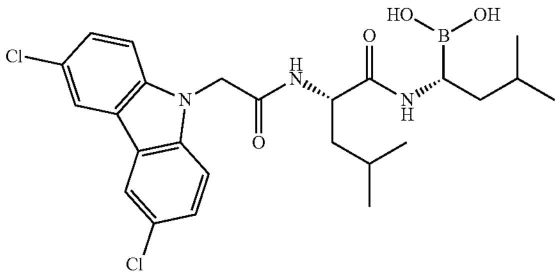
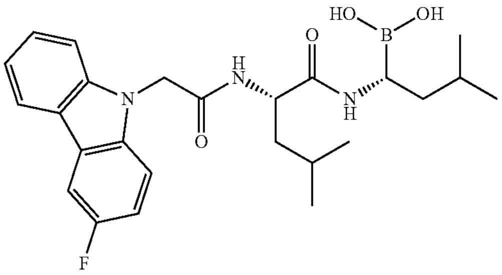
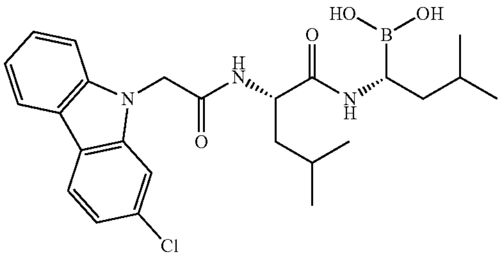
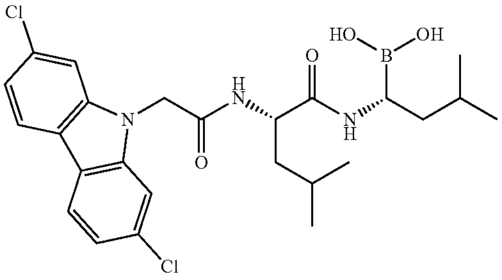
-continued
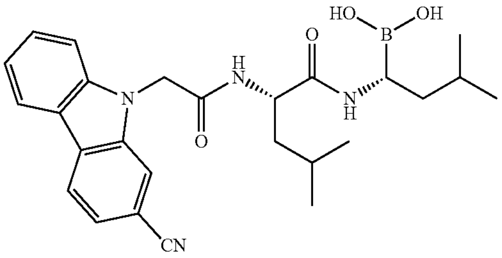
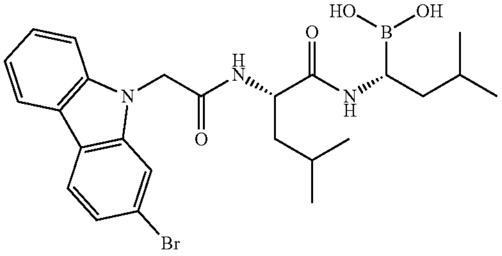
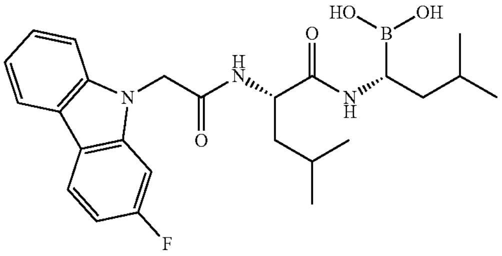
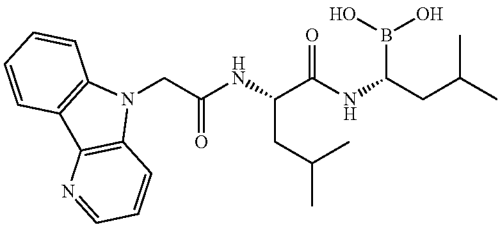
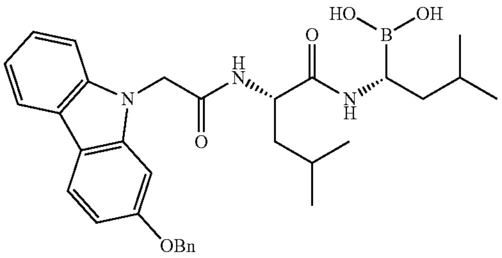
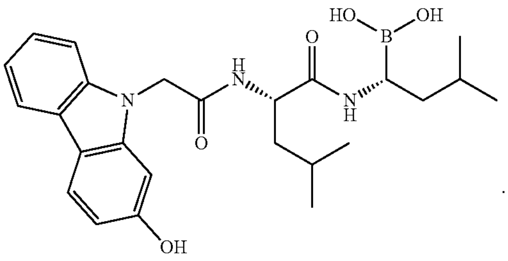
2. A pharmaceutical composition, comprising a pharmaceutically acceptable carrier and the compound or the pharmaceutically acceptable salt, the solvate, the stereoisomer or the prodrug thereof according to claim 1.

3. A method for treating a disease related to a c-Myc protein disorder, comprising administering to a subject in need thereof a therapeutically effective amount of a compound or a pharmaceutically acceptable salt, solvate, stereoisomer, or prodrug thereof according to claim 1, wherein the disease related to a c-Myc protein disorder is selected from the group consisting of esophageal cancer, leukemia, and lung cancer.

* * * * *